United States Patent
Tyrlik et al.

(10) Patent No.: US 11,822,541 B2
(45) Date of Patent: Nov. 21, 2023

(54) TECHNIQUES FOR STORING SUB-ALIGNMENT DATA WHEN ACCELERATING SMITH-WATERMAN SEQUENCE ALIGNMENTS

(71) Applicant: NVIDIA CORPORATION, Santa Clara, CA (US)

(72) Inventors: Maciej Piotr Tyrlik, Durham, NC (US); Ajay Sudarshan Tirumala, San Jose, CA (US); Shirish Gadre, Fremont, CA (US)

(73) Assignee: NVIDIA CORPORATION, Santa Clara, CA (US)

( * ) Notice: Subject to any disclaimer, the term of this patent is extended or adjusted under 35 U.S.C. 154(b) by 98 days.

(21) Appl. No.: 17/491,266

(22) Filed: Sep. 30, 2021

(65) Prior Publication Data
US 2023/0095916 A1 Mar. 30, 2023

(51) Int. Cl.
*G06F 16/23* (2019.01)
*G16B 30/10* (2019.01)
*G16B 50/30* (2019.01)
*G06F 16/242* (2019.01)

(52) U.S. Cl.
CPC ........ *G06F 16/2379* (2019.01); *G06F 16/242* (2019.01); *G16B 30/10* (2019.02); *G16B 50/30* (2019.02)

(58) Field of Classification Search
CPC ... G06F 16/2379; G06F 16/242; G16B 30/10; G16B 50/30
See application file for complete search history.

(56) References Cited

U.S. PATENT DOCUMENTS

| | | |
|---|---|---|
| 7,467,287 B1 | 12/2008 | Bratt et al. |
| 2004/0024536 A1 | 2/2004 | Rognes |
| 2004/0098203 A1* | 5/2004 | Rognes ................. G16B 30/00 702/20 |
| 2004/0167720 A1* | 8/2004 | Poleksic ............... G16B 30/00 702/20 |
| 2008/0250016 A1* | 10/2008 | Farrar ................... G16B 30/00 |
| 2009/0125514 A1 | 5/2009 | Brown |

(Continued)

OTHER PUBLICATIONS

Notice of Allowance received for U.S. Appl. No. 17/491,279 dated Nov. 2, 2022, 10 pages.

(Continued)

*Primary Examiner* — Huawen A Peng
(74) *Attorney, Agent, or Firm* — Artegis Law Group, LLP

(57) ABSTRACT

Various techniques for accelerating Smith-Waterman sequence alignments are provided. For example, threads in a group of threads are employed to use an interleaved cell layout to store relevant data in registers while computing sub-alignment data for one or more local alignment problems. In another example, specialized instructions that reduce the number of cycles required to compute each sub-alignment score are utilized. In another example, threads are employed to compute sub-alignment data for a subset of columns of one or more local alignment problems while other threads begin computing sub-alignment data based on partial result data received from the preceding threads. After computing a maximum sub-alignment score, a thread stores the maximum sub-alignment score and the corresponding position in global memory.

20 Claims, 17 Drawing Sheets

(56) References Cited

U.S. PATENT DOCUMENTS

| | | | |
|---|---|---|---|
| 2012/0023110 A1* | 1/2012 | Zidan | G16B 50/30 |
| | | | 707/E17.014 |
| 2012/0239706 A1* | 9/2012 | Steinfadt | G16B 30/00 |
| | | | 707/E17.044 |
| 2013/0080490 A1 | 3/2013 | Plondke et al. | |
| 2013/0166218 A1* | 6/2013 | Farivar | G16B 30/00 |
| | | | 702/19 |
| 2014/0172824 A1* | 6/2014 | Musuvathi | G16B 30/10 |
| | | | 707/719 |
| 2014/0189320 A1 | 7/2014 | Kuo | |
| 2015/0057946 A1 | 2/2015 | Kural | |
| 2015/0220532 A1* | 8/2015 | Wong | G06F 17/18 |
| | | | 707/756 |
| 2015/0227685 A1* | 8/2015 | Kural | G16B 30/10 |
| | | | 702/19 |
| 2016/0124715 A1 | 5/2016 | Burgess et al. | |
| 2018/0137237 A1* | 5/2018 | Lo | G06F 7/02 |
| 2020/0234796 A1* | 7/2020 | Narayanasamy | G16B 30/10 |
| 2021/0133175 A1 | 5/2021 | Shabi et al. | |

OTHER PUBLICATIONS

Steinfadt et al., "SWAMP: Smith-Waterman using Associative Massive Parallelism", IEEE, 2008, 8 pages.

* cited by examiner

SW Two Problem Pseudocode 910

```
SW_2_example( ) {
    // initialize result                              ┌─ Initialization Pseudocode 920
    SWresultsSIMD2 result { .result16 { 0, 0, 0, 0, 0, 0 };
    // temporary storage for the matrix-filling dataset 490(0)
    SWcell16_t cells[2, N+1];
    // initialize top row and left entry of next row to 0
    memset(cells[0], 0, sizeof(SWcell_t)*(N+1));
    memset(cells[1], 0, sizeof(SWcell_t));
    for (uint32_t row = 1; row <= M; ++row) {
        const uint32_t prevID = (row % 2) == 0 ? 1 : 0;
        const uint32_t currentID = row % 2;
        // substitution loop - get substitution values for row
        for (uint32_t col = 1; col <= N; ++col)
            cells[prevID][col-1].S0 = SubstitutionMatrix.at(T0[row-1]).at(Q0[col-1]);
            cells[prevID][col-1].S1 = SubstitutionMatrix.at(T1[row-1]).at(Q1[col-1]);
        // main loop - process single row
        for (uint32_t col = 1; col <= N; ++col) {
            __sw_16(cells[currentID][col], cells[prevID][col-1],
                    cells[prevID][col], cells[currentID][col-1], consts);
            __vimnmx_16(result.r32.maxH, pu, pv, px, py,
                        cells[currentID][col].c32.H, result.r32.maxH);
            if (pu) {
                result.r16.maxH0row = static_cast<uint16_t>(row);
                result.r16.maxH0col = static_cast<uint16_t>(col);
            }
            if (pv) {
                result.r16.maxH1row = static_cast<uint16_t>(row);
                result.r16.maxH1col = static_cast<uint16_t>(col);
            }
        }
    }
}
```

Initialization Pseudocode 920

Row Identifier Swap Pseudo-Code 930

Substitution Value Assignment Pseudo-Code 940

Sub-Alignment Computation Pseudocode 950

Result Computation Pseudocode 960

FIGURE 9

SW Sequence Pseudocode 1002

```
// Per-thread six-instruction sequence for a Smith-Waterman scoring computation
// for noSIMD, Matrix-Filling Dataset 490(1), and 32-bit signed integers
void __sw6_1(HEcell &resultCell, int32_t &resultF,
             HEcell &diagCell, HEcell &topCell, HEcell &leftCell,
             int32_t inputF, int32_t S, const SWconsts32 &consts) {
    __viadd(resultCell.E, topCell.E, consts.gde, false);
    __viaddmnmx(resultCell.E, topCell.E, consts.gdo, resultCell.E,
                true, false, false);
    __viadd(resultF, inputF, consts.gie, false);
    __viaddmnmx(resultF, leftCell.H, consts.gio, resultF, true, false, false);
    __viadd(resultCell.H, diagCell.H, S, false);
    __vimnmx3(resultCell.H, resultCell.E, result.F, resultCell.H, true, true, false);
}
```

SW Single Problem Pseudocode 1010

```
SW6_1_example() {
    // initialize result
    SWresultsSIMD1 result { 0, 0, 0 };                          ⎫ Initialization
    // temporary storage for the matrix-filling dataset 490(1)  ⎬ Pseudocode
    HEcell32_t cells[2, N+1];                                   ⎪ 1020
    int32_t F[N+1];
    int32_t S[N];
    // initialize top row, left entry of next row, and left entry of F to 0
    memset(cells[0], 0, sizeof(HEcell_t)*(N+1));
    memset(cells[1], 0, sizeof(HEcell_t));
    for (uint32_t row = 1; row <= M; ++row) {                   ⎫ Row Identifier Swap
        const uint32_t prevID = (row % 2) == 0 ? 1 : 0;         ⎬ Pseudocode 1030
        const uint32_t currentID = row % 2;                     ⎭
        // substitution loop - get substitution values for row      Substitution
        for (uint32_t col = 1; col <= N; ++col)                 ⎫ Value
            S[col-1] = SubstitutionMatrix.at(T0[row-1]).at(Q0[col-1]); ⎬ Assignment
        // main loop - process single row                       ⎭ Pseudocode
        for (uint32_t col = 1; col <= N; ++col) {                 1040
            __sw6_1(cells[index_current][col], F[col], cells[index_prev][col-1],
                cells[index_prev][col], cells[index_current][col-1], F[col-1],
                S[col-1], consts);
            __vimnmx_32(result.maxH, pu, pv, px, py,            ⎫ Sub-Alignment
                        cells[currentID][col].H, result.maxH);  ⎬ Computation
            if (pu) {                                           ⎪ Pseudocode
                result.maxHrow = row;                           ⎪ 1050
                result.maxHcol = col;                           ⎭
            }
        }  ⎺ Result Computation Pseudocode 1060
    }
}
```

FIGURE 10

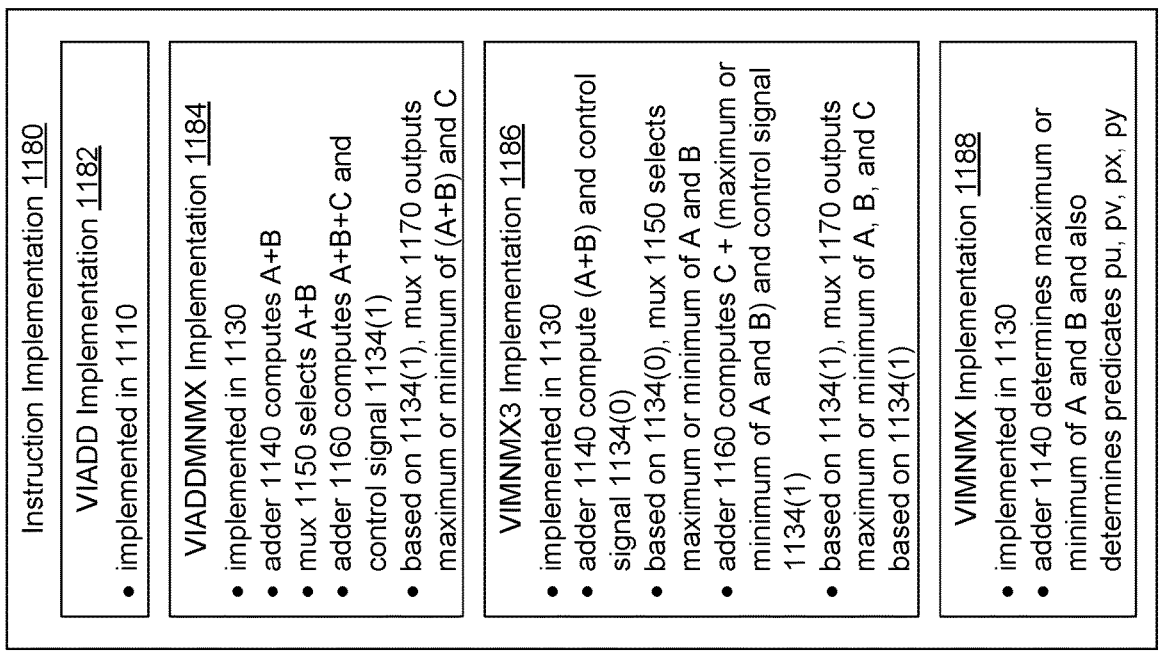
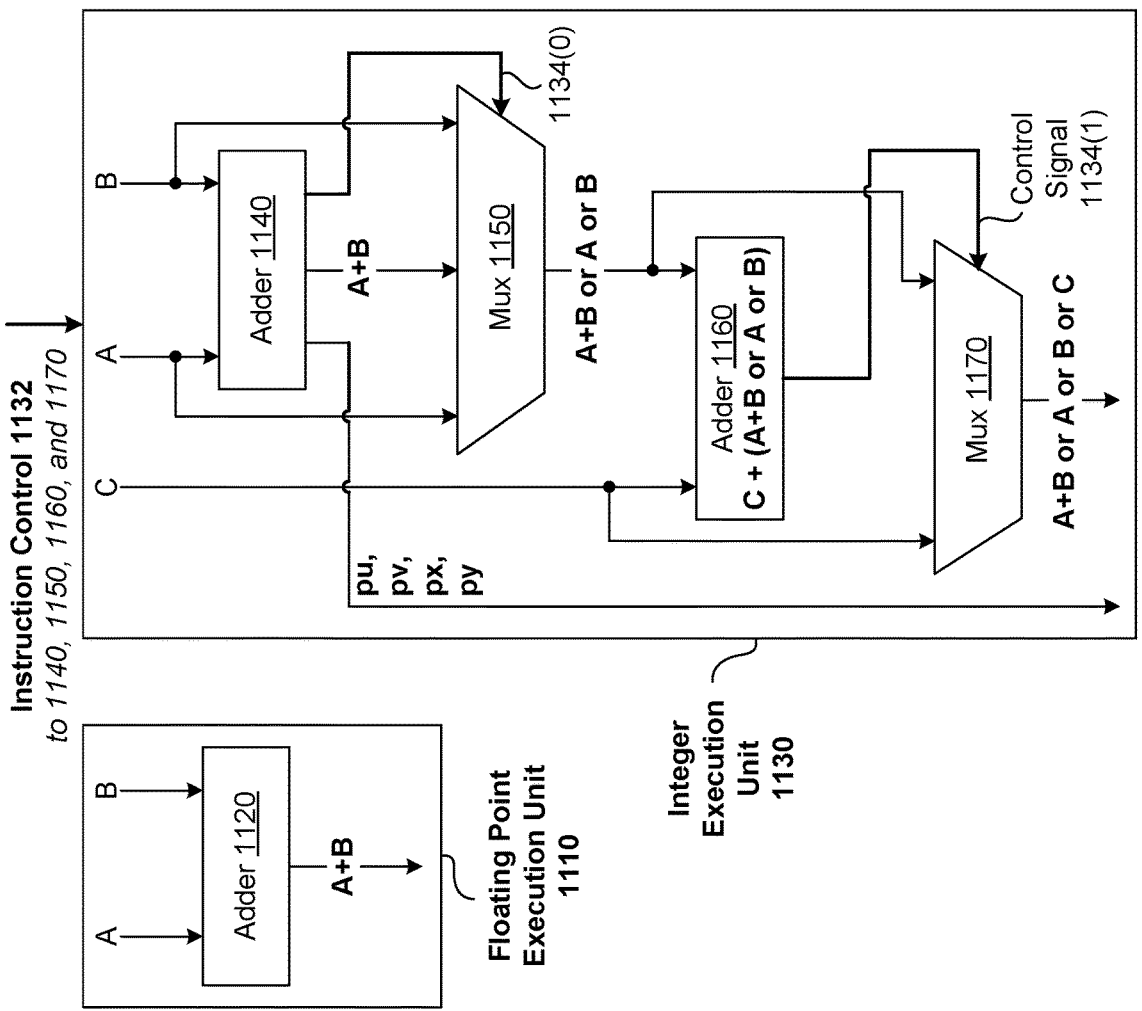
FIGURE 11

TECHNIQUES FOR STORING SUB-ALIGNMENT DATA WHEN ACCELERATING SMITH-WATERMAN SEQUENCE ALIGNMENTS

BACKGROUND

Field of the Various Embodiments

The various embodiments relate generally to parallel processing systems and, more specifically, to techniques for storing sub-alignment data when accelerating Smith-Waterman sequence alignments.

Description of the Related Art

The Smith-Waterman algorithm is used in a wide variety of applications, such as scientific, engineering, and data applications, to quantify how well subsequences of two sequences can be aligned and determine an optimized alignment of subsequences or "local alignment" of those sequences. For example, the Smith-Waterman algorithm is a building block of many genomics algorithms, such as algorithms for determining DNA sequences of organisms and for comparing DNA or protein sequences against genome databases.

To solve a local alignment problem for a target sequence "T" and a query sequence "Q" using the Smith-Waterman algorithm, a software application implements a matrix-filling phase and either a back-tracking phase or a reversed matrix-filling phase. During the matrix-filling phase, the software application implements a dynamic programming technique to break the computation of the optimized local alignment into computations of inter-dependent sub-alignment scores included in a two-dimensional (2D) scoring matrix "H." The scoring matrix includes, without limitation, a top-most row and a left-most column of initial values, a different row for each symbol of the target sequence, and a different column for each symbol of the query sequence. For a target sequence of length of M and a query sequence Q of length N, the scoring matrix therefore is an (M+1)×(N+1) matrix. Because of the offsets introduced by the row and the column of initial values, for $0<j<=M$ and $0<k<=N$, the sub-alignment score denoted H(j, k) quantifies the maximum similarity between any subsequence of T that ends in the symbol T(j−1) and any subsequence of Q that ends in the symbol Q(k−1). As part of the matrix-filling phase, the software application determines a maximum sub-alignment score and the position of the maximum sub-alignment score within the scoring matrix. During either the back-tracking phase or the reversed matrix-filling phase, the software application determines the starting position within the scoring matrix that corresponds to the maximum sub-alignment score. The starting position and the position of the maximum sub-alignment score define the target subsequence and the query subsequence corresponding to the optimized local alignment of the target sequence and query sequence.

Because executing the matrix-filling phase for T having a length of M and Q having a length of N takes on the order of (M×N) time or "quadratric time" while exerting the back-tracking phase takes on the order of (M+N) or "linear time," the matrix-filling phase can be a performance bottleneck when solving many local alignment problems. In that regard, H(j, k) can be computed via the following equations (1a)-(1c) for $0<j<=M$ and $0<k<=N$:

$$E(j, k) = \max \begin{cases} E(j-1, k) - \text{Gap Delete Extend} \\ H(j-1, k) - \text{Gap Delete Extend} \end{cases} \quad (1a)$$

$$F(j, k) = \max \begin{cases} F(j, k-1) - \text{Gap Insert Extend} \\ H(j, k-1) - \text{Gap Insert Open} \end{cases} \quad (1b)$$

$$H(j, k) = \max \begin{cases} 0 \\ E(j, k) \\ F(j, k) \\ H(j-1, k-1) - \text{Substitution } (T(j-1), Q(k-1)) \end{cases} \quad (1c)$$

In equations (1a)-(1c), E and F are matrices storing intermediate results for re-use in computing dependent sub-alignment scores. GapDeleteExtend, GapDeleteExtend, GapinsertOpen, and GapinsertExtend are "gap" constants; and Substitution(T(j−1), Q(k−1)) is a substitution value included in a substitution matrix that corresponds to a symbol match value (e.g., 4) or a symbol mismatch value (e.g., −1) for the symbols T(j−1) and Q(k−1).

Because of the vast number of computations that have to be executed during the matrix-filling phase for typically-sized DNA and protein sequences, some software applications accelerate the matrix-filling phase using sets of instructions or "programs" that execute on parallel processors. These types of processors can achieve very high computational throughputs by executing large numbers of threads in parallel across many different processing cores. One conventional approach to executing a Smith-Waterman matrix-filling phase on a parallel processor involves distributing the sub-alignment score computations associated with positions that can be computed independently of each other across groups of threads. Referring back to equations (1a)-(1c), H(j, k) depends on H(j−1, k−1) corresponding to the neighboring top-left diagonal position, E(j−1, k) and H(j−1, k) corresponding to the neighboring top position, and F(j, k−1) and H(j, k−1) corresponding to the neighboring left position. Consequently, the sub-alignment score computations along each anti-diagonal of the scoring matrix can be computed independently of each other. In an "anti-diagonal" implementation, the anti-diagonals of the scoring matrix are processed one-at-a-time, starting from the top left corner of the scoring matrix. To process each anti-diagonal, each position along the anti-diagonal is assigned to a different thread, and the threads compute the E, F, H, and substitution values corresponding to the assigned locations in parallel. The threads then write the E, F, and H values to the corresponding positions in an E matrix, an F matrix, and the scoring matrix, respectively, that are stored in shared memory.

One drawback of the above approach is that computational inefficiencies associated with each sub-alignment score can limit performance improvements attributable to parallelizing the overall matrix-filling phase. Computing each sub-alignment score involves sequentially executing ten instructions that include at least five addition/subtraction instructions and five two operand maximum instructions. Retrieving F values, E values, sub-alignment scores, and substitution values for the instruction calls to compute each sub-alignment score usually involves executing additional data movement instructions that reduce the computational throughput. Further, determining and storing the maximum sub-alignment score and associated position requires executing several instructions for each sub-alignment score. Because of the inefficiencies introduced by the additional instructions, the time required to execute the matrix-filling phase can be prohibitively long. For example, executing the matrix-filling phase for the human chromosome 21 that is 47 mega-basepairs (Mbp) long and the chimpanzee chromosome 22 that is 33 Mbp long can take nearly a day using the above approach.

As the foregoing illustrates, what is needed in the art are more effective techniques for executing the matrix-filling phase of the Smith-Waterman algorithm on parallel processors.

SUMMARY

One embodiment of the present invention sets forth a computer-implemented method for storing sub-alignment data when executing a matrix-filling phase of a Smith-Waterman algorithm. The method includes determining a top E value and a top sub-alignment score based on a top cell at a top position in a scoring matrix, where the scoring matrix is associated with at least a first target sequence and at least a first query sequence; computing a current E value that is associated with a current position in the scoring matrix based on the top E value and the top sub-alignment score; storing the current E value in a current cell at the current position in the scoring matrix; computing a current sub-alignment score that is associated with the current position in the scoring matrix based on the current E value, a diagonal sub-alignment score that is stored in a diagonal cell at a diagonal position in the scoring matrix, and a current substitution value that is associated with the first target sequence, the first query sequence, and the current position in the scoring matrix; and storing the current sub-alignment score in the current cell.

At least one technical advantage of the disclosed techniques relative to the prior art is that, with the disclosed techniques, the number of instructions executed to compute each sub-alignment score can be reduced when executing the matrix-filling phase of the Smith-Waterman algorithm using parallel processors. In that regard, with the disclosed techniques, a single Smith-Waterman instruction or a six-instruction Smith-Waterman sequence can be used to concurrently compute one, two, or four sub-alignment scores associated with one, two, or four different local alignment problems, respectively. Because sub-alignment scores and intermediate results associated with each position in the scoring matrix can be stored in an interleaved fashion within a single cell with the disclosed techniques, inefficiencies associated with data movement can be reduced relative to conventional techniques that retrieve the same data from separate matrices. Furthermore, with the disclosed techniques, an instruction that indicates the selected operand when determining the minimum or maximum of two operands can be used to reduce the number of instructions executed when determining and storing the maximum sub-alignment score and associated position. These technical advantages provide one or more technological improvements over prior art approaches.

BRIEF DESCRIPTION OF THE DRAWINGS

So that the manner in which the above recited features of the various embodiments can be understood in detail, a more particular description of the inventive concepts, briefly summarized above, may be had by reference to various embodiments, some of which are illustrated in the appended drawings. It is to be noted, however, that the appended drawings illustrate only typical embodiments of the inventive concepts and are therefore not to be considered limiting of scope in any way, and that there are other equally effective embodiments.

FIG. 9 is an example illustration of Smith-Waterman two problem pseudocode that is executed by the Smith-Waterman kernel of FIG. 1, according to various embodiments;

FIG. 10 is an example illustration of Smith-Waterman single problem pseudocode that is executed by the Smith-Waterman kernel of FIG. 1, according to other various embodiments;

FIG. 11 illustrates how the instructions of FIGS. 6 and 9 are implemented in execution units, according to various embodiments;

DETAILED DESCRIPTION

Figure 1:
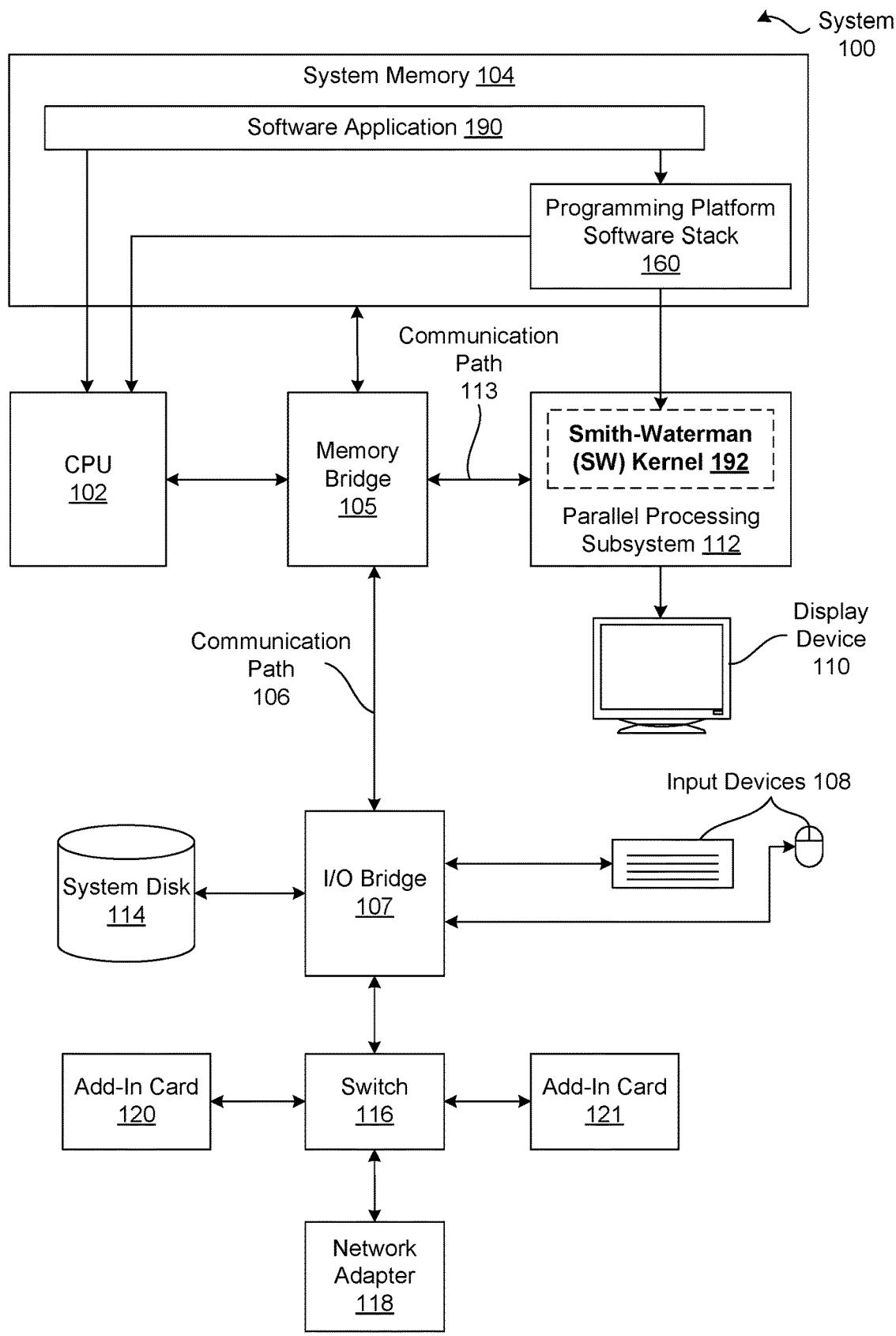
FIG. 1 is a block diagram illustrating a system configured to implement one or more aspects of the various embodiments.

In the following description, numerous specific details are set forth to provide a more thorough understanding of the various embodiments. However, it will be apparent to one skilled in the art that the inventive concepts may be practiced without one or more of these specific details. For explanatory purposes only, multiple instances of like objects are denoted herein with reference numbers identifying the object and parenthetical alphanumeric character(s) identifying the instance where needed.

As described previously herein, in one conventional approach to executing the matrix-filling phase of the Smith-Waterman algorithm on a parallel processor, a group of threads processes the anti-diagonals of a scoring matrix one-at-a-time, starting from the top left corner of a scoring matrix. To process each anti-diagonal, the group of threads concurrently compute sub-alignment data (e.g., an E value, an F value, a substitution value, and a sub-alignment score) for each position along the anti-diagonal. The group of threads stores the E values, the F values, and the sub-alignment scores in an E matrix, an F matrix, and the scoring matrix, respectively, that reside in shared memory.

One drawback of the above approach is that computational inefficiencies associated with each sub-alignment score can limit performance improvements attributable to parallelizing the overall matrix-filling phase. Computing the sub-alignment score involves executing data movement instructions to retrieve the requisite F value, E value, sub-alignment scores, and substitution value from shared memory, and then executing a sequence of ten instructions. Further, determining and storing the maximum sub-alignment score and associated position that are the outputs of the matrix-filling phase requires executing several instructions for each sub-alignment score. Because of the inefficiencies introduced by the additional instructions, the time required to execute the matrix-filling phase can be prohibitively long.

To address the above problems, in some embodiments, a software application 190 executing on a primary processor configures a group of threads to concurrently execute a Smith-Waterman (SW) kernel 192 on a parallel processor in order to perform a matrix-filling phase for one or more local alignment problems. The software application 190 is described in greater detail below in conjunction with FIG. 1.

The SW kernel 192 is a set of instructions (e.g., a program, a function, etc.) that can execute on the parallel processor. As described in detail below in conjunction with FIGS. 4, 5, and 13, in some embodiments, the SW kernel 192 implements one or more data interleaving techniques to reduce movement of sub-alignment data. In the same or other embodiments, the parallel processor implements one or more instructions that are specialized to increase computational efficiency when performing the matrix-filling phase, and the SW kernel 192 uses any number of the specialized instructions. In some embodiments, the SW kernel 192 uses a single specialized SW instruction or a sequence of six specialized instructions to compute sub-alignment scores. In the same or other embodiments, the SW kernel 192 uses a VIMNMX instruction that indicates the selected operand when selecting the minimum or maximum of two operands to reduce the number of instructions required to determine and store the maximum sub-alignment score and associated position. The SW instruction is described in detail below in conjunction with FIGS. 6, 9, and 14. The six-instruction sequence and the associated instructions are described in detail below in conjunction with FIGS. 7, 10, 11, and 15. The VIMNMX instruction is described in detail below in conjunction with FIGS. 8 and 11.

In some embodiments, to increase throughput, the group of threads executing the SW kernel 192 concurrently performs the matrix-filling phase for multiple alignment problems via a SIMD staggered thread technique. In the SIMD staggered thread technique, each thread in the warp performs row-by-row sub-alignment computations for a different sub-set of the columns, and each thread except thread 0 is one row behind the immediately lower thread with respect to sub-alignment computations. For instance, in some embodiments, during an initial iteration, thread 0 performs sub-alignment computations corresponding to H(1, 1)-H(1, C) for P local alignment problems, where C and P can be any positive integers. During the next iteration, thread 0 performs sub-alignment computations corresponding to H(2, 1)-H(2, C), for the P local alignment problems, and thread 1 performs sub-alignment computations corresponding to H(1, C+1)-H(1, 2C) for the P local alignment problems.

For explanatory purposes only, the functionality of the software application 190 and the SW kernel 192 are described below in conjunction with FIGS. 1-16 in the context of determining, without limitation, a maximum sub-alignment score and the position of the maximum sub-alignment score in the scoring matrix for each of any number of local sequence alignment problems. In some embodiments, the SW kernel 192 does not preserve the scoring matrix. For instance, in some embodiments, at most two rows of the scoring matrix are stored in memory at any given time.

In some embodiments, for each maximum sub-alignment score that exceeds a match threshold, the software application 190 causes the SW kernel 192 to generate a traceback matrix while re-executing the matrix-filling phase for the corresponding local alignment problem. The traceback matrix specifies the position from which each sub-alignment score is derived and therefore can be used to determine the optimized local alignment.

In some other embodiments, for each maximum sub-alignment score that exceeds a match threshold, the software application 190 reverses the corresponding target sequence and the corresponding query sequence. The software application then causes the SW kernel 192 to re-execute the matrix-filling phase based on the reversed sequences. The position(s) of the maximum sub-alignment score corresponds to the starting position within the scoring matrix that correspond to the maximum sub-alignment score and can be used to determine the optimized local alignment.

Note that the techniques described herein are illustrative rather than restrictive and can be altered without departing from the broader spirit and scope of the invention. Many modifications and variations on the functionality provided by the software application 190, the SW kernel 192, the warp, the parallel processing subsystem 112, the PPUs, the SMs, and the CPU will be apparent to those of ordinary skill in the art without departing from the scope and spirit of the described embodiments.

Exemplary System Overview

For explanatory purposes only, the functionality of the software application 190 and the SW kernel 192 are described below in conjunction with FIGS. 1-16 in the context of some embodiments that are implemented within a system 100. As described in greater detail below, in the embodiments depicted in FIGS. 1-16, the software application 190 executes on a CPU 102 and causes a group of threads to concurrently execute the SW kernel 192 on one or more streaming multiprocessors (SMs).

FIG. 1 is a block diagram illustrating a system 100 configured to implement one or more aspects of the various embodiments. As shown, the system 100 includes, without limitation, the CPU 102 and a system memory 104 coupled to a parallel processing subsystem 112 via a memory bridge 105 and a communication path 113. In some embodiments, at least a portion of the system memory 104 is host memory associated with the CPU 102. The memory bridge 105 is further coupled to an input/output (I/O) bridge 107 via a communication path 106, and the I/O bridge 107 is, in turn, coupled to a switch 116.

In operation, the I/O bridge 107 is configured to receive user input information from input devices 108, such as a keyboard or a mouse, and forward the input information to the CPU 102 for processing via the communication path 106 and the memory bridge 105. The switch 116 is configured to provide connections between the I/O bridge 107 and other components of the system 100, such as a network adapter 118 and add-in cards 120 and 121.

As also shown, the I/O bridge 107 is coupled to a system disk 114 that can be configured to store content, applications, and data for use by the CPU 102 and the parallel processing subsystem 112. As a general matter, the system disk 114 provides non-volatile storage for applications and data and can include fixed or removable hard disk drives, flash memory devices, compact disc read-only memory, digital versatile disc read-only memory, Blu-ray, high definition digital versatile disc, or other magnetic, optical, or solid-state storage devices. Finally, although not explicitly shown, other components, such as a universal serial bus or other port connections, compact disc drives, digital versatile disc drives, film recording devices, and the like, can be connected to the I/O bridge 107 as well.

In various embodiments, the memory bridge 105 can be a Northbridge chip, and the I/O bridge 107 can be a Southbridge chip. In addition, the communication paths 106 and 113, as well as other communication paths within the system 100, can be implemented using any technically suitable protocols, including, without limitation, Peripheral Component Interconnect Express, Accelerated Graphics Port, HyperTransport, or any other bus or point-to-point communication protocol known in the art.

In some embodiments, the parallel processing subsystem 112 includes, without limitation, one or more parallel processors. In some embodiments, each parallel processor is a PPU that includes, without limitation, one or more SMs. Each SM includes, without limitation, multiple execution units also referred to herein as "processor cores". In some embodiments, the PPUs can be identical or different, and each PPU can be associated with dedicated parallel processing (PP) memory or no dedicated PP memory. In some embodiments, the PP memory associated with a given PPU is also referred to as the "device memory" associated with the PPU. In the same or other embodiments, each kernel that is launched on a given PPU resides in the device memory of the PPU.

In some embodiments, the parallel processing subsystem 112 incorporates circuitry optimized for general-purpose processing. As described in greater detail below in conjunction with FIG. 2, such circuitry can be incorporated across one or more PPUs that can be configured to perform general-purpose processing operations. In the same or other embodiments, the parallel processing subsystem 112 further incorporates circuitry optimized for graphics processing. Such circuitry can be incorporated across one or more PPUs that can be configured to perform graphics processing operations. In the same or other embodiments, any number of PPUs can output data to any number of display devices 110. In some embodiments, zero or more of the PPUs can be configured to perform general-purpose processing operations but not graphics processing operations, zero or more of the PPUs can be configured to perform graphics processing operations but not general-purpose processing operations, and zero or more of the PPUs can be configured to perform general-purpose processing operations and/or graphics processing operations. In some embodiments, software applications executing under the control of the CPU 102 can launch kernels on one or more PPUs.

In some embodiments, the parallel processing subsystem 112 can be integrated with one or more other elements of FIG. 1 to form a single system. For example, the parallel processing subsystem 112 can be integrated with the CPU 102 and other connection circuitry on a single chip to form a system on a chip. In the same or other embodiments, any number of CPUs 102 and any number of parallel processing subsystems 112 can be distributed across any number of shared geographic locations and/or any number of different geographic locations and/or implemented in one or more cloud computing environments (i.e., encapsulated shared resources, software, data, etc.) in any combination.

The system memory 104 can include, without limitation, any amount and/or types of system software (e.g., operating systems, device drivers, library programs, utility programs, etc.), any number and/or types of software applications, or any combination thereof. The system software and the software applications included in the system memory 104 can be organized in any technically feasible fashion.

As shown, in some embodiments, the system memory 104 includes, without limitation, a programming platform software stack 160 and the software application 190. The programming platform software stack 160 is associated with a programming platform for leveraging hardware in the parallel processing subsystem 112 to accelerate computational tasks. In some embodiments, the programming platform is accessible to software developers through, without limitation, libraries, compiler directives, and/or extensions to programming languages. In the same or other embodiments, the programming platform can be, but is not limited to, Compute Unified Device Architecture (CUDA) (CUDA® is developed by NVIDIA Corporation of Santa Clara, CA), Radeon Open Compute Platform (ROCm), OpenCL (OpenCL™ is developed by Khronos group), SYCL, or Intel One API.

In some embodiments, the programming platform software stack 160 provides an execution environment for the software application 190 and zero or more other software applications (not shown). In some embodiments, the software application 190 can be any type of software application (e.g., a genomics application) that resides in any number and/or types of memories and executes any number and/or types of instructions on the CPU 102 and/or any number and/or types of instructions on the parallel processing subsystem 112. In some embodiments, the software application 190 executes any number and/or types of instructions associated with any number of local sequence alignments. In the same or other embodiments, the software application 190 can execute any number and/or types of instructions on the parallel processing subsystem 112 in any technically feasible fashion. For instance, in some embodiments, the software application 190 can include, without limitation, any computer software capable of being launched on the programming platform software stack 160.

In some embodiments, the software application 190 and the programming platform software stack 160 execute under the control of the CPU 102. In the same or other embodiments, the software application 190 can access one or more PPUs included in the parallel processing subsystem 112 via the programming platform software stack 160. In some embodiments, the programming platform software stack 160 includes, without limitation, any number and/or types of libraries (not shown), any number and/or types of runtimes (not shown), any number and/or types of drivers (not shown), or any combination thereof.

In some embodiments, each library can include, without limitation, data and programming code that can be used by computer programs (e.g., the software application 190, the SW kernel 192, etc.) and leveraged during software development. In the same or other embodiments, each library can include, without limitation, pre-written code, kernels, subroutines, functions, macros, any number and/or types of other sets of instructions, or any combination thereof that are optimized for execution on one or more SMs within the parallel processing subsystem 112. In the same or other embodiments, libraries included in the programming platform software stack 160 can include, without limitation, classes, values, type specifications, configuration data, documentation, or any combination thereof. In some embodiments, the libraries are associated with one or more application programming interfaces (API) that expose at least a portion of the content implemented in the libraries.

Although not shown, in some embodiments, one or more SW libraries can include, without limitation, pre-written code, kernels (including the SW kernel 192), subroutines, functions, macros, any number and/or types of other sets of instructions, classes, values, type specifications, configuration data, documentation, or any combination thereof that are optimized for execution on one or more SMs within the parallel processing subsystem 112.

In some embodiments, at least one device driver is configured to manage the processing operations of the one or more PPUs within the parallel processing subsystem 112. In the same or other embodiments, any number of device drivers implement API functionality that enables software applications to specify instructions for execution on the one or more PPUs via API calls. In some embodiments, any number of device drivers provide compilation functionality for generating machine code specifically optimized for the parallel processing subsystem 112.

In the same or other embodiments, at least one runtime includes, without limitation, any technically feasible runtime system that can support execution of the software application 190 and zero or more other software applications. In some embodiments, the runtime is implemented as one or more libraries associated with one or more runtime APIs. In the same or other embodiments, one or more drivers are implemented as libraries that are associated with driver APIs.

In some embodiments, one or more runtime APIs and/or one or more driver API scan expose, without limitation, any number of functions for each of memory management, execution control, device management, error handling, and synchronization, and the like. The memory management functions can include, but are not limited to, functions to allocate, deallocate, and copy device memory, as well as transfer data between host memory and device memory. The execution control functions can include, but are not limited to, functions to launch kernels on PPUs included in the parallel processing subsystems 112. In some embodiments, relative to the runtime API(s), the driver API(s) are lower-level APIs that provide more fine-grained control of the PPUs.

In the same or other embodiments, a parallel runtime enables software applications to dispatch groups of threads across one or more SMs. Each of the software applications can reside in any number of memories and execute on any number of processors in any combination. Some examples of processors include, without limitation, the CPU 102, the parallel processing subsystem 112, and the PPUs. In some embodiments, software applications executing under the control of the CPU 102 can launch kernels on one or more PPUs.

The software application 190 can call any number and/or types of functions to configure a group of threads to concurrently perform the matrix-filling phase of a SW algorithm for one or more local alignment problems. In some embodiments, each local alignment problem is associated with a target sequence, a query sequence, a set of constants, and a substitution matrix. In some embodiments, each of the target sequence, the query sequence, the length of the target sequence, the length of the query sequence, the set of constants, and the substitution matrix associated with one local sequence alignment problem can be same as or different from the target sequence, the query sequence, the length of the target sequence, the length of the query sequence, the set of constants, and the substitution matrix, respectively, associated with each of the other local sequence alignment problems. For explanatory purposes only, the target sequence(s), the query sequence(s), the set(s) of constants, and the substitution matrix(s) are also referred to herein as "SW input data."

In some embodiments, for each local alignment problem, the result of the matrix-filling phase of the SW algorithm is a maximum sub-alignment score and a maximum scoring position (e.g., a row index and a column index) within an associated scoring matrix. In the same or other embodiments, only a portion of the scoring matrix is stored in memory at any given time. For example, in some embodiments, only two rows of the scoring matrix are stored in memory at any given time. In some embodiments, one, two, or four local alignment problems share each scoring matrix.

In some embodiments, to configure a group of threads to concurrently perform the matrix-filling phase, the software application 190 selects the SW kernel 192 from one or more SW kernels that are each associated with different characteristics based on any number and/or types of criteria. For instance, in some embodiments, some SW kernels use a single SW instruction to compute sub-alignment data and some other SW kernels use a sequence of six instructions to compute sub-alignment data. In some embodiments, some SW kernels implement a SIMD staggered thread technique to partition each local alignment problem between multiple threads. In the same or other embodiments, some SW kernels assign each local alignment problem to a single thread. In some embodiments, the type of the input data (e.g., unsigned 32-bit integer, signed 32-bit integer, etc.) varies across the SW kernels.

In some embodiments, the software application 190 allocates device memory for the storage of the target sequence (s), the query sequence(s), the set of constants, the substitution matrix, and the result(s). The software application 190 then copies the target sequence(s), the query sequence(s), the set of constants, and the substitution matrix from host memory to device memory. The software application 190 can organize the target sequence(s), the query sequence(s), the set(s) of constants, the substitution matrix(s), and the result(s) in any technically feasible fashion to optimize memory accesses by the SW kernel 192.

In the same or other embodiments, the software application 190 invokes or "launches" the SW kernel 192 via a kernel invocation (not shown). The kernel invocation includes, without limitation, the name of the SW kernel 192, an execution configuration (not shown), and argument values (not shown) for the arguments of the SW kernel 192. In some embodiments, the execution configuration specifies, without limitation, a configuration (e.g., size, dimensions, etc.) of a group of threads. The group of threads can be organized in any technically feasible fashion and the configuration of the group of threads can be specified in any technically feasible fashion.

For instance, in some embodiments, the group of threads is organized as a grid of cooperative thread arrays (CTAs), and the execution configuration specifies, without limitation, a single dimensional or multi-dimensional grid size and a single dimensional or multi-dimensional CTA size. Each thread in the grid of CTAs is configured to execute the SW kernel 192 on different input data. More specifically, in some embodiments, each PPU is configured to concurrently process one or more grids of CTAs, and each CTA in a grid concurrently executes the same program on different input data. In the same or other embodiments, each SM is configured to concurrently process one or more CTAs. Each CTA is also referred to as a "thread block." In some embodiments, each SM breaks each CTA into one or more groups of parallel threads referred to as "warps" that the SM creates, manages, schedules, and executes in a single instruction, multiple thread (SIMT) fashion. In some embodiments, each warp includes, without limitation, a fixed-number of threads (e.g., 32). Each warp in a CTA concurrently executes the same program on different input data, and each thread in a warp concurrently executes the same program on different input data. In some embodiments, the threads in a warp can diverge and re-converge during execution.

The grid size and the CTA size can be determined in any technically feasible fashion based on any amount and/or types of criteria. In some embodiments, the software application 190 determines the grid size and the CTA size based on the dimensions of the SW input data and the amounts of hardware resources, such as memory or registers, available to the grid and the CTAs. In the same or other embodiments, the software application 190, the SW kernel 192, or both determine any amount and/or types of problem configuration data associated with the SW kernels 192 based on the grid size, the CTA size, the dimensions of the SW input data, or any combination thereof. For example, the number of columns assigned to each thread when the SW kernel 192 implements a SIMD staggered thread matrix-filling technique can be determined based on register pressure. For example, to avoid register spilling, the number of columns assigned to each thread can be reduced.

Note that the techniques described herein are illustrative rather than restrictive and may be altered without departing from the broader spirit and scope of the invention. Many modifications and variations on the functionality provided by the system 100, the CPU 102, the parallel processing subsystem 112, the software application 190, the SW kernel 192, the programming platform software stack 160, zero or more libraries, zero or more drivers, and zero or more runtimes will be apparent to those of ordinary skill in the art without departing from the scope and spirit of the described embodiments.

It will be appreciated that the system shown herein is illustrative and that variations and modifications are possible. The connection topology, including the number and arrangement of bridges, the number of the CPUs 102, and the number of the parallel processing subsystems 112, can be modified as desired. For example, in some embodiments, the system memory 104 can be connected to the CPU 102 directly rather than through the memory bridge 105, and other devices can communicate with the system memory 104 via the memory bridge 105 and the CPU 102. In other alternative topologies, the parallel processing subsystem 112 can be connected to the I/O bridge 107 or directly to the CPU 102, rather than to the memory bridge 105. In still other embodiments, the I/O bridge 107 and the memory bridge 105 can be integrated into a single chip instead of existing as one or more discrete devices. Lastly, in certain embodiments, one or more components shown in FIG. 1 may not be present. For example, the switch 116 could be eliminated, and the network adapter 118 and the add-in cards 120, 121 would connect directly to the I/O bridge 107.

As described previously herein, in some embodiments, any software application executing on any primary processor can configure a group of threads to concurrently execute the SW kernel 192 on a parallel processor in order to perform a matrix-filling phase for one or more local alignment problems. As referred to herein, a "processor" can be any instruction execution system, apparatus, or device capable of executing instructions. For explanatory purposes, the terms "function" and "program" are both used herein to refer to any set of one or more instructions that can be executed by any number and/or types of processors. Furthermore, the term "kernel" is used to refer to a set of instructions (e.g., a program, a function, etc.) that can execute on one or more parallel processors.

As referred to herein, a "parallel processor" can be any computing system that includes, without limitation, multiple parallel processing elements that can be configured to perform any number and/or types of computations. And a "parallel processing element" of a computing system is a physical unit of simultaneous execution in the computing system. In some embodiments, the parallel processor can be a parallel processing unit (PPU), a graphics processing unit (GPU), a tensor processing unit, a multi-core central processing unit (CPU), an intelligence processing unit, a neural processing unit, a neural network processor, a data processing unit, a vision processing unit, or any other type of processor or accelerator that can presently or in the future support parallel execution of multiple threads.

As referred to herein, a "primary processor" can be any type of parallel processor or any type of other processor that is capable of launching kernels on a parallel processor. In some embodiments, the primary processor is a latency-optimized general-purpose processor, such as a CPU. In some embodiments, the software application 190 executes on a parallel processor and can configure a group of threads executing on the parallel processor to implement any number of the techniques described herein with respect to the SW kernel 192 in any technically feasible fashion.

Figure 2:
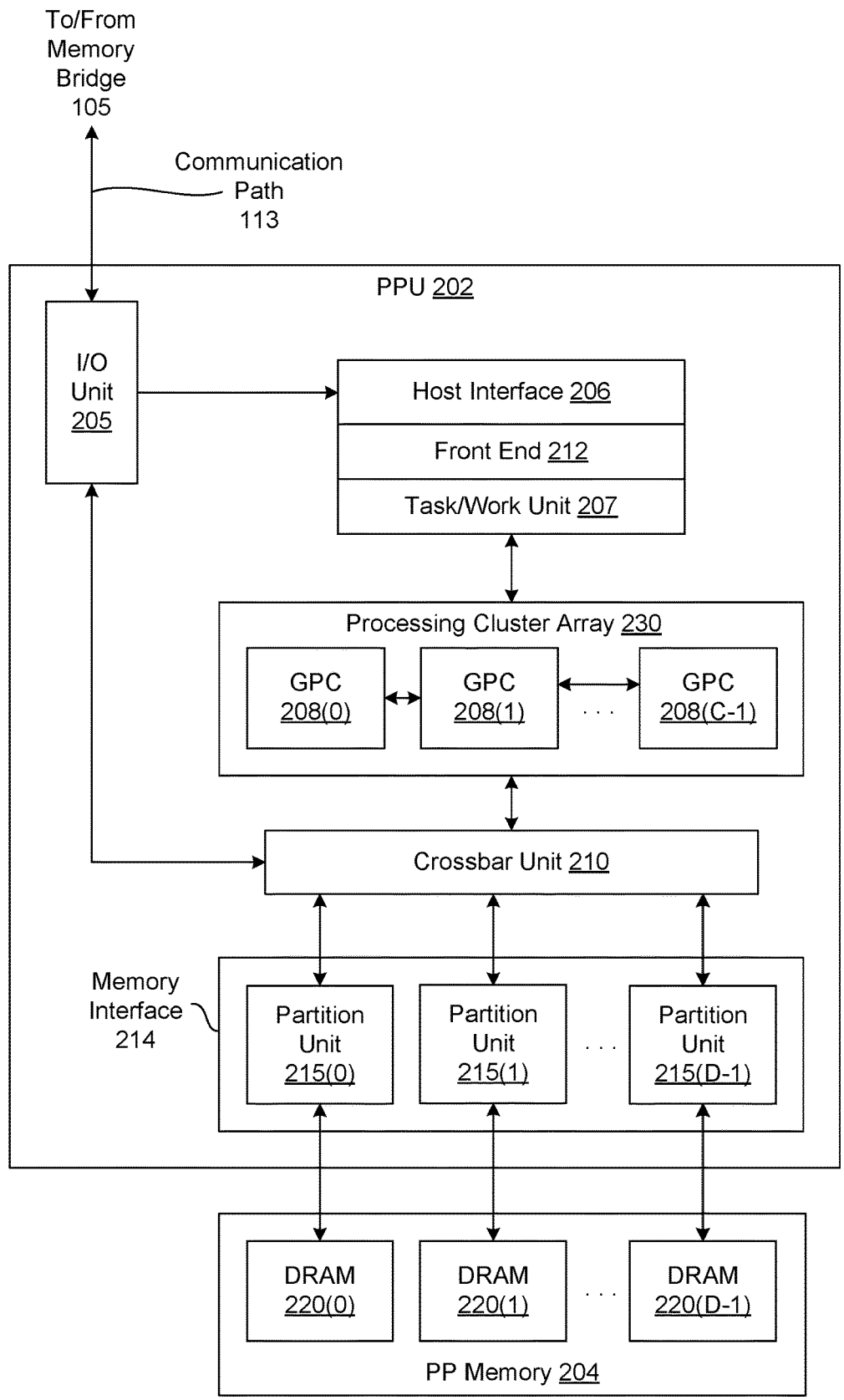
FIG. 2 is a block diagram of a parallel processing unit included in the parallel processing subsystem of FIG. 1, according to various embodiments.

FIG. 2 is a block diagram of a PPU 202 included in the parallel processing subsystem 112 of FIG. 1, according to various embodiments. Although FIG. 2 depicts one PPU 202, as indicated above, the parallel processing subsystem 112 can include zero or more other PPUs that are identical to the PPUs 202 and zero or more other PPUs that are different from the PPU 202. As shown, the PPU 202 is coupled to a local parallel processing (PP) memory 204. The PPU 202 and the PP memory 204 can be implemented using one or more integrated circuit devices, such as programmable processors, application specific integrated circuits, or memory devices, or in any other technically feasible fashion.

As shown, the PPU 202 incorporates circuitry optimized for general purpose processing, and the PPU 202 can be configured to perform general purpose processing operations. Although not shown in FIG. 2, in some embodiments, the PPU 202 further incorporates circuitry optimized for graphics processing, including, for example, video output circuitry. In such embodiments, the PPU 202 can be configured to perform general purpose processing operations and/or graphics processing operations.

Referring again to FIG. 1 as well as FIG. 2, in some embodiments, the CPU 102 is the master processor of the system 100, controlling and coordinating operations of other system components. In particular, the CPU 102 issues commands that control the operation of the PPU 202. In some embodiments, the CPU 102 writes a stream of commands for the PPU 202 to a data structure (not explicitly shown in either FIG. 1 or FIG. 2) that can be located in the system memory 104, the PP memory 204, or another storage location accessible to both the CPU 102 and the PPU 202. A pointer to the data structure is written to a pushbuffer to initiate processing of the stream of commands in the data structure. The PPU 202 reads command streams from the pushbuffer and then executes commands asynchronously relative to the operation of the CPU 102. In embodiments where multiple pushbuffers are generated, execution priorities can be specified for each pushbuffer by an application program via a device driver (not shown) to control scheduling of the different pushbuffers.

Referring back now to FIG. 2 as well as FIG. 1, in some embodiments, the PPU 202 includes an I/O unit 205 that communicates with the rest of system 100 via the communication path 113, which connects to memory bridge 105. In some other embodiments, the I/O unit 205 communicates with the rest of system 100 via the communication path 113, which connects directly to CPU 102. In the same or other embodiments, the connection of the PPU 202 to the rest of the system 100 can be varied. In some embodiments, the parallel processing subsystem 112, which includes at least one PPU 202, is implemented as an add-in card that can be inserted into an expansion slot of the system 100. In some other embodiments, the PPU 202 can be integrated on a single chip with a bus bridge, such as the memory bridge 105 or the I/O bridge 107. In some other embodiments, some or all of the elements of the PPU 202 can be included along with the CPU 102 in a single integrated circuit or system on a chip.

The I/O unit 205 generates packets (or other signals) for transmission on the communication path 113 and also receives all incoming packets (or other signals) from the communication path 113, directing the incoming packets to appropriate components of the PPU 202. For example, commands related to processing tasks can be directed to a host interface 206, while commands related to memory operations (e.g., reading from or writing to the PP memory 204) can be directed to a crossbar unit 210. The host interface 206 reads each pushbuffer and transmits the command stream stored in the pushbuffer to a front end 212.

In operation, the front end 212 transmits processing tasks received from the host interface 206 to a work distribution unit (not shown) within a task/work unit 207. The work distribution unit receives pointers to processing tasks that are encoded as task metadata (TMD) and stored in memory. The pointers to TMDs are included in a command stream that is stored as a pushbuffer and received by the front end 212 from the host interface 206. Processing tasks that can be encoded as TMDs include indices associated with the data to be processed as well as state parameters and commands that define how the data is to be processed. For example, the state parameters and commands could define the program to be executed on the data.

The PPU 202 advantageously implements a highly parallel processing architecture based on a processing cluster array 230 that includes a set of C GPCs 208, where C 1. Each of the GPCs 208 is capable of executing a large number (e.g., hundreds or thousands) of threads concurrently, where each thread is an instance of a program (e.g., a kernel). In various applications, different GPCs 208 can be allocated for processing different types of programs or for performing different types of computations. The allocation of the GPCs 208 can vary depending on the workload arising for each type of program or computation. The GPCs 208 receive processing tasks to be executed from the work distribution unit within the task/work unit 207.

The task/work unit 207 receives processing tasks from the front end 212 and ensures that general processing clusters (GPCs) 208 are configured to a valid state before the processing task specified by each one of the TMDs is initiated. A priority can be specified for each TMD that is used to schedule the execution of the processing task. Processing tasks also can be received from the processing cluster array 230. Optionally, the TMD can include a parameter that controls whether the TMD is added to the head or the tail of a list of processing tasks (or to a list of pointers to the processing tasks), thereby providing another level of control over execution priority.

Memory interface 214 includes a set of D partition units 215, where D≥1. Each of the partition units 215 is coupled to one or more dynamic random access memories (DRAMs) 220 residing within the PP memory 204. In some embodiments, the number of the partition units 215 equals the number of the DRAMs 220, and each of the partition units 215 is coupled to a different one of the DRAMs 220. In some other embodiments, the number of the partition units 215 can be different than the number of the DRAMs 220. Persons of ordinary skill in the art will appreciate that the DRAM 220 can be replaced with any other technically suitable storage device. In operation, various targets can be stored across the DRAMs 220, allowing the partition units 215 to write portions of each target in parallel to efficiently use the available bandwidth of the PP memory 204.

A given GPC 208 can process data to be written to any of the DRAMs 220 within the PP memory 204. The crossbar unit 210 is configured to route the output of each GPC 208 to the input of any partition unit 215 or to any other GPC 208 for further processing. The GPCs 208 communicate with the memory interface 214 via the crossbar unit 210 to read from or write to any number of the DRAMs 220. In some embodiments, the crossbar unit 210 has a connection to the I/O unit 205 in addition to a connection to the PP memory 204 via the memory interface 214, thereby enabling the SMs within the different GPCs 208 to communicate with the system memory 104 or other memory not local to the PPU 202. In the embodiment of FIG. 2, the crossbar unit 210 is directly connected with the I/O unit 205. In various embodiments, the crossbar unit 210 can use virtual channels to separate traffic streams between the GPCs 208 and the partition units 215.

Again, the GPCs 208 can be programmed to execute processing tasks relating to a wide variety of applications and/or algorithms. In some embodiments, the PPU 202 is configured to transfer data from the system memory 104 and/or the PP memory 204 to one or more on-chip memory units, process the data, and write result data back to the system memory 104 and/or the PP memory 204. The result data can then be accessed by other system components, including the CPU 102, another PPU 202 within the parallel processing subsystem 112, or another parallel processing subsystem 112 within the system 100.

As noted above, any number of the PPUs 202 can be included in the parallel processing subsystem 112. For example, multiple PPUs 202 can be provided on a single add-in card, or multiple add-in cards can be connected to the communication path 113, or one or more of the PPUs 202 can be integrated into a bridge chip. The PPUs 202 in a multi-PPU system can be identical to or different from one another. For example, different PPUs 202 might have different numbers of processor cores and/or different amounts of the PP memory 204. In implementations where multiple PPUs 202 are present, those PPUs 202 can be operated in parallel to process data at a higher throughput than is possible with a single PPU 202. Systems incorporating one or more PPUs 202 can be implemented in a variety of configurations and form factors, including, without limitation, desktops, laptops, handheld personal computers or other handheld devices, servers, workstations, game consoles, embedded systems, and the like.

Figure 3A:
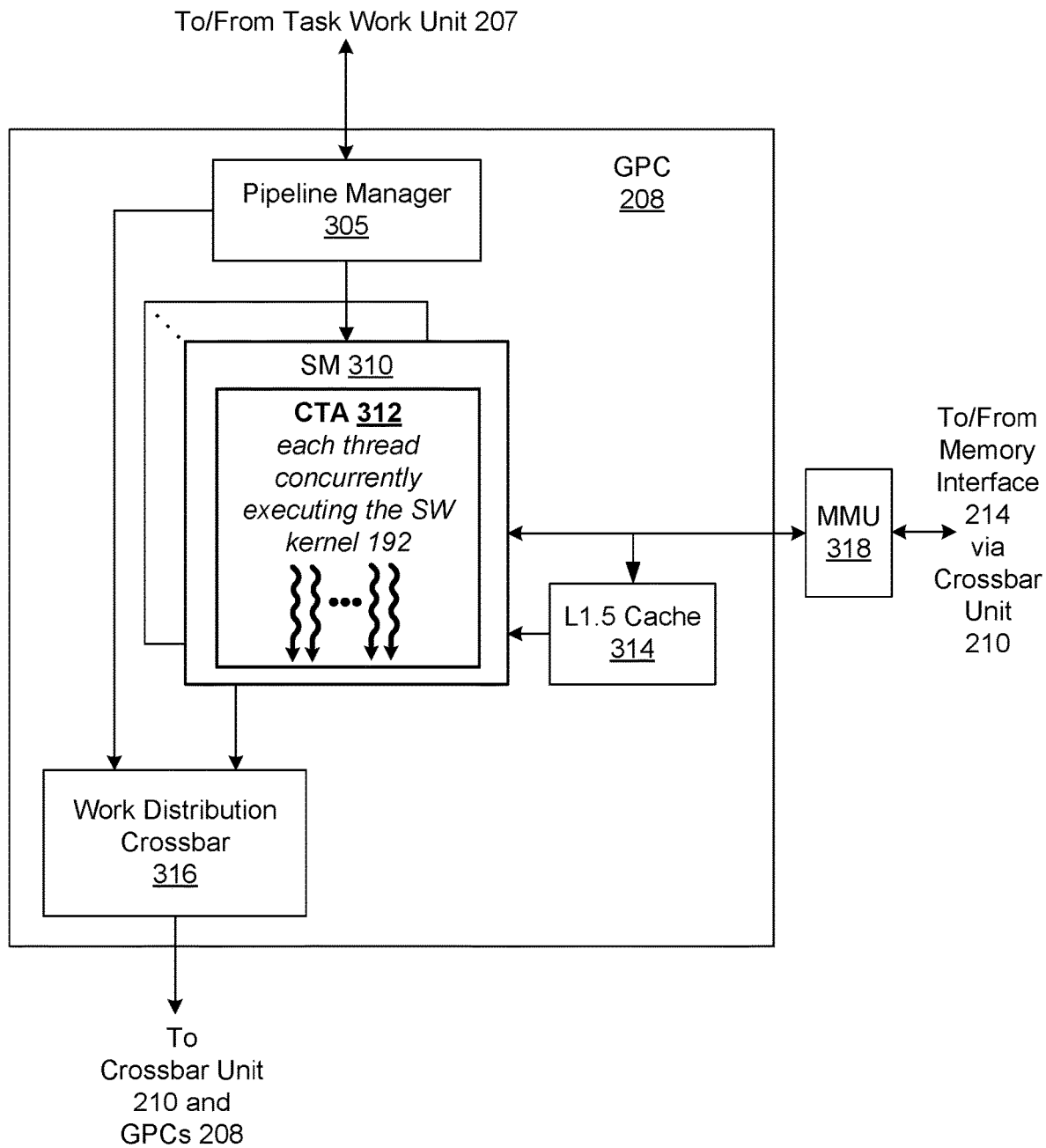
FIG. 3A is a block diagram of a general processing cluster included in the parallel processing unit of FIG. 2, according to various embodiments.

FIG. 3A is a block diagram of a GPC 208 included in the PPU 202 of FIG. 2, according to various embodiments. In operation, the GPC 208 can be configured to execute a large number of threads in parallel. In some embodiments, each thread executing on the GPC 208 is an instance of a particular program executing on a particular set of input data. In some embodiments, single-instruction, multiple-data (SIMD) instruction issue techniques are used to support parallel execution of a large number of threads without providing multiple independent instruction units. In some other embodiments, SIMT techniques are used to support parallel execution of a large number of generally synchronized threads, using a common instruction unit configured to issue instructions to a set of processing engines within the GPC 208. Unlike a SIMD execution regime, where all processing engines typically execute identical instructions, SIMT execution allows different threads to more readily follow divergent execution paths through a given program. Persons of ordinary skill in the art will understand that a SIMD processing regime represents a functional subset of a SIMT processing regime.

Operation of the GPC 208 is controlled via a pipeline manager 305 that distributes processing tasks received from the work distribution unit (not shown) within the task/work unit 207 to one or more SMs 310. The pipeline manager 305 can also be configured to control a work distribution crossbar 316 by specifying destinations for processed data output by the SMs 310.

In some embodiments, the GPC 208 includes, without limitation, a number M of SMs 310, where M≥1. In the same or other embodiments, each of the SMs 310 includes, without limitation, a set of execution units (not shown in FIG. 3A). Processing operations specific to any of the execution units can be pipelined, which enables a new instruction to be issued for execution before a previous instruction has completed execution. Any combination of execution units within a given SM 310 can be provided. In various embodiments, the execution units can be configured to support a variety of different operations including integer and floating point arithmetic (e.g., addition and multiplication), comparison operations, Boolean operations (e.g., AND, OR, XOR), bit-shifting, and computation of various algebraic functions (e.g., planar interpolation and trigonometric, exponential, and logarithmic functions, etc.). Advantageously, the same execution unit can be configured to perform different operations.

As described previously herein, in some embodiments, each SM 310 is configured to process one or more warps. In some embodiments, the SM 310 can issue and execute warp-level instructions. In particular, in some embodiments, the SM 310 can issue and execute warp shuffle instructions (e.g., SHFL_SYNC) that enable direct register-to-register data exchange between the threads in a warp.

In some embodiments, multiple related warps included in a CTA 312 can be active (in different phases of execution) at the same time within the SM 310. In the same or other embodiments, the size of the CTA 312 is equal to m*k, where k is the number of concurrently executing threads in a warp, which is typically an integer multiple of the number of execution units within the SM 310, and m is the number of warps simultaneously active within the SM 310. In some embodiments, each CTA 312 can be a single thread, a single-dimensional array of threads, or a multi-dimensional block of threads that is configured to concurrently execute the same program on different input data. In the same or other embodiments, each of the SMs 310 can concurrently process a maximum number of CTAs 312 (e.g., one, two, etc.) that is dependent on the size of the CTAs 312.

In some embodiments, each thread in each CTA 312 is assigned a unique thread identifier (ID) that is accessible to the thread during execution. The thread ID, which can be defined as a one-dimensional or multi-dimensional numerical value controls various aspects of the thread's processing behavior. For instance, a thread ID may be used to determine which portion of the input dataset a thread is to process and/or to determine which portion of an output dataset a thread is to produce or write. In some embodiments, each thread in CTA 312 has access to a portion of the shared memory that is allocated to CTA 312. In the same or other embodiments, the threads in each CTA 312 can synchronize together, collaborate, communicate, or any combination thereof in any technically feasible fashion (e.g., via a shared memory).

As described previously herein in conjunction with FIG. 1, in some embodiments, CTAs 312 that are configured to execute the same kernel are organized into a single dimensional or multi-dimensional grid. In the same or other embodiments, each CTA 312 is assigned a unique CTA ID that is accessible to each thread in the CTA 312 during the thread's execution.

Referring back to FIG. 2 as well as FIG. 3A, in some embodiments, each CTA 312 in a given grid is scheduled onto one of the SMs 310 included in PPU 202. Subsequently, the threads in each CTA 312 concurrently execute the same program on different input data, with each thread in the CTA 312 executing on a different execution unit within the SM 310 that the CTA 312 is scheduled onto.

In some embodiments, each of the SMs 310 contains a level one (L1) cache (not shown in FIG. 3A) or uses space in a corresponding L1 cache outside of the SM 310 to support, among other things, load and store operations. Each of the SMs 310 also has access to level two (L2) caches (not shown) that are shared among all the GPCs 208 in the PPU 202. In some embodiments, the L2 caches can be used to transfer data between threads. Finally, the SMs 310 also have access to off-chip "global" memory, which can include the PP memory 204 and/or the system memory 104. It is to be understood that any memory external to the PPU 202 can be used as global memory. Additionally, as shown in FIG. 3A, a level one-point-five (L1.5) cache 314 can be included within the GPC 208 and configured to receive and hold data requested from memory via the memory interface 214 by the SM 310 and provide the requested data to the SM 310. Such data can include, without limitation, instructions, uniform data, and constant data. In embodiments having multiple SMs 310 within the GPC 208, the SMs 310 can beneficially share common instructions and data cached in the L1.5 cache 314.

Each GPC 208 can have an associated memory management unit (MMU) 318 that is configured to map virtual addresses into physical addresses. In various embodiments, the MMU 318 can reside either within the GPC 208 or within the memory interface 214. The MMU 318 includes a set of page table entries used to map a virtual address to a physical address of a tile or memory page and optionally a cache line index. The MMU 318 can include address translation lookaside buffers or caches that can reside within the SMs 310, within one or more L1 caches, or within the GPC 208.

In some embodiments, each SMs 310 transmits a processed task to the work distribution crossbar 316 in order to provide the processed task to another GPC 208 for further processing or to store the processed task in an L2 cache (not shown), the PP memory 204, or the system memory 104 via the crossbar unit 210.

It will be appreciated that the core architecture described herein is illustrative and that variations and modifications are possible. Among other things, any number and/or types of processing units, such as the SMs 310, can be included within the GPC 208. Further, as described above in conjunction with FIG. 2, the PPU 202 can include any number of the GPCs 208 that are configured to be functionally similar to one another so that execution behavior does not depend on which of the GPCs 208 receives a particular processing task. Further, in some embodiments, each of the GPCs 208 operates independently of the other GPCs 208 in the PPU 202 to execute tasks for one or more application programs. In view of the foregoing, persons of ordinary skill in the art will appreciate that the architecture described in FIGS. 1-3 in no way limits the scope of the present disclosure.

As shown in italics for the CTA 312, in some embodiments, each thread in one or more CTAs 312 concurrently executes the SW kernel 192. The CTAs 312 can be configured to execute the SW kernel 192 in any technically feasible fashion. Further, the CTAs 312 can be scheduled onto the SMs 310 in any technically feasible fashion.

Figure 3B:
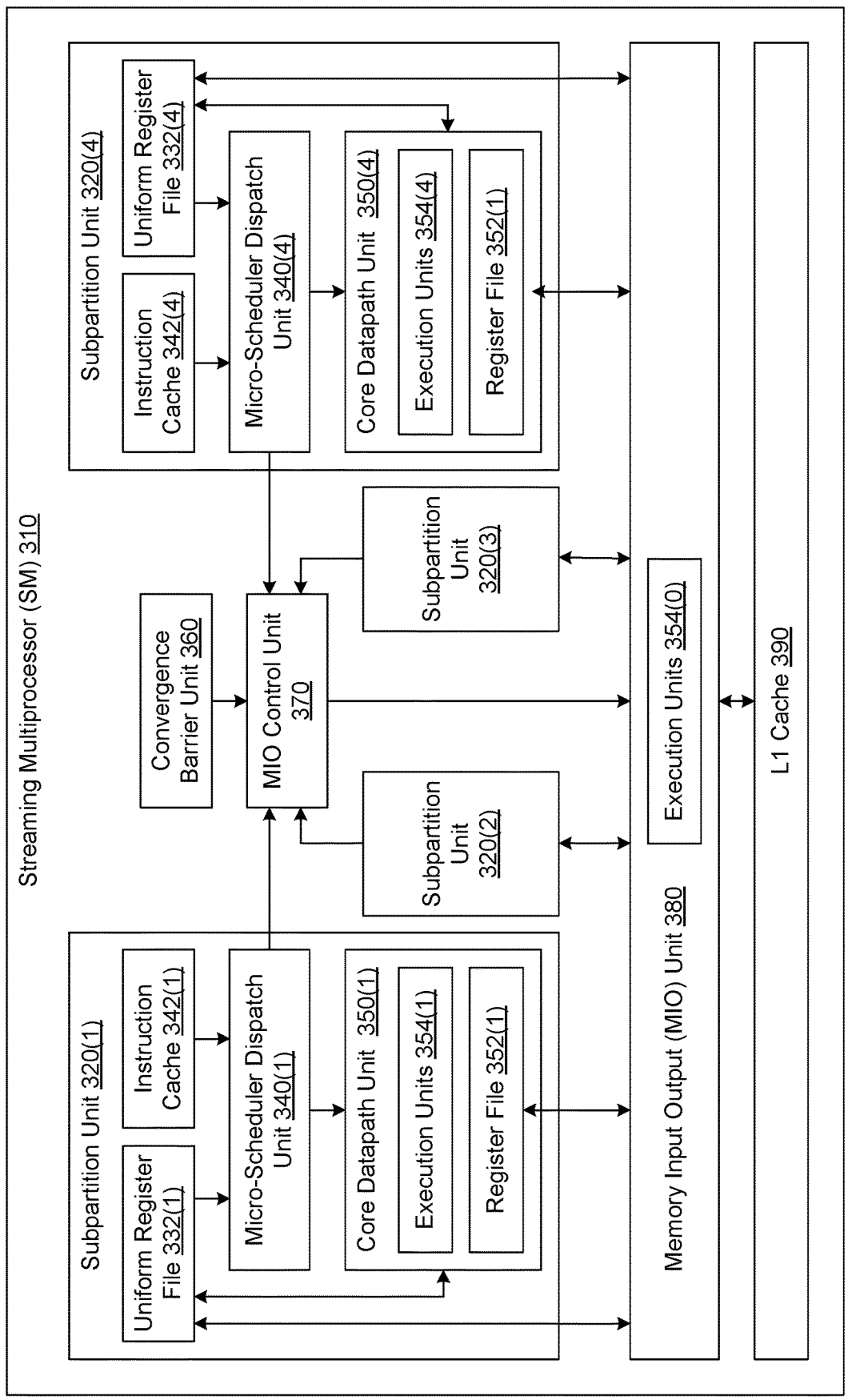
FIG. 3B is a block diagram of the streaming multiprocessor of FIG. 3A, according to various embodiments.

FIG. 3B is a block diagram of the SM 310 of FIG. 3A, according to various embodiments. As shown, in some embodiments, the SM 310 includes, without limitation, subpartition units 320(1)-320(4), a memory input/output (MIO) control unit 370, a MIO unit 380, an L1 cache 390, and a convergence barrier unit (CBU) 360. In some other embodiments, the SM 310 may include any number of subpartition units 320.

In some embodiments, the warps assigned to the SM 310 are distributed between the subpartition units 320. Each of the subpartition units 320 can be assigned any number of warps, however, a given warp is assigned to only one subpartition unit 320. As shown, each of the subpartition units 320 includes, without limitation, an instruction cache 342, a micro-scheduler dispatch unit 340, a core datapath unit 350, and a uniform register file 332. The parenthetical number "x" for each of the uniform register file $332(x)$, the instruction cache $342(x)$, the micro-scheduler dispatch unit $340(x)$, and the core datapath unit $350(x)$ indicates the associated subpartition unit $320(x)$.

As described in conjunction with FIG. 3A, the SM 310 receives processing tasks from the pipeline manager 305. For each warp, the assigned subpartition unit $320(x)$ receives the assigned processing tasks and stores the associated instructions in the instruction cache $342(x)$. The micro-scheduler dispatch unit $340(x)$ reads instructions from the instruction cache $342(x)$. In some embodiments, the micro-scheduler dispatch unit $340(x)$ includes, without limitation, one or more instruction decoders (not shown). In the same or other embodiments, each instruction decoder is coupled to any number of execution units. After an instruction decoder included in the micro-scheduler dispatch unit $340(x)$ decodes a given instruction, the micro-scheduler dispatch unit $340(x)$ issues the instruction to one of the execution units. If the instruction targets one of any number of execution units $354(x)$ that are included in the core datapath unit $350(x)$, then the micro-scheduler dispatch unit $340(x)$ issues the instruction to the execution unit. Otherwise, the micro-scheduler dispatch unit $340(x)$ forwards the instruction to the MIO control unit 370. In some embodiments, the micro-scheduler dispatch unit $340(x)$ includes, without limitation, two dispatch units (not shown) that enable two different instructions from the same warp to be issued during each clock cycle. In some other embodiments, each the micro-scheduler dispatch unit $340(x)$ may include a single dispatch unit or additional dispatch units.

The core datapath unit $350(x)$ includes, without limitation, the execution units $354(x)$ and a register file $352(x)$. Each of the execution units $354(x)$ included in the core datapath unit $350(x)$ can perform any number and type of operations to execute threads of warps assigned to the subpartition unit $320(x)$. Each of the execution units $354(x)$ included in the core datapath unit $350(x)$ has a fixed latency, such as an arithmetic logic unit (ALU). Each of the execution units $354(x)$ included in the core datapath unit $350(x)$ is connected via any number of buses to the register file $352(x)$ and the uniform register file $332(x)$.

The register file $352(x)$ is cache memory that includes, without limitation, any number of registers and any number of read and/or write ports. In some embodiments, each register in the register file $352(x)$ is assigned to one of the threads of one of the warps assigned to the subpartition unit $320(x)$ and is not directly accessible to any of the other threads. In this fashion, each thread of each warp assigned to the subpartition unit $320(x)$ has the exclusive use of a set of registers in the register file $352(x)$. In some embodiments, any number of the registers can be organized as a vector register that stores N M-bit values. For instance, in some embodiments, a vector register can store a different 32-bit value for each thread in a 32-thread warp. The register file $352(x)$ can be implemented in any technically feasible fashion. In some other embodiments, the registers included in the register filer $352(x)$ can be arranged and assigned to threads and/or warps in any technically feasible fashion.

The uniform register file $332(x)$ is a cache memory that includes, without limitation, any number of uniform registers and any number of read and/or write ports. The uniform register file $332(x)$ can be implemented in any technically feasible fashion. In some embodiments, each uniform register in the uniform register file $332(x)$ is accessible to all of the threads included in a warp. In some other embodiments, the uniform registers included in the register filer $352(x)$ can be arranged and assigned to threads and/or warps in any technically feasible fashion.

In some embodiments, CBU 360 manages diverged threads, performs synchronization operations, and ensures forward progress for all non-exited threads included in a warp. When only a portion of the threads in a warp participate in an instruction, the threads in the warp are referred to herein as "diverged" during the execution of the instruction. The CBU 360 can be configured to perform any amount and type of synchronization operations based on any number and type of synchronization instructions.

In some embodiments, the MIO unit 380 includes, without limitation, any number of execution units 354(0). In the same or other embodiments, each of the execution units 354(0) included in the MIO unit 380 can perform any number and type of operations to execute threads assigned to the SM 310 irrespective of the assigned subpartition unit 320. Each of the execution units 354(0) included in the MIO unit 380 is connected via any number of buses to the register files 352(1)-452(4) and the uniform register files 332(1)-332(4).

As shown, in some embodiments, the MIO unit 380 interfaces with the register files 352(1)-452(4), the uniform register files 332(1)-432(4), and the L1 cache 390. The L1 cache 390 can include any type and amount of on-chip memory arranged in any technically feasible fashion. The MIO unit 380 and any number of buses enable each of the execution units 354(0)-354(4) included in the SM 310 to access memory locations included in the L1 cache 390.

In some embodiments, each SM 310 implements, without limitation, one or more integer pipelines (not shown) and one or more floating-point pipelines (not shown). In the same or other embodiments, each of the integer pipelines performs 32-bit integer operations via a set of 32-bit integer execution units, and each of the floating-point pipelines performs 32-bit floating-point operations via a set of 32-bit floating-point execution units (not shown in FIG. 3A). In some embodiments, each SM 310 can issue and execute integer instructions in parallel with floating-point instructions.

In some embodiments, each SM 310 can issue and execute one or more instructions that are specialized to increase the computational efficiency of the matrix-filling phase of the SW algorithm. For instance, in some embodiments, each SM 310 can issue and execute an SW instruction, a VIADD instruction, a VIADDMNMX instruction, a VIMNMX3 instruction, a VIMNMX instruction, or any combination thereof. The SW instruction is described in greater detail below in conjunction with FIG. 6. The VIADD instruction, a VIADDMNMX instruction, a VIMNMX3 instruction are described in greater detail below in conjunction with FIG. 7. The VIMNMX instruction is described in greater detail below in conjunction with FIG. 8.

In the same or other embodiments, the SW instruction, the VIADD instruction, the VIADDMNMX instruction, the VIMNMX3 instruction, the VIMNMX instruction, or any combination thereof are associated with thread computation modes (not shown) of no SIMD, two-way SIMD, and four-way SIMD. As described in greater detail below, in the thread computation modes of no SIMD, two-way SIMD, and four-way SIMD, each thread computes sub-alignment scores for one, two or four local alignment problems, respectively. In the same or other embodiments, one or more SW libraries in the programming platform software stack 160 include, without limitation, pre-written code, kernels, subroutines, intrinsic functions, macros, classes, values, type specifications, etc., that facilitate the use of one or more of the specialized instructions.

In some embodiments, the SW instruction computes SW sub-alignment data for a single thread. The SM 310 can implement the SW instruction in any technically feasible fashion. In some embodiments, the SW instruction is a native instruction that is executed directly by the SM 310. In the same or other embodiments, the SW instruction executes in a integer pipeline. The SW instruction is described in greater detail below in conjunction with FIG. 5.

For explanatory purposes, FIGS. 4-16 describe the SW kernel 192, specialized instructions, macros, intrinsic functions, etc., for thread computation modes (not shown) of no SIMD, two-way SIMD, and four-way SIMD. As described in greater detail below, in the thread computation modes of no SIMD, two-way SIMD, and four-way SIMD, each thread computes sub-alignment scores for one, two or four local alignment problems, respectively, across one or more assigned columns of a scoring matrix. In some other embodiments, the techniques described herein can be modified to implement SW kernels, specialized instructions, macros, intrinsic functions, etc., that assign any portions (including all) of any number of local alignment problems to each thread in any technically feasible fashion.

Interleaving Sub-Alignment Data to Reduce Data Movement

Figure 4:
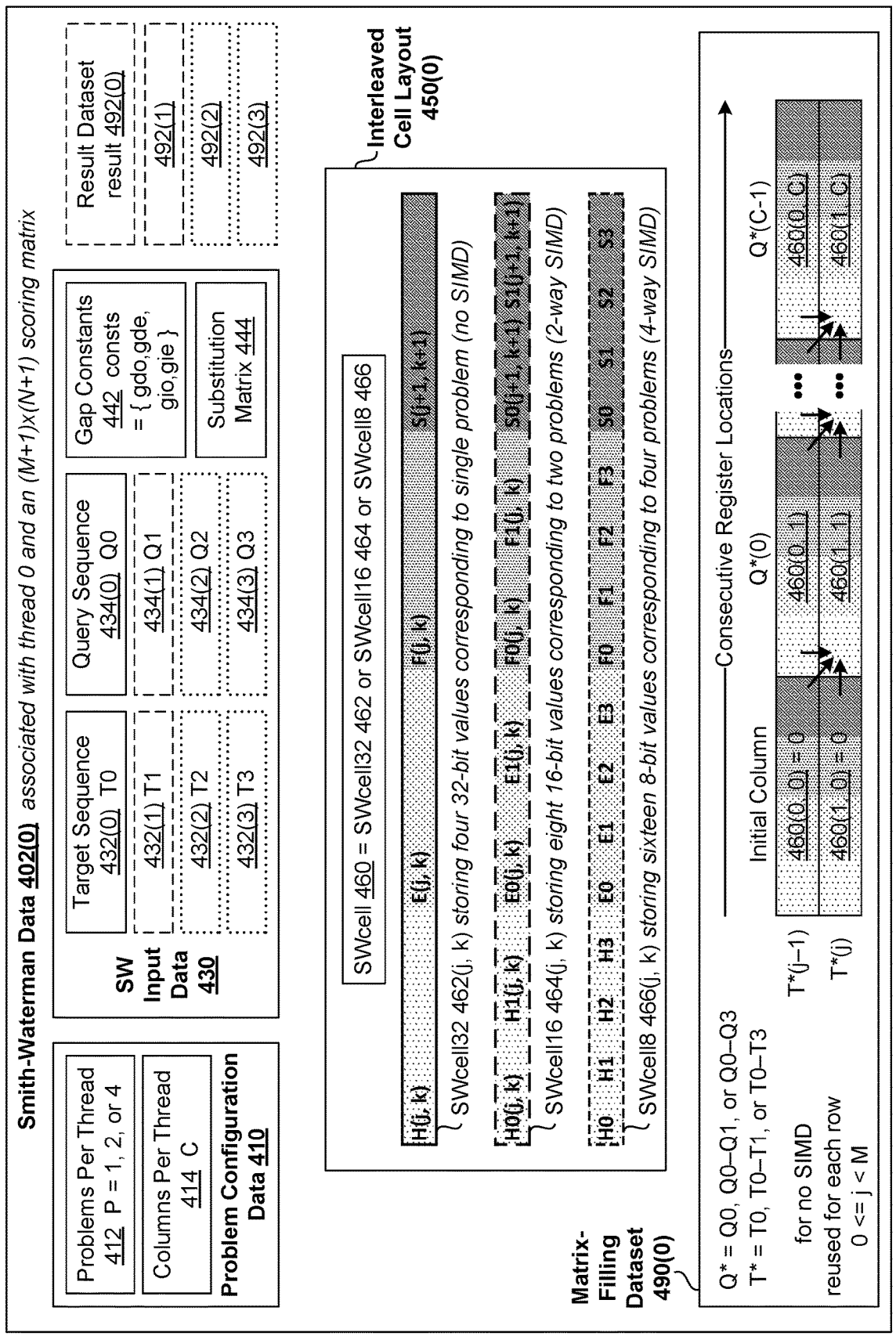
FIG. 4 is an example illustration of Smith-Waterman data associated with the Smith-Waterman kernel of FIG. 1, according to various embodiments.

FIG. 4 is an example illustration of SW data 402(0) associated with the SW kernel 192 of FIG. 1, according to various embodiments. More specifically, the SW data 402(0) illustrates, without limitation, data that is associated with a single thread executing the SW kernel 192 and an (M+1)×(N+1) scoring matrix corresponding to a maximum of M target symbols and N query symbols, where M and N can be any positive integer. In some embodiments, including the embodiment depicted in FIG. 4, the SW data 402(0) is optimized for a scoring matrix traversal pattern in which each thread computes sub-alignment data for an assigned set of columns for each row j before computing sub-alignment data for the assigned set of columns for the row j+1, where j is an integer from 1 through M.

As shown, in some embodiments, the SW data 402(0) includes, without limitation, problem configuration data 410, SW input data 430, an interleaved cell layout 450(0), a matrix-filling dataset 490(0), and a result dataset 492(0). As depicted via a dashed box, if the thread computation mode is two-way SIMD or four-way SIMD, then the SW data 402(0) further includes, without limitation, a result dataset 492(1). As depicted via two dotted boxes, if the thread computation model is four-way SIMD, then the SW data 402(0) further includes, without limitation, a result dataset 492(3) and a result dataset 492(3).

The problem configuration data 410 includes, without limitation, any amount and/or types of data that can be used to determine the number of local sequence alignment problems, the columns of the scoring matrix that are assigned to each thread, the data type and/or data format of the E values, the H values, the sub-alignment values, and the substitution values, or any combination thereof. Each thread can determine the problem configuration data 410 in any technically feasible fashion. In some embodiments, each thread retrieves and/or derives the problem configuration data 410 as-needed based on built-in variables or proprieties of variables. In the same or other embodiments, each thread stores any portion (including all) of the problem configuration data 410 in a register file. As shown, in some embodiments, the problem configuration data 410 includes, without limitation, a problems per thread 412 and a columns per thread 414.

For each thread, the problems per thread 412 specifies the number of local alignment problems for which the thread computes at least a portion of the sub-alignment scores. As depicted in italics, in some embodiments, the problems per thread 412 is denoted as P and is equal to 1, 2, or 4. If the problems per thread 412 is 1, then each thread computes at least a portion of the sub-alignment scores for one local alignment problem. If, however, the problems per thread 412 is 2, then each thread computes at least a portion of the sub-alignment scores for two local alignment problems. And if the problems per thread 412 is 4, then each thread computes at least a portion of the sub-alignment scores for four local alignment problems. Accordingly, the problems per thread 412 of 1, 2, and 4 correspond to the thread computational modes of no SIMD, two-way SIMD, and four-way SIMD, respectively.

In some embodiments, each of one or more scoring matrices represents sub-alignment data for a different set of P local alignment problems. If the problems per thread 412 is 1, then each scoring matrix is associated with a single local alignment problem. If, however, the problems per thread 412 is 2, then each scoring matrix is associated a different set of two local alignment problems. And if the problems per thread 412 is 4, then each scoring matrix is associated with a different set of four local alignment problems.

In some embodiments, for each thread, the columns per thread 414, denoted herein as C, specifies the number of columns of a corresponding scoring matrix that are assigned to the thread. For instance in some embodiments, the columns of a scoring matrix are divided equally between 16 threads, and the columns per thread 414 is equal to N/16, where N is the total number of symbols included in the longest query sequence The SW input data 430 includes, without limitation, any amount and/or types of data that can be used to compute sub-alignment values. In some embodiments, the SW input data 430 includes, without limitation, a target sequence 432(0) denoted as T0, a query sequence 434(0) denoted as Q0, gap constants 442, and a substitution matrix 444. As depicted via two dashed boxes, if the thread computation mode is two-way SIMD or four-way SIMD, then the SW input data 430 further includes, without limitation, a target sequence 432(1) denoted as T1 and a query sequence 434(1) denoted as Q1. As depicted via two dotted boxes, if the thread computation mode is four-way SIMD, then the SW input data 430 further includes, without limitation, a target sequence 432(2), a query sequence 434(2), a target sequence 432(3), and a query sequence 434(3) denoted as T2, Q2, T3, and Q3, respectively.

In some embodiments, each target sequence in the SW input data 430 includes, without limitation, M symbols or a sequence of less than M symbols that is padded to a length of M with dummy symbols. In the same or other embodiments, each query sequence included in the SW input data 430 includes, without limitation, N symbols or a sequence of less than N symbols that is padded to a length of N with dummy symbols.

As shown, in some embodiments, the gap constants 442 (denoted as "consts") include, without limitation, GapDeleteOpen, GapDeleteExtend, GapinsertOpen, and GapinsertExtend that are denoted as gdo, gde, gio, and gie, respectively. In the same or other embodiments, the substitution matrix 444 includes, without limitation, substitution values for each possible combination of the symbols that can be included in the target sequence(s) and the query sequence(s). For instance, in some embodiments, the target sequences and the query sequences are DNA sequences in which each symbol is one of four types of nucleotides (A, G, C, and T), and the substitution matrix 444 is a 4×4 matrix that specifies one value for matrix elements corresponding to the same symbol and another value for matrix elements corresponding to different symbols.

In some other embodiments, the target sequences and the query sequences are protein sequences in which each symbol is one of 20 types of amino acids, and the and the substitution matrix 444 is a 20×20 matrix that specifies the same value for matrix elements corresponding to the same symbol and different values for the remaining matrix elements. In the same or other embodiments, the SW input data 430 can include, without limitation, P different sets of gap constants and/or P different substitution matrices corresponding to P different local alignment problems, and the techniques described herein are modified accordingly.

In some embodiments, each result dataset (e.g., the result dataset 492(0), the result dataset 492(1), the result dataset 492(2), and the result dataset 492(3) includes, without limitation, any number and/or types of variables that enable the computation of a maximum sub-alignment score (not shown in FIG. 4) and a maximum scoring position (not shown in FIG. 4) for the corresponding local alignment problem. In the same or other embodiments, the threads that are assigned to each local alignment problem cooperate via results datasets in any technically feasible fashion to incrementally compute the maximum sub-alignment score and the maximum scoring position for the local alignment problem.

For instance, in some embodiments, the result dataset 492 associated with the highest thread assigned to each local alignment problem includes, without limitation, variables for the maximum sub-alignment score of the local alignment problem and the corresponding maximum scoring position (e.g., a row index and a column index). In the same or other embodiments, each of the other result datasets 492 includes, without limitation, variables for a maximum row sub-alignment score and the corresponding maximum column within the row.

In some embodiments, the target sequences and the query sequences are stored in global memory. In the same or other embodiments, each thread copies at least the assigned portions of each assigned query to an array that resides in a register file and repeatedly copies a portion (e.g., two symbols) of each assigned target sequence as-needed from the global memory to variables or an array that reside in the register file. In some embodiments, the gap constants 442 are stored in constant memory. In the same or other embodiments, the result dataset(s) 492 are stored in a register file.

As shown, in some embodiments, each thread temporarily stores sub-alignment data (e.g., E values, F values, substitution values, and sub-alignment values) in a register file based on the interleaved cell layout 450(0). The interleaved cell layout 450(0) enables the thread to compute dependent sub-alignment data without performing any data movement operations. In some embodiments, instead of storing E values, F values, substitution values, and sub-alignment values in separate matrices in shared memory, each thread temporarily stores E values, F values, substitution values, and sub-alignment values for (C+1) columns of a prior row and (C+1) columns of a current row in at most two arrays of SWcells 460 that reside in contiguous memory location in a register file or memory. In the same or other embodiments, if the thread computation SIMD mode is two-way SIMD or four-way SIMD, each thread packs two values or four values, respectively, into the same number of bits used to represent a single value when the thread computation SIMD mode is no way SIMD.

As shown, when the thread computation SIMD mode is no SIMD, each SWcell 460 is an SWcell32 462. In some embodiments, each SWcell32 462 stores, without limitation, four 32-bit values corresponding to a single local alignment problem. In the same or other embodiments, the SWcell32 462 stores one 32-bit E value across 32 bits of E data, one 32-bit F value across 32 bits of F data, one 32-bit substitution value across 32 bits of substitution data, and one 32-bit sub-alignment score across 32 bits of sub-alignment score data. As described previously herein, because of the offsets in the scoring matrix introduced by the initial row and the initial column, the SWcell32 462(j, k) corresponds to sub-sequences that end in the symbols T0(j−1) and Q0(k−1).

In some embodiments, the SWcell32 462(j, k) includes, without limitation, the sub-alignment score H(j, k), E(j, k), F(j, k), and the substitution value for the symbol T(j+1) and the symbol Q(k+1) that is denoted as S(j+1, k+1). In some other embodiments, the order of H(j, k), E(j, k), F(j, k), and S(j+1, k+1) within the SWcell32(j, k) can vary. In the same or other embodiments, the SWcell32(j, k) can store S(j, k) instead of S(j+1, k+1) or omit S(j+1, k+1).

As shown, when the thread computation SIMD mode is two-way SIMD, each SWcell 460 is an SWcell16 464. In some embodiments, each SWcell16 464 stores, without limitation, eight 16-bit values corresponding to two local alignment problems. In the same or other embodiments, the SWcell16 464 stores two 16-bit E values across 32 bits of E data, two 16-bit F values across 32 bits of F data, two 16-bit substitution values across 32 bits of substitution data, and two 16-bit sub-alignment scores across 32 bits of sub-alignment score data. The SWcell16 464(j, k) corresponds to subsequences that end in the symbols T0(j−1), Q0(k−1), T1(j−1), and Q1(j−1).

In some embodiments, the SWcell16 464(j, k) includes, without limitation, H0(j, k), H1(j, k), E0(j, k), E1(j, k), F0(j, k), F1(j, k), S0(j+1, k+1) and S1(j+1, k+1). In the same or other embodiments, H0(j, k) and H1(j, k) are packed into a single 32-bit value that can be accessed as H(j, k). In some embodiments, E0(j, k) and E1(j, k) are packed into a single 32-bit value that can be accessed as E(j, k). F0(j, k). In some embodiments, F0(j, k) and F1(j, k) are packed into a single 32-bit value that can be accessed as F(j, k). In some embodiments, S0(j+1, k+1) and S1(j+1, k+1) are packed into a single 32-bit value that can be accessed as S(j, k), In some other embodiments, the order of the 32-bit values H(j, k), E(j, k), F(j, k), and S(j+1, k+1) within the SWcell16 464(j, k) can vary. In the same or other embodiments, the order of H0(j, k) and H1(j, k) within H(j, k); E0(j, k), and E1 (j, k) within E(j, k); F0(j, k) and F1(j, k) within F(j, k); S0(j+1, k+1) and S1(j+1, k+1) within S(j+1, k+1); or any combination thereof can be swapped.

As shown, when the thread computation SIMD mode is four-way SIMD, each SWcell 460 is an SWcell8 466. In some embodiments, each SWcell8 466 stores, without limitation, sixteen 8-bit values corresponding to four local alignment problems. In the same or other embodiments, the SWcell16 464 stores four 8-bit E values across 32 bits of E data, four 8-bit F values across 32 bits of F data, four 8-bit substitution values across 32 bits of substitution data, and four 8-bit sub-alignment scores across 32 bits of sub-alignment score data. The SWcell8 466 corresponds to subsequences that end in the symbols T0(j−1), Q0(k−1), T1(j−1), Q1(j−1), T2(j−1), Q2(k−1), T3(j−1), and Q3(j−1).

In some embodiments, the SWcell8 466(j, k) includes, without limitation, H0(j, k), H1(j, k), H2(j, k), H3(j, k), E0(j, k), E1 (j, k), E2(j, k), E3(j, k), F0(j, k), k), F2(j, k), F3(j, k), S0(j+1, k+1), S1(j+1, k+1), S2(j+1, k+1), and S3(j+1, k+1). In the same or other embodiments, H0(j, k), H1(j, k), H2(j, k) and H3(j, k) are packed into a single 32-bit value that can be accessed as H(j, k). In some embodiments, E0(j, k), E1 (j, k), E(j, k) and E3(j, k) are packed into a single 32-bit value that can be accessed as E(j, k). F0(j, k). In some embodiments, F0(j, k) and F1 (j, k) are packed into a single 32-bit value that can be accessed as F(j, k). In some embodiments, S0(j+1, k+1) and S1(j+1, k+1) are packed into a single 32-bit value that can be accessed as S(j, k), In some other embodiments, the order of the 32-bit values H(j, k), E(j, k), F(j, k), and S(j+1, k+1) within the SWcell8 466(j, k) can vary. In the same or other embodiments, the order of H0(j, k), H1(j, k), H2(j, k), and H3(j, k) within H0(j, k); E0(j, k), E1 (j, k), E2(j, k), and E3(j, k) within E(j, k); F0(j, k), F1 (j, k), F2(j, k), and F3(j, k) within F(j, k); S0(j+1, k+1) S1(j+1, k+1), S2(j+1, k+1), and S3(j+1, k+1) within S(j+1, k+1); or any combination thereof can be altered.

In some embodiments, the SW kernel 192 and/or one or more SW libraries included in the programming platform software stack 160 of FIG. 1 include, without limitation, one or more mappings that facilitate writing data to and reading data from the SWcell 460, the SWcell32 462, the SWcell16 464, and the SWcell8 462. For instance, in some embodiments, the SW kernel 192 and/or one or more SW libraries include the following type definitions (2):

```
typedef union SWcell {                              (2)
    typedef struct SWcell32 {
        int32_t H; int32_t E; int32_t F; int32_t S;
    } SWcell32_t;
    typedef struct SWcell16 {
        int16_t H0; int16_t H1; int16_t E0; int16_t E1;
        int16_t F0; int16_t F1; int16_t S0; int16_t S1;
    } SWcell16_t;
    typedef struct SWcell8 {
        int8_t H0; int8_t H1; int8_t H2; int8_t H3;
        int8_t E0; int8_t E1; int8_t E2; int8_t E3;
        int8_t F0; int8_t F1; int8_t F2; int8_t F3;
        int8_t S0; int8_t S1; int8_t S2; int8_t S3;
    } SWcell8_t;
    SWcell32_t c32;
    SWcell16_t c16;
    SWcell8_t c8;
    uint32_t data[4];
} SWcell_t;
```

In the same or other embodiments, the SW kernel 192 and/or one or more SW libraries included in the programming platform software stack 160 of FIG. 1 include, without limitation, one or more mappings that facilitate no SIMD, 2-way SIMD, and 4-way SIMD operations involving the gap constants 442. For instance, in some embodiments, the SW kernel 192 and/or one or more SW libraries include the following type definitions (3):

```
typedef struct sw constants_simd_1 {                (3)
    int32_t gde; int32_t gdo; int32_t gie; int32_t gio;
} sw_constants_simd_1_t;
typedef union sw_constants_simd_2 {
    typedef struct constants_32 {
        int32_t gde; int32_t gdo; int32_t gie; int32_t gio;
    } constants_32_t;
    typedef struct constants_16 {
        int16_t gde0; int16_t gde1; int16_t gdo0; int16_t gdo1;
        int16_t gie0; int16_t gie1; int16_t gio0; int16_t gio1;
    } constants_16_t;
    constants_32_t c32;
    constants_16_t c6;
} sw_constants_simd_2_t;
typedef union sw_constants_simd_4 {
    typedef struct constants_32 {
        int32_t gde; int32_t gdo; int32_t gie; int32_t gio;
    } constants_32_t;
    typedef struct constants_16 {
        int16_t gde0; int16_t gde1; int16_t gdo0; int16_t gdo1;
        int16_t gie0; int16_t gie1; int16_t gio0; int16_t gio1;
    } constants_16_t;
    typedef struct constants_8 {
        int8_t gde0; int8_t gde1; int8_t gde0; int8_t gde1;
        int8_t gdo0; int8_t gdo1; int8_t gdo0; int8_t gdo1;
        int8_t gie0; int8_t gie1; int8_t gie0; int8_t gie1;
        int8_t gio0; int8_t gio1; int8_t gio0; int8_t gio1;
    } constants_8_t;
```

```
    constants_32_t c32;
    constants_16_t c16;
    constants_8_t c8;
} sw_constants_simd_4_t;
```

In some embodiments, each thread stores the information required to compute the sub-alignment data corresponding to the assigned columns of the scoring matrix via the matrix-filling dataset 490(0) that the thread reuses for each row 0<=j<M. Referring back to equations (1a)-(1c) in conjunction with the arrows superimposed on the matrix-filling dataset 490(0), H(j, k) stored in the SWcell 460(j, k) depends on H(j−1, k−1) and S(j, k) stored in the SWcell 460(j−1, k−1), E(j−1, k) and H(j−1, k) stored in the SWcell 460(j−1, k), and F(j, k−1) and H(j, k−1) stored in the SWcell 460(j, k−1).

For explanatory purposes only, the matrix-filling dataset 490(0) depicted in FIG. 4 corresponds to a thread 0 that computes sub-alignment data for the columns 1-C of the scoring matrix corresponding to the query symbols Q*(0)–Q*(C−1), respectively. For explanatory purposes, for the thread computation SIMD modes of no SIMD, two-way SIMD, and four-way SIMD, Q* denotes Q0, Q0-Q1, and Q0-Q3, respectively, and T* denotes T0, T0-T1, and T0-T3, respectively. As shown, in some embodiments, the matrix-filling dataset 490(0) includes, without limitation, two arrays of (C+1) SWcells 460 that reside in consecutive register locations or consecutive memory locations. One array corresponds to the target symbol(s) T*(j−1), and includes, without limitation, an SWcell 460(0, 0) that is included in an initial column and SWcells 460(0, 1)-460(0, C) corresponding to the query symbols Q*(0)-Q*(C−1), respectively. The other array corresponds to the target symbol(s) T*(j), and includes, without limitation, an SWcell 460(1, 0) that is included in the initial column and SWcells 460(1, 1)-460(1, C) corresponding to the query symbols Q*(0)-Q*(C−1), respectively.

Although not shown, in some embodiments, each thread maintains a "current row" register variable that points to the array of SWcells 460 corresponding to the current row and a "prior row" register variable that points to the array of SWcells 460 corresponding to the prior row. After computing the sub-alignment data for the current row, the thread updates the current row register variable and the prior row register variable such that the prior row register variable points to the array of SWcells 460 previously pointed to by the current row register, and the current row register variable points to the array of SWcells 460 previously pointed to by the prior row register. The thread can swap the current row and prior row designations in any technically feasible fashion.

In some embodiments, to swap the current row of and prior row designations for rows 1 through M of the scoring matrix corresponding to the target symbols T*(0) through T*(M−1), the SW kernel 192 implements the following pseudocode (4):

```
    // temporary storage for the matrix-filling dataset 490(0)
(4)
    SWcell_t cells[2, N+1]
    // initialize top row and left entry of next row to 0
    memset(cells[0], 0, sizeof(SWcell_t)*(N+1));
    memset(cells[1], 0, sizeof(SWcell_t));
    for (uint32_t row = 1; row <= M; ++row) {
```

```
        const uint32_t prevID = (row % 2) == 0 ? 1 : 0;
        const uint32_t currentID = row % 2;
        ...
}
```

Note with respect to the pseudocode (4), each even row (including the initialization row) of the scoring matrix is represented by the array of cells that starts at the initial cell denoted as cells[0, 0]. In the same or other embodiments, each odd row of the scoring matrix is represented by the array of cells that starts at the initial celld denoted as cells[1, 0].

Figure 5:
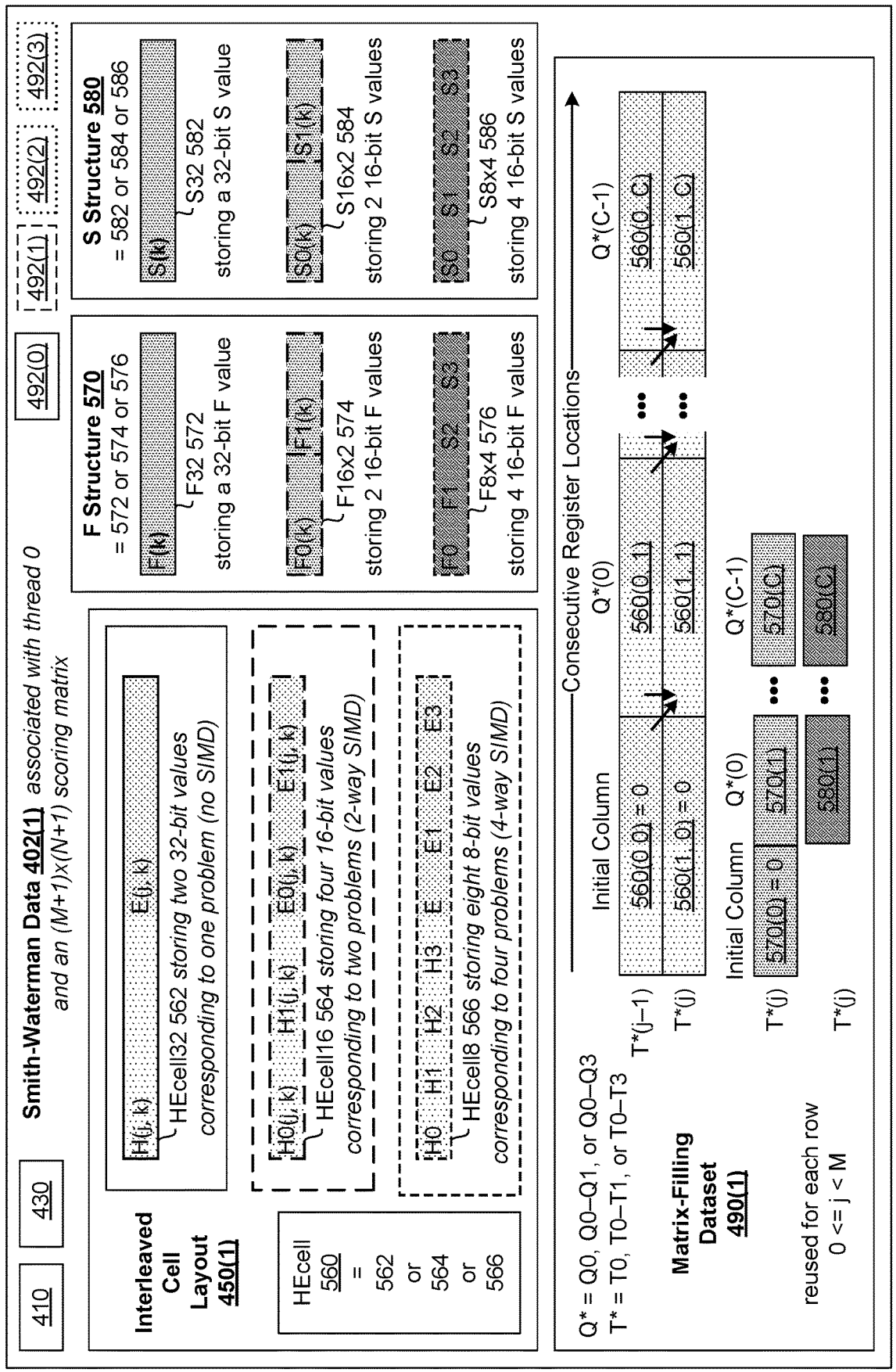
FIG. 5 is an example illustration of Smith-Waterman data associated with the Smith-Waterman kernel of FIG. 1, according to other various embodiments.

Advantageously, because each thread computes sub-alignment data for the current row from left to right, the dependencies of H(j, k) are automatically met via the matrix-filling dataset 490(0) and the current row/prior row swapping technique without executing any memory movement instructions FIG. 5 is an example illustration of SW data 402(1) associated with the SW kernel 192 of FIG. 1, according to other various embodiments. More specifically, the SW data 402(1) illustrates, without limitation, data that is associated with a single thread executing the SW kernel 192 and an (M+1)×(N+1) scoring matrix corresponding to a maximum of M target symbols and N query symbols, where M and N can be any positive integer. In some embodiments, including the embodiment depicted in FIG. 5, the SW data 402(1) is optimized for a scoring matrix traversal pattern in which each thread computes sub-alignment data for an assigned set of columns for a row j before computing sub-alignment data for the assigned set of columns for the row j+1, where j is an integer from 1 through M.

As shown, in some embodiments, the SW data 402(1) includes, without limitation, the problem configuration data 410, the SW input data 430, an interleaved cell layout 450(1), a matrix-filling dataset 490(1), and the result dataset 492(0). As depicted via a dashed box, if the thread computation mode is two-way SIMD or four-way SIMD, then the SW data 402(1) further includes, without limitation, the result dataset 492(1). As depicted via two dotted boxes, if the thread computation model is four-way SIMD, then the SW data 402(1) further includes, without limitation, the result dataset 492(3) and the result dataset 492(3).

In some embodiments, the problem configuration data 410, the SW input data 430, and the result datasets 492(0)-492(3) included in the SW data 402(1) are the same as the problem configuration data 410, the SW input data 430, and the result datasets 492(0)-492(3) included in the SW data 402(0) and described previously herein in conjunction with FIG. 4. Relative to the interleaved cell layout 450(0) and the matrix-filling dataset 490(0) included in the SW data 402(0), the amount of memory required to store the interleaved cell layout 450(1) and the matrix-filling dataset 490(1), respectively, that are included in the SW data 402(1) are reduced.

As shown, in some embodiments, each thread temporarily stores sub-alignment data (e.g., E values, F values, substitution values, and sub-alignment values) based on the interleaved cell layout 450(1). The interleaved cell layout 450(1) enables the thread to compute dependent sub-alignment data without performing any data movement operations. In some embodiments, each thread temporarily stores sub-alignment scores and E values for (C+1) columns of a prior row and (C+1) columns of a current row in at most two arrays of HEcells 560 that reside in contiguous register or memory locations. Each thread temporarily stores F values for (C+1)

columns of a current row in an array of F structures 570 that resides in consecutive register or memory locations. In the same or other embodiments, for performance reasons, each thread temporarily stores substitution values for C columns of the current row in an array of S structures 580 that resides in consecutive register or memory locations. In some other embodiments, each thread temporarily stores a single substitution value in a single instance of the S structure 580 that resides in a register or memory. In some embodiments, if the thread computation SIMD mode is two-way SIMD or four-way SIMD, each thread packs two values or four values, respectively, into the same number of bits used to represent a single value when the thread computation SIMD mode is no way SIMD.

As shown, when the thread computation SIMD mode is no SIMD, each HEcell 560 is an HEcell32 562 that stores two 32-bit values corresponding to a single local alignment problem, each F structure 570 is an F32 572 that stores one 32-bit F value corresponding to the same local alignment problem, and each S structure 580 is an S32 582 that stores one 32-bit S value corresponding to the same local alignment problem. In the same or other embodiments, the HEcell32 562 stores one 32-bit E value across 32 bits of E data and one 32-bit sub-alignment score across 32 bits of sub-alignment score data. As described previously herein, because of the offsets in the scoring matrix introduced by the initial row and the initial column, the HEcell32 562($j, k$), the F32 572($k$), and the S32 582($k$) correspond to subsequences that end in the symbols T0(j−1) and Q0(k−1). In some embodiments, the HEcell32 562($j, k$) includes, without limitation, the sub-alignment score H(j, k) followed by E(j, k). In some other embodiments, the HEcell32 562($j, k$) includes, without limitation, E(j, k) followed by the sub-alignment score H(j, k).

As shown, when the thread computation SIMD mode is two-way SIMD, each HEcell 560 is an HEcell16 564 that stores four 16-bit values corresponding to two local alignment problems, each F structure 570 is an F16×2 574 that stores two 16-bit F values corresponding to two local alignment problems, and each S structure 580 is an S16×2 584 that stores two 16-bit S values corresponding to two local alignment problems. In the same or other embodiments, the HEcell16 564 stores two 16-bit E values across 32 bits of E data and two 16-bit sub-alignment scores across 32 bits of sub-alignment score data. The HEcell16 564($j, k$), the F16×2 574($k$), and the S16×2 584($k$) correspond to subsequences that end in the symbols T0(j−1), Q0(k−1), T1(j−1), and Q1(k−1).

In some embodiments, the HEcell16 564($j, k$) includes, without limitation, H0(j, k), H1(j, k), E0(j, k), and E1 (j, k). In the same or other embodiments, H0(j, k) and H1(j, k) are packed into a single 32-bit value that can be accessed as H(j, k). In some embodiments, E0(j, k) and E1 (j, k) are packed into a single 32-bit value that can be accessed as E(j, k). In some other embodiments, the order of the 32-bit values H(j, k) and E(j, k) within the HEcell16 564($j, k$) can vary. In the same or other embodiments, the order of H0(j, k) and H1(j, k) within H(j, k), E0(j, k) and E1 (j, k) within E(j, k), or any combination thereof can be swapped.

As shown, when the thread computation SIMD mode is four-way SIMD, each HEcell 560 is an HEcell8 566 that stores eight 8-bit values corresponding to four local alignment problems, each F structure 570 is an F8×4 576 that stores four 8-bit F values corresponding to four local alignment problems, and each S structure 580 is an S8×4 586 that stores four 8-bit S values corresponding to four local alignment problems. In the same or other embodiments, the HEcell8 566 stores four 8-bit E values across 32 bits of E data and four 8-bit sub-alignment scores across 32 bits of sub-alignment score data. The HEcell8 566($j, k$), the F8×4 576($k$), and the S8×4 586($k$) correspond to subsequences that end in the symbols T0(j−1), Q0(k−1), T1(j−1), Q1(k−1), T2(j−1), Q2(k−1), T3(j−1), and Q3(k−1).

In some embodiments, the HEcell8 566($j, k$) includes, without limitation, H0(j, k), H1(j, k), H2(j, k), H3(j, k), E0(j, k), E1(j, k), E2(j, k), and E3(j, k). In the same or other embodiments, H0(j, k), H1(j, k), H2(j, k) and H3(j, k) are packed into a single 32-bit value that can be accessed as H(j, k). In some embodiments, E0(j, k), E1(j, k), E(j, k) and E3(j, k) are packed into a single 32-bit value that can be accessed as E(j, k). F0(j, k). In some embodiments, F0(j, k) and F1 (j, k) are packed into a single 32-bit value that can be accessed as F(j, k). In some embodiments, the order of H0(j, k), H1(j, k), H2(j, k), and H3(j, k) within H0(j, k); and E0(j, k), E1(j, k), E2(j, k), and E3(j, k) within E(j, k); or any combination thereof can be altered.

In some embodiments, the SW kernel 192 and/or one or more SW libraries included in the programming platform software stack 160 of FIG. 1 include, without limitation, one or more mappings that facilitate writing data to and reading data from the HEcell 560, the HEcell32 562, the HEcell16 564, and the HEcell8 566. In the same or other embodiments, the SW kernel 192 and/or one or more SW libraries included in the programming platform software stack 160 of FIG. 1 include, without limitation, one or more mappings that facilitate no SIMD, 2-way SIMD, and 4-way SIMD operations involving the gap constants 442. For instance, in some embodiments, the SW kernel 192 and/or one or more SW libraries include the type definitions (3) described previously herein in conjunction with FIG. 4.

In some embodiments, each thread stores the information required to compute the sub-alignment data corresponding to the assigned columns of the scoring matrix via a matrix-filling dataset 490(1) that the thread reuses for each row 0<=j<M. Referring back to equations (1a)-(1c) in conjunction with the arrows superimposed on the matrix-filling dataset 490(1), H(j, k) stored in the HEcell 560($j, k$) depends on H(j−1, k−1) stored in the HEcell 560($j$−1, k−1), E(j−1, k) and H(j−1, k) stored in the HEcell 560($j$−1, k−1), H(j, k−1) stored in the HEcell 560($j$−1, k−1), S(j, k), and F(j, k−1).

For explanatory purposes only, the matrix-filling dataset 490(1) depicted in FIG. 5 corresponds to a thread 0 that compute sub-alignment data for the columns 1-C of the scoring matrix corresponding to the query symbols Q*(0)−Q*(C−1), respectively. As shown, in some embodiments, the matrix-filling dataset 490(1) includes, without limitation, two arrays of (C+1) HEcell 560 that reside in consecutive register locations or consecutive memory locations, F structures 570(0)-570(C) that reside in consecutive register locations or consecutive memory locations, and S structures 580(1)-580(C) that reside in consecutive register locations or consecutive memory locations. One array of HEcells 560 corresponds to the target symbol(s) T*(j−1), and includes, without limitation, an HEcell 560(0, 0) that is included in an initial column and HEcells 560(0, 1)-560(0, C) corresponding to the query symbols Q*(0)-Q*(C−1), respectively. The other array of HEcells 560 corresponds to the target symbol(s) T*(j), and includes, without limitation, an HEcell 560(1, 0) that is included in the initial column and HEcells 560(1, 1)-560(1, C) corresponding to the query symbols Q*(0)−Q*(C−1), respectively. F structure 570(0) corresponds to the initial column, and F structures 570(1)-570(C) correspond to the query symbols Q*(0)−Q*(C−1), respectively. S structures 580(1)-580(C) correspond to the query symbols Q*(0)–Q*(C−1), respectively.

Relative to the matrix-filling dataset 490(0) described previously herein in conjunction with FIG. 4, the matrix-filling dataset 490(1) stores (2C+3)*32 fewer bits in the register file. For example, if the thread 0 is assigned one hundred columns and uses the matrix-filling dataset 490(1) instead of the matrix-filling dataset 490(0) to store sub-alignment data, then the thread 0 would store 6496 bits in the register file.

Although not shown, in some embodiments, each thread maintains a "current row" register variable that points to the array of HEcells 560 corresponding to the current row and a "prior row" register variable that points to the array of HEcells 560 corresponding to the prior row. After computing the sub-alignment data for the current row, the thread updates the current row register variable and the prior row register variable such that the prior row register variable points to the array of HEcells 560 previously pointed to by the current row register, and the current row register variable points to the array of HEcells 560 previously pointed to by the prior row register. The thread can swap the current row and prior row designations in any technically feasible fashion. Advantageously, because each thread computes sub-alignment data for the current row from left to right, the dependencies of H(j, k) are automatically met via the matrix-filling dataset 490(1) and the current row/prior row swapping technique without executing any memory movement instructions.

Specialized Instructions for Smith Waterman Computations

Figure 6:
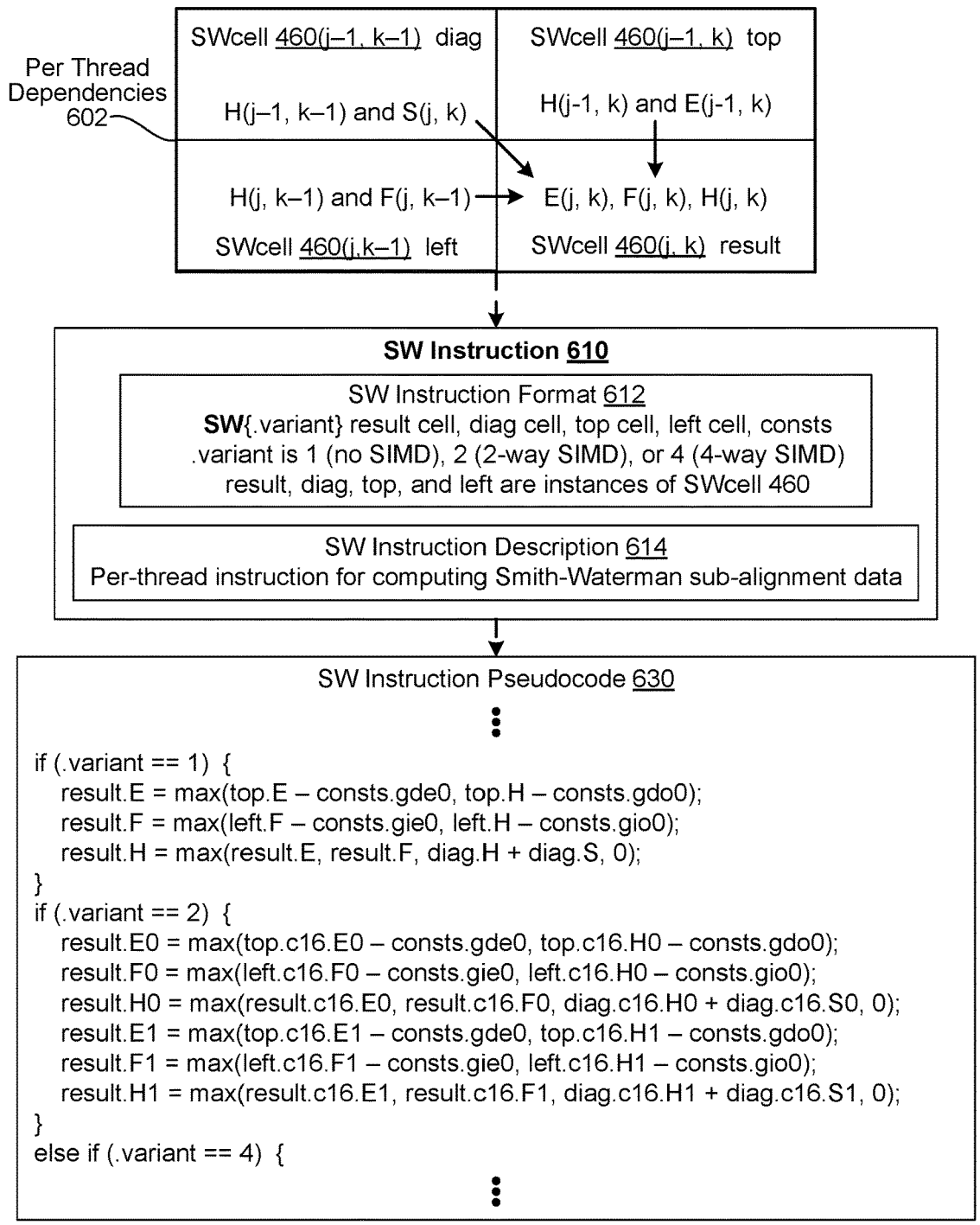
FIG. 6 illustrates a Smith-Waterman instruction that is executed by the Smith-Waterman kernel of FIG. 1, according to various embodiments.

FIG. 6 illustrates an SW instruction 610 that is executed by the SW kernel of FIG. 1, according to various embodiments. In some embodiments, the SW instruction 610 is a per-thread instruction that is issued and executed in a SIMT fashion. As noted previously herein in conjunction with FIGS. 3A-3B, in some embodiments, each SM 310 can issue and execute the SW instruction 610 in any technically feasible fashion.

As depicted in an SW instruction description 614, in some embodiments, the SW instruction 610 is a per-thread instruction for computing SW sub-alignment data. In the same or other embodiments, the SW instruction 610 generates sub-alignment data associated with a single position in a scoring matrix. In some embodiments, the SW instruction 610 supports, without limitation, multiple SIMD variants, data types/sizes, or any combination thereof.

In some embodiments, a no SIMD variant of the SW instruction 610 operates on 32-bit data to generate sub-alignment data associated with a single position for a single local alignment problem. In the same or other embodiments, a 2-way SIMD variant of the SW instruction 610 operates on 16-bit data to generate sub-alignment data associated with a single position and two local alignment problems. In some embodiments, a 4-way SIMD variant of the SW instruction 610 operates on 8-bit data to generate sub-alignment data associated with a single position and four local alignment problems.

As shown, in some embodiments, an SW instruction format 612 is "SW{.variant} result, diag, top, left, consts." Accordingly, each SW instruction 610 includes, without limitation, an instruction name of "SW," an optional .variant modifier, a destination address result, and source addresses diag, top, left, and consts. In some embodiments, the .variant modifier indicates a SIMD variant. In the same or other embodiments, allowed values for .variant modifier include, without limitation, 1, 2, and 4 indicating no SIMD, 2-way SIMD, and 4-way SIMD, respectively.

In some embodiments, the SW instruction 610 is designed to operate on operands having the interleaved cell layout 450(0), and the operands result, diag, top, and left specify the locations of SWcells 460 that reside in registers. In some embodiments, the operand consts is the address of a set of constants that includes, without limitation, GapDeleteOpen, GapDeleteExtend, GapinsertOpen, and GapinsertExtend. In the same or embodiments, the operand consts specifies the location of the gap constants 442 that reside in a uniform register, constant memory, or a register.

In some embodiments, the SW instruction 610 computes data for the SWcell 460 specified by the operand result based on per thread inputs from the SWcells 460 specified by the diag, top, and left operands and a set of constant inputs that is uniform for all threads and specified by the operands consts. Per-thread dependencies 602 graphically depicts the per-thread input data that the SW instruction 610 reads from the SWcells 460 corresponding to the diag, top, and left operands as well as the output data that the SW instruction 610 computes and writes to the SWcell 460 corresponding to the result operands, in some embodiments. As shown, the result, diag, top, and left operands correspond to the SWcells 460(j, k), 460(j−1, k−1), 460(j−1, k), and 460(j, k−1), respectively. In some embodiments, the SW instruction 610 computes E(j, k), F(j, k), and H(j, k) in the SWcell 460(j, k) based on H(j−1, k−1) and S(j, k) in the SWcell 460(j−1, k−1), H(j−1, k) and E(j−1, k) in the SWcell 460(j−1, k), and G(j, k−1) and F(j, k−1) in the SWcell 460(j, k−1). The SW instruction 610 can cause the SM 310 to compute E(j, k), F(j, k), and H(j, k) in any technically feasible fashion.

SW instruction pseudocode 630 illustrates exemplar operations that can be performed by the SM 310 when executing the SW instruction 610 in some embodiments. In some embodiments, if the .variant modifier is one, then a thread executing on the SM 310 performs the following computations (5a)-(5c):

$$\text{result}.E = \max(\text{top}.E - \text{consts.gde}, \text{top}.H - \text{consts.gdo}); \quad (5a)$$

$$\text{result}.F = \max(\text{left}.F - \text{consts.gie}, \text{left}.H - \text{consts.gio}); \quad (5b)$$

$$\text{result}.H = \max(\text{result}.E, \text{result}.F, \text{diag}.H + \text{diag}.S, 0); \quad (5c)$$

In some embodiments, if the .variant modifier is two, then the SM 310 performs the following computations (6a)-(6f):

$$\text{result}.E0 = \max(\text{top}.c16.E0 - \text{consts.gde}, \text{top}.c16.H0 - \text{consts.gdo}); \quad (6a)$$

$$\text{result}.F0 = \max(\text{left}.c16.F0 - \text{consts.gie}, \text{left}.c16.H0 - \text{consts.gio}); \quad (6b)$$

$$\text{result}.H0 = \max(\text{result}.c16.E0, \text{result}.c16.F0, \quad (6c)$$

$$\text{diag}.c16.H0 + \text{diag}.c16.S0, 0);$$

$$\text{result}.E1 = \max(\text{top}.c16.E1 - \text{consts.gde}, \text{top}.c16.H1 - \text{consts.gdo}); \quad (6d)$$

$$\text{result}.F1 = \max(\text{left}.c16.F1 - \text{consts.gie}, \text{left}.c16.H1 - \text{consts.gio}); \quad (6e)$$

$$\text{result}.H1 = \max(\text{result}.c16.E1, \text{result}.c16.F1, \quad (6f)$$

$$\text{diag}.c16.H1 + \text{diag}.c16.S1, 0);$$

Although not shown, in some embodiments, if the .variant modifier is four, then the SM 310 performs the following computations (7a)-(7l):

result.$E0$=max(top.$c8.E0$−consts.gde, top.$c8.H0$−
consts.gdo); (7a)

result.$F0$=max(left.$c8.F0$−consts.gie, left.$c8.H0$−
consts.gio); (7b)

result.$H0$=max(result.$c8.E0$,result.$c8.F0$, (7c)

diag.$c8.H0$+diag.$c8.S0$,0);

result.$E1$=max(top.$c8.E1$−consts.gde, top.$c8.H1$−
consts.gdo); (7d)

result.$F1$=max(left.$c8.F1$−consts.gie, left.$c8.H1$−
consts.gio); (7e)

result.$H1$=max(result.$c8.E1$, result.$c8.F1$, (7f)

diag.$c8.H1$+diag.$c8.S1$, 0);

result.$E2$=max(top.$c8.E2$−consts.gde, top.$c8.H2$−
consts.gdo); (7g)

result.$F2$=max(left.$c8.F2$−consts.gie, left.$c8.H2$−
consts.gio); (7h)

result.$H2$=max(result.$c8.E2$, result.$c8.F2$, (7i)

diag.$c8.H2$+diag.$c8.S2$, 0);

result.$E3$=max(top.$c8.E3$−consts.gde, top.$c8.H3$−
consts.gdo); (7j)

result.$F3$=max(left.$c8.F3$−consts.gie, left.$c8.H3$−
consts.gio); (7k)

result.$H3$=max(result.$c8.E3$, result.$c8.F3$, (7l)

diag.$c8.H3$+diag.$c8.S3$, 0);

Advantageously, and as depicted in a SW instruction improvement table 690, the SW instruction 610 requires fewer instructions and fewer cycles than a conventional 10-instruction sequence to compute sub-alignment data associated with a single position in a scoring matrix. For explanatory purposes, in the context of FIG. 6, the required number of cycles described herein is based on embodiments having a four cycle throughput for the SW instruction 610. In other embodiments, the cycle throughput for the SW instruction 610 and therefore the required number of cycles can vary.

As shown, in some embodiments, to compute sub-alignment data associated with a single position in a scoring matrix for a single local alignment problem (corresponding to a no SIMD variant), a conventional 10-instruction sequence requires ten instructions and ten cycles, and the SW instruction 610 requires one instruction and four cycles. Relative to a conventional 10-instruction sequence, the no SIMD variant of the SW instruction 610 can therefore require 90% fewer instructions and 60% fewer cycles.

In some embodiments, to compute sub-alignment data associated with a single position in a scoring matrix for two local alignment problems (corresponding to a 2-way SIMD variant), a conventional 10-instruction sequence requires twenty instructions and twenty cycles, and the SW instruction 610 requires one instruction and four cycles. Relative to a conventional 10-instruction sequence, the 2-way SIMD variant of the SW instruction 610 can therefore require 95% fewer instructions and 80% fewer cycles.

In some embodiments, to compute sub-alignment data associated with a single position in a scoring matrix for four local alignment problems (corresponding to a 4-way SIMD variant), a conventional 10-instruction sequence requires thirty instructions and thirty cycles, and the SW instruction 610 requires one instruction and four cycles. Relative to a conventional 10-instruction sequence, the 4-way SIMD variant of the SW instruction 610 can therefore require 96% fewer instructions and 86% fewer cycles.

Note that the techniques described herein are illustrative rather than restrictive and can be altered without departing from the broader spirit and scope of the invention. Many modifications and variations on the functionality provided by the SM 310, the SW instruction 610, and the SW kernel 192 will be apparent to those of ordinary skill in the art without departing from the scope and spirit of the described embodiments. For instance, in some other embodiments, variants of the SW instruction 610 can operate on operands having layouts other than the interleaved cell layout 450(0), different SIMD variants, E values, F values, substitution values, and sub-alignment scores having different data types/formats, etc.

Figure 7:
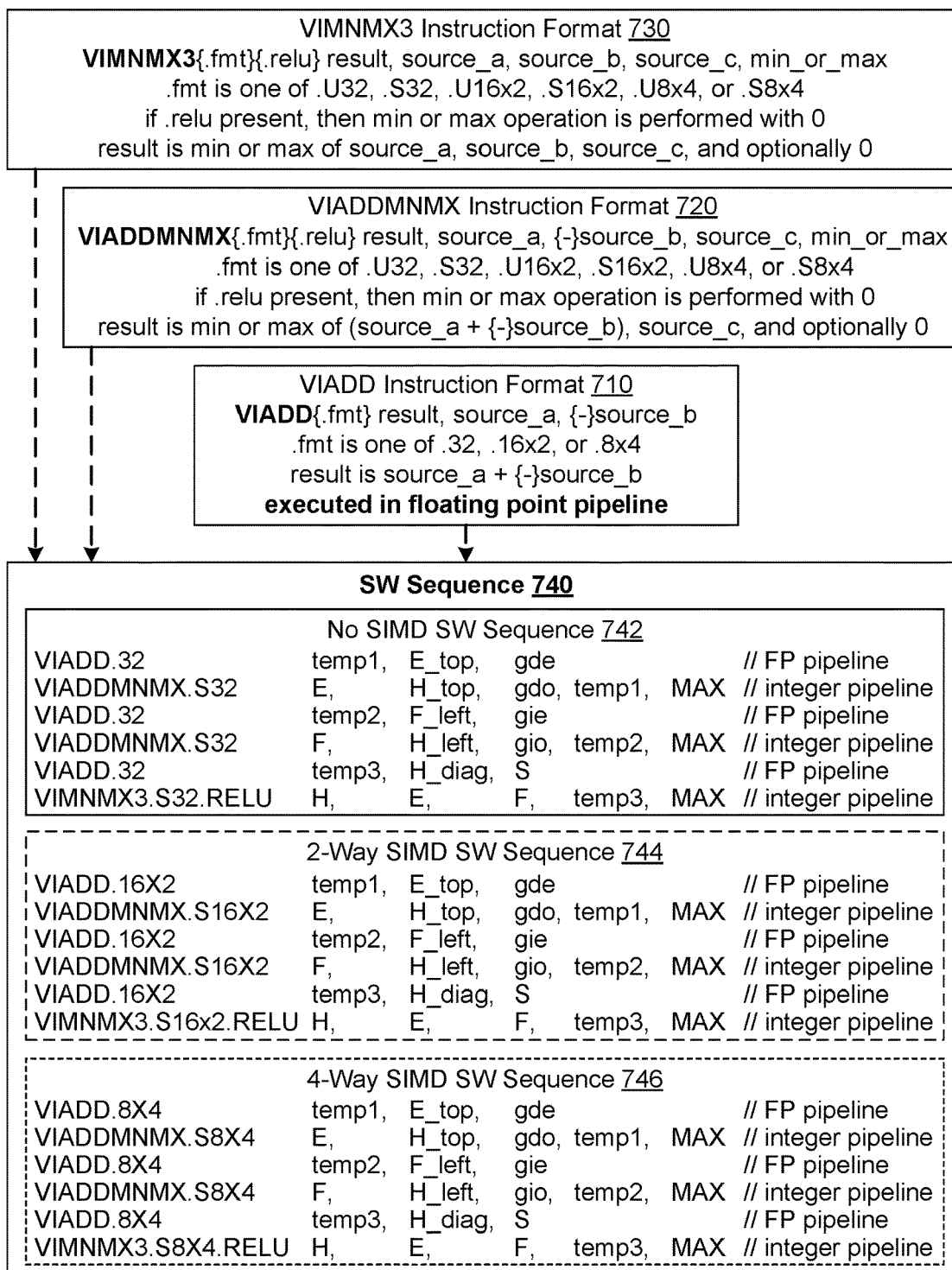
FIG. 7 illustrates a Smith-Waterman sequence that is executed by the Smith-Waterman kernel of FIG. 1, according to various other embodiments.

FIG. 7 illustrates a SW sequence 740 that is executed by the SW kernel 192 of FIG. 1, according to various other embodiments. In some embodiments, the SW sequence 740 is a per-thread sequence of six instructions for computing SW sub-alignment data. In the same or other embodiments, the SW sequence 740 generates sub-alignment data associated with a single position in a scoring matrix. In some embodiments, the SW sequence 740 supports, without limitation, multiple SIMD variants, data types/sizes, or any combination thereof.

In some embodiments, a no SIMD variant of the SW sequence 740 operates on 32-bit data to generate sub-alignment data associated with a single position for a single local alignment problem. In the same or other embodiments, a 2-way SIMD variant of the SW sequence 740 operates on 16-bit data to generate sub-alignment data associated with a single position and two local alignment problems. In some embodiments, a 4-way SIMD variant of the SW sequence 740 operates on 8-bit data to generate sub-alignment data associated with a single position and four local alignment problems.

As shown, in some embodiments, SW sequence 740 includes three VIADD instructions, two VIADDMNMX instructions, and a VIMNMX3 instruction. In some embodiments, each VIADD instruction, VIADDMNMX instruction, and VIMNMX3 instruction is a per-thread instruction that is issued and executed in a SIMT fashion. In some embodiments, each SM 310 can issue and execute each VIADD instruction, VIADDMNMX instruction, and VIMNMX3 instruction in any technically feasible fashion.

In some embodiments, each VIADD instruction, VIADDMNMX instruction, and VIMNMX3 instruction supports, without limitation, multiple SIMD variants, data types/sizes, or any combination thereof. In some embodiments, each no SIMD variant of the VIADD instruction, VIADDMNMX instruction, and VIMNMX3 operates on 32-bit integers to generate a single 32-bit result. In the same or other embodiments, each 2-way SIMD variant of the VIADD instruction, VIADDMNMX instruction, and VIMNMX3 instruction operates on 16-bit integers to generate two 16-bit integers packed in a 32-bit result. In some embodiments, a 4-way SIMD variant of the SW instruction 610 operates on 8-bit integers to generate four 8-bit integers packed in a 32-bit result.

In some embodiments, the VIADD is an integer add instruction that is executed in a floating point (FP) pipeline of the SM 310. Advantageously, in some embodiments, the SM 310 can issue and execute integer instructions in parallel with floating-point instructions. Consequently, executing the VIADD instruction in the FP pipeline can increase overlapping/pipelining of multiple instructions and therefore overall computational throughput.

As shown, in some embodiments, a VIADD instruction format 710 is "VIADD{.fmt} result, source_a, {-}source_b." Accordingly, each VIADD instruction includes, without limitation, an instruction name of "SW," an optional .fmt modifier, a result, a source_a, and a source_b that is optionally negated. Result is the destination operand and the instruction result. Source_a and source_b are the source operands. In some embodiments, allowed values for the .fmt modifier include, without limitation, 0.32, 0.16×2, and 0.8×4 corresponding to one 32-bit integer (no SIMD), packed data that includes two 16-bit integers (2-way SIMD), and packed data that includes four eight-bit integers (4-way SIMD), respectively. The VIADD instruction can cause the SM 310 to implement result=source_a+{-}source_b in any technically feasible fashion.

In some embodiments, the VIADD instruction causes the SM 310 to set each element in the result equal to the sum of the corresponding element in source_a and the optionally negated corresponding element in source_b. If the .fmt modifier is 0.32, then result, source_a, and source_b each include one element that is a 32-bit integer. If the .fmt modifier is 0.16, then result, source_a, and source_b each include two elements that are each a 16-bit integer. If the .fmt modifier is 0.8, then result, source_a, and source_b each include four elements that are each an 8-bit integer.

In the same or other embodiments, operations that can be performed by the SM 310 to execute the VIADD instruction are illustrated by the following exemplary pseudocode (8):

(8)
```
VIADD{.fmt} result, source_a, {-}source_b
// .fmt: .32, .16x2, .8x4
// result: instruction result
// source_a: value a, source_b: value b
READ_SOURCE_DATA(*tmp, reg)
tmp = register[reg];
WRITE_DESTINATION_DATA(*tmp, reg, size)
    register[reg] = *tmp;
switch(inst.fmt) {
    case .32:   ELEMENTS = 1; WIDTH = 32; break;
    case .16x2: ELEMENTS = 2; WIDTH = 16; break;
    case .8x4:  ELEMENTS = 4; WIDTH = 8;  break; }
uint32_t MASK = (1 << WIDTH) - 1;
uint32_t result = 0;
uint32_t sum, source_a, source_b;
READ_SOURCE_DATA(source_a, inst.source_a);
READ_SOURCE_DATA(source_b, inst.source_b);
for (uint i = 0; i < ELEMENTS; ++i) {
    int32_t bits a = (source_a >> (i * WIDTH)) & MASK;
    int32_t bits b = (source_b >> (i * WIDTH)) & MASK;
```

-continued
```
    if ( inst.negB ) b = (-b & MASK);
    sum = a + b;
    result |= (sum & MASK) << (WIDTH * i);
}
WRITE_DESTINATION_DATA(result, inst.result);
```

In some embodiments, the VIADDMNMX instruction is an integer add, minimum/maximum optionally performed against zero instruction that is executed in an integer pipeline of the SM 310. Notably, the VIADDMNMX instruction combines multiple conventional instructions into a single instruction. As shown, in some embodiments, a VIADDMNMX instruction format 720 is "VIADDMNMX{.fmt}{.relu} result, source_a, {-}source_b, source_c, min_or_max." Accordingly, each VIADDMNMX instruction includes, without limitation, an instruction name of "VIADDMNMX," an optional .fmt modifier, an optional .relu modifier, a result, a source_a, a source_b that is optionally negated, a source_c, and an optional min_or_max specifier. Result is the destination operand and the instruction result. Source_a, source_b, and source_c are the source operands. The min_or_max specifier specifies whether the VIADDMNMX instruction performs a minimum or maximum comparison(s). In some embodiments, allowed values for the .fmt modifier include, without limitation, ".U32," ".S32," ".U16×2," "S16×2, ".U16×2," ".S16×2," ".U8×4," and "0.S8×4" corresponding to one 32-bit unsigned integer, one 32-bit signed integer, packed data that includes two 16-bit unsigned integers, packed data that includes two 16-bit signed integers, packed data that includes four eight-bit unsigned integers, and packed data that includes four eight-bit signed integers, respectively. In the same or other embodiments, if the optional .relu modifier is present, then the VIADDMNMX instruction performs maximum/minimum operations against 0.

In some embodiments, the VIADDMNMX instruction causes the SM 310 to set each element in the result equal to the minimum or maximum of the corresponding element in source_c, the sum of the corresponding element in source_a and the optionally negated corresponding element in source_b, and optionally zero. If the .fmt modifier is 0.32, then result, source_a, source_b, and source_c each include one element that is a 32-bit integer. If the .fmt modifier is 0.16, then result, source_a, source_b, and source_c each include two elements that are each a 16-bit integer. If the .fmt modifier is 0.8, then result, source_a, source_b, and source_c each include four elements that are each an 8-bit integer.

In the same or other embodiments, operations that can be performed by the SM 310 to execute the VIADDMNMX instruction are illustrated by the following exemplary pseudocode (8):

(9)
```
VIADDMNMX{.fmt}{.relu} result, source_a, {-}source_b, source_c
            min_or_max
// .fmt: .U32, .S32, .U16x2, .S16x2, .U8x4, .S8x4
// .relu: if present performs MAX/MIN operations against value 0
// result: instruction result
// source_a: value a, source_b: value b, source_c: value c
MIN_MAX(value1, value2, width, min, signed)
    uint32_t MASK = (1 << width) - 1;
    if (signed) {
        uint32_t SIGN_EXT = ~MASK;
        uint32_t SIGN_BIT = 1 << (width - 1);
        int32_t a_int = (int)(a & MASK);
        int32_t b_int = (int)(b & MASK);
        if (a_int & SIGN_BIT) a_int |= SIGN_EXT;
        if (b_int & SIGN_BIT) b_int |= SIGN_EXT;
```

-continued

```
      int result;
      if (min)
         result = a_int < b_int ? a_int: b_int; else
         result = a_int >= b_int ? a_int: b_int; return result & MASK;
      } else {
         a &= MASK;
         b &= MASK;
         int result;
         if (min)
            result = a < b ? a : b;
         else
            result = a >= b ? a : b;
         return result;
      }
   switch(inst.fmt) {
      case .S32:   ELEMENTS = 1; SIGNED = true;  WIDTH = 32; break;
      case .S16x2: ELEMENTS = 2; SIGNED = true;  WIDTH = 16; break;
      case .S8x4:  ELEMENTS = 4; SIGNED = true;  WIDTH = 8;  break;
      case .U32:   ELEMENTS = 1; SIGNED = false; WIDTH = 32; break;
      case .U16x2: ELEMENTS = 2; SIGNED = false; WIDTH = 16; break;
      case .U8x4:  ELEMENTS = 4; SIGNED = false; WIDTH = 8;  break; }
   uint32_t MASK = (1 << WIDTH) - 1;
   uint32_t result = 0;
   uint32_t sum, comparison, source_a, source_b, source_c;
   READ_SOURCE_DATA(source_a, inst.source_a); // Function defined in (7)
   READ_SOURCE_DATA(source_b, inst.source_b); // Function defined in (7)
   READ_SOURCE_DATA(source_c, inst.source_c); // Function defined in (7)
   for (uint i = 0; i < ELEMENTS; ++i) {
      int32_t bits a = (source_a >> (i * WIDTH)) & MASK;
      int32_t bits b = (source_b >> (i * WIDTH)) & MASK;
      int32_t bits c = (source_c >> (i * WIDTH)) & MASK;
      if ( inst.negB ) b = (-b & MASK);
      sum = (a + b) & MASK;
      comparison = MIN_MAX(sum, c, WIDTH, min_or_max, SIGNED);
      if (inst.relu)
         comparison = MIN_MAX(comparison, 0, WIDTH, False, True);
      result |= comparison << (WIDTH * i);
   }
   WRITE_DESTINATION_DATA(result, inst.result);
```

In some embodiments, the VIMNMX3 instruction is an integer three-operand minimum/maximum optionally performed against zero instruction that is executed in an integer pipeline of the SM 310. Notably, the VIMNMX3 instruction adds at least a third operand to a conventional minimum/maximum instruction. As shown, in some embodiments, a VIMNMX3 instruction format 730 is "VIMNMX3{.fmt}{.relu} result, source_a, source_b, source_c, min_or_max." Accordingly, each VIMNMX3 instruction includes, without limitation, an instruction name of "VIMNMX3," an optional .fmt modifier, an optional .relu modifier, a result, a source_a, a source_b, a source_c, and an optional min_or_max specifier. Result is the destination operand and the instruction result. Source_a, source_b, and source_c are the source operands. The min_or_max specifier specifies whether the VIMNMX3 instruction computes the minimum or maximum of source_a, source_b, and source_c. In some embodiments, allowed values for the .fmt modifier include, without limitation, ".U32," ".S32," ".U16×2," ".S16×2, ".U16×2," ".S16×2," ".U8×4," and "0.58×4" corresponding to one 32-bit unsigned integer, one 32-bit signed integer, packed data that includes two 16-bit unsigned integers, packed data that includes two 16-bit signed integers, packed data that includes four eight-bit unsigned integers, and packed data that includes four eight-bit signed integers, respectively. In the same or other embodiments, if the optional .relu modifier is present, then the VIMNMX3 instruction performs maximum/minimum operations against 0.

In some embodiments, the VIMNMX3 instruction causes the SM 310 to set each element in the result equal to the minimum or maximum of the corresponding element in source_a, the corresponding element in source_b, the corresponding element in source_c, and optionally 0. If the .fmt modifier is 0.32, then result, source_a, source_b, and source_c each include one element that is a 32-bit integer. If the .fmt modifier is 0.16, then result, source_a, source_b, and source_c each include two elements that are each a 16-bit integer. If the .fmt modifier is 0.8, then result, source_a, source_b, and source_c each include four elements that are each an 8-bit integer.

In some embodiments, operations that can be performed by the SM 310 to execute the VIMNMX3 instruction are illustrated by the following exemplary pseudocode (10):

(10)
```
VIMNMX3{.fmt}{.relu} result, source_a, source_b, source_c, min_or_max
   // .fmt: .U32, .S32, .U16x2, .S16x2, .U8x4, .S8x4
   // .relu: if present performs MAX/MIN operations against value 0
   // result: instruction result
   // source_a: value a, source_b: value b, source_c: value c
   // Uses READ_SOURCE_DATA and WRITE_DESTINATION_DATA defined
```

```
// above in (7)
// Uses MIN_MAX defined above in (8)
switch(inst.fmt) {
    case .S32:   ELEMENTS = 1; SIGNED = true;  WIDTH = 32; break;
    case .S16x2: ELEMENTS = 2; SIGNED = true;  WIDTH = 16; break;
    case .S8x4:  ELEMENTS = 4; SIGNED = true;  WIDTH = 8;  break;
    case .U32:   ELEMENTS = 1; SIGNED = false; WIDTH = 32; break;
    case .U16x2: ELEMENTS = 2; SIGNED = false; WIDTH = 16; break;
    case .U8x4:  ELEMENTS = 4; SIGNED = false; WIDTH = 8;  break; }
uint32_t MASK = (1 << WIDTH) - 1;
uint32_t result = 0;
uint32_t tmp;
READ_SOURCE_DATA(source_a, inst.source_a);
READ_SOURCE_DATA(source_b, inst.source_b);
READ_SOURCE_DATA(source_c, inst.source_c);
for (uint i = 0; i < ELEMENTS; ++i) {
    int32_t bits a = (source_a >> (i * WIDTH)) & MASK;
    int32_t bits b = (source_b >> (i * WIDTH)) & MASK;
    int32_t bits c = (source_c >> (i * WIDTH)) & MASK;
    tmp = MIN_MAX(a, b, WIDTH, min, SIGNED);
    tmp = MIN_MAX(tmp, c, WIDTH, min, SIGNED);
    if (inst.relu)
        tmp = MIN_MAX(tmp, 0, WIDTH, False, True);
    result |= (tmp & MASK) << (WIDTH * i);
}
WRITE_DESTINATION_DATA(result, inst.result);
```

In some embodiments, because no, 2-way, and 4-way SIMD variants are supported for the VIADD instruction, the VIADDMNMX instruction, and the VIMNMX3 instruction, each of a no SIMD SW sequence 742, a 2-way SIMD SW sequence 744, and a 4-way SIMD SW sequence 746 includes, without limitation, six instructions. In some other embodiments, the SW sequence 740 includes, without limitation, six instructions for each SIMD variant that is supported across the VIADD instruction, the VIADDMNMX instruction, and the VIMNMX3 instruction.

The no SIMD SW sequence 742, 2-way SIMD SW sequence 744, and the 4-way SIMD SW sequence 746 are different variations of the SW sequence 740. In some embodiment, irrespective of the SIMD variant, the SW sequence 740 is a sequence of six instructions. In some embodiments, the SW sequence 740 is a first VIADD instruction that executes in the FP pipeline, a first VIADDMNMX instruction that executes in the integer pipeline, a second VIADD instruction that executes in the FP pipeline, a second VIADDMNMX instruction that executes in the integer pipeline, a third VIADD instruction that executes in the FP pipeline, and a VIMNMX3.RELU instruction that executes in the integer pipeline. As described previously herein, in some embodiments, executing the three VIADD instructions in the FP pipeline and executing the other three instructions in the integer pipeline can increase overlapping/pipelining of multiple instructions and therefore overall computational throughput.

The no SIMD SW sequence 742 depicted in FIG. 7 is an exemplary instruction sequence that operates on 32-bit data to generate sub-alignment data associated with a single position for a single local alignment problem. As shown, in some embodiments, a first VIADD.32 instruction in the no SIMD SW sequence 742 executes in the integer pipeline and sets temp1 equal to E_top+gde. A first VIADDMNMX.S32 in the no SIMD SW sequence 742 instruction executes in the FP pipeline and sets E equal to the maximum of (H_top+gde) and temp1. A second instruction VIADD.32 instruction in the no SIMD SW sequence 742 executes in the integer pipeline and sets temp2 equal to F_left+gie. A second VIADDMNMX.S32 instruction in the no SIMD SW sequence 742 executes in the integer pipeline and sets F equal to the maximum of (H_left+gie) and temp2. A third VIADD.32 instruction in the no SIMD SW sequence 742 executes in the integer pipeline and sets temp3 equal to H_diag+S. A VIMNMX3.S32.RELU instruction in the no SIMD SW sequence 742 executes in the FP pipeline and sets H equal to the maximum of temp1, temp2, temp3, and 0.

The 2-way SIMD SW sequence 744 depicted in FIG. 7 is an exemplary instruction sequence that operates on 16-bit data to generate sub-alignment data associated with a single position and two local alignment problems. Relative to the no SIMD SW sequence 742, the no SIMD instruction variants VIADD.32, VIADDMNMX.S32, and VIMNMX3.S32.RELU are replaced with the 2-way SIMD instruction variants VIADD.16X2, VIADDMNMX.S16X2, and VIMNMX3.S16X2.RELU, respectively.

The 4-way SIMD SW sequence 746 depicted in FIG. 7 is an exemplary instruction sequence that operates on 8-bit data to generate sub-alignment data associated with a single position and four local alignment problems. Relative to the no SIMD SW sequence 742, the no SIMD instruction variants VIADD.32, VIADDMNMX.S32, and VIMNMX3.S32.RELU are replaced with the 4-way SIMD instruction variants VIADD.8X4, VIADDMNMX.8X4, and VIMNMX3.8X4.RELU, respectively.

Advantageously, and as depicted in a SW sequence improvement table 790, the SW sequence 740 requires fewer instructions and fewer cycles than a conventional 10-instruction sequence to compute sub-alignment data associated with a single position in a scoring matrix. For explanatory purposes, in the context of FIG. 7, the required number of cycles described herein is based on embodiments having a one cycle per instruction throughput. In other embodiments, the cycle throughput for instructions and therefore the required number of cycles can vary.

As shown, in some embodiments, to compute sub-alignment data associated with a single position in a scoring matrix for a single local alignment problem (corresponding to a no SIMD variant), a conventional 10-instruction sequence requires ten instructions and ten cycles, and the no SIMD SW sequence 742 requires six instructions and six cycles. Relative to a conventional 10-instruction sequence, the no SIMD SW sequence 742 can therefore require 40% fewer instructions and 40% fewer cycles.

In some embodiments, to compute sub-alignment data associated with a single position in a scoring matrix for two local alignment problems (corresponding to a 2-way SIMD variant), a conventional 10-instruction sequence requires twenty instructions and twenty cycles, and the 2-way SIMD SW sequence 744 requires six instructions and six cycles. Relative to a conventional 10-instruction sequence, the 2-way SIMD SW sequence 744 can therefore require 70% fewer instructions and 70% fewer cycles.

In some embodiments, to compute sub-alignment data associated with a single position in a scoring matrix for four local alignment problems (corresponding to a 4-way SIMD variant), a conventional 10-instruction sequence requires thirty instructions and thirty cycles, and the 4-way SIMD SW sequence 746 requires six instructions and six cycles. Relative to a conventional 10-instruction sequence, the 4-way SIMD SW sequence 746 can therefore require 80% fewer instructions and 80% fewer cycles.

In some embodiments, including the embodiments depicted in FIG. 7, the source operands and the destination operands of the VIADD, VIADDMNMX, and VIMNMX3 instructions are compatible with both the interleaved cell layout 450(0) of FIG. 4 and the interleaved cell layout 450(1) of FIG. 5. In some embodiments, the SW kernel 192 executes the SW sequence 740 that includes, without limitation, VIADD, VIADDMNMX, and VIMNMX3 instructions specifying one or more operands included in one or more SWcells 460. In some other embodiments, the SW kernel 192 executes the SW sequence 740 that includes, without limitation, VIADD, VIADDMNMX, and VIMNMX3 instructions specifying one or more operands included in one or more the HEcells 560.

In some embodiments, the SW kernel 192, one or more other kernels, one or more SW libraries, or any combination thereof include, without limitation, one or more intrinsic functions that compute sub-alignment data corresponding to various portions (e.g., single position, row, row segments, entirety) of scoring matrices for any number of SIMD variants based on the SW instruction 610 and the interleaved cell layout 450(0), the SW sequence 740 and the interleaved cell layout 450(0), the SW sequence 740 and the interleaved cell layout 450(1), or any combination thereof.

Note that the techniques described herein are illustrative rather than restrictive and can be altered without departing from the broader spirit and scope of the invention. Many modifications and variations on the functionality provided by the SM 310, the VIADD instruction, the VIADDMNMX instruction, the VIMNMX3 instruction, the SW sequence 740, the no SIMD SW sequence 742, the 2-way SIMD SW sequence 744, the 4-way SIMD SW sequence 746, and the SW kernel 192 will be apparent to those of ordinary skill in the art without departing from the scope and spirit of the described embodiments. For instance, in some other embodiments, variants of the SW sequence 740 use a conventional add instruction that executes in the integer pipeline instead of the VIADD instruction. In the same or other embodiments, the no SIMD SW sequence 742, the 2-way SIMD SW sequence 744, and the 4-way SIMD SW sequence 746 can operate on 32-bit integers, two packed 16-bit integers, and four packed 8-bit integers, respectively, that are are associated with neither the interleaved cell layout 450(0) nor the interleaved cell layout 450(1).

Figure 8:
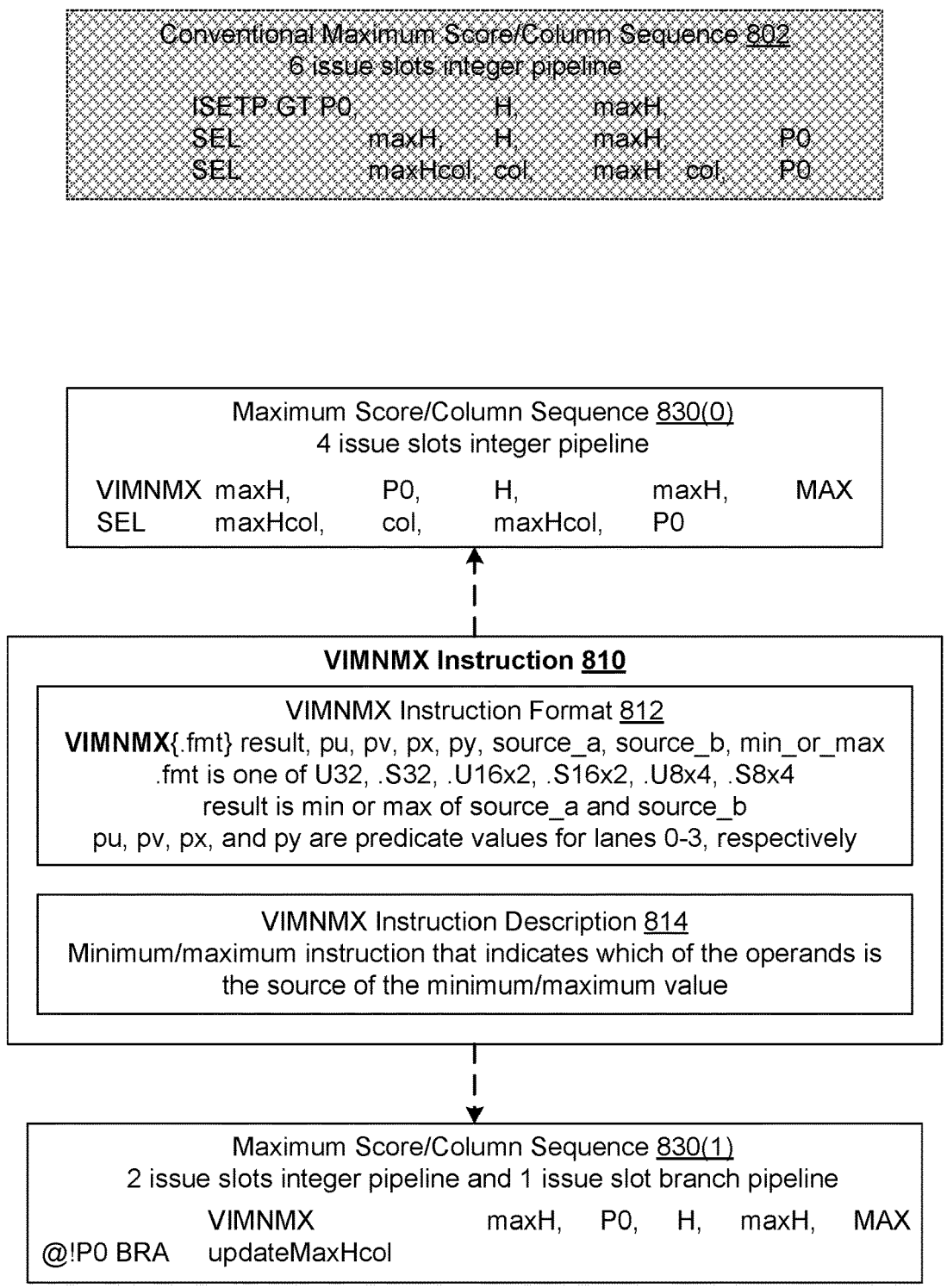
FIG. 8 illustrates a minimum/maximum value and corresponding source indicator instruction that is executed by the Smith-Waterman kernel of FIG. 1, according to various embodiments.

FIG. 8 illustrates a minimum/maximum value and corresponding source indicator instruction that is executed by the SW kernel 192 of FIG. 1, according to various embodiments. The minimum/maximum value and corresponding source indicator instruction is a VIMNMX instruction 810. In some embodiments, the SW kernel 192 uses the VIMNMX instruction 810 to determine a maximum sub-alignment score and a corresponding maximum scoring column (in the scoring matrix) and/or a corresponding maximum scoring row (in the scoring matrix) for each of any number of local sequence alignment problems.

Some conventional approaches to determining the maximum sub-alignment score and the maximum scoring position for a single local sequence alignment problem involves executing a conventional maximum score/column sequence 802 or similar instruction sequence for each sub-alignment score. As shown, the conventional maximum score/column sequence 802 is a three-instruction sequence. The first instruction is a ISETP.GT instruction that determines whether a current score (denoted as H) is greater than a maximum score (denoted as maxH) and writes the comparison result (denoted as P0) to a predicate register. The second instruction is a SEL instruction that overwrites the maximum score with the current score if the predicate indicates that the maximum score was updated. The third instruction is a SEL instruction that overwrites a maximum scoring column (denoted as maxHcol) with a current column (denoted as col) if the predicate indicates that the maximum score was updated.

As shown, executing the conventional maximum score/column sequence 802 requires 3 instructions and six issue slots in the integer pipeline. Although not shown, relative to the conventional maximum score/column sequence 802, determining the maximum sub-alignment score and the corresponding maximum scoring column for the additional local sequence alignment problem corresponding to 2-way SIMD requires additional instructions and additional issue slots in the integer pipeline. And determining the maximum sub-alignment score and the corresponding maximum scoring column for the additional local sequence alignment problems corresponding to 4-way SIMD requires yet more instructions and yet more issue slots in the integer pipeline.

In some embodiments, and as depicted via a VIMNMX instruction description 814, the VIMNMX instruction 810 is a per-thread minimum/maximum instruction that indicates which of the operands is the source of the minimum/maximum value. In the same or other embodiments, the VIMNMX instruction 810 provides a predicate to indicates which of the operands is the source of the minimum/maximum value. Subsequent instructions can use the predicate to select and store multiple values based on predicate. Advantageously, the VIMNMX instruction 810 can be used to optimize many software applications that store multiple values based on a conventional comparison instruction. In some embodiments, the SW instruction 610 supports, without limitation, multiple SIMD variants, data types/sizes, or any combination thereof.

As shown, in some embodiments, a VIMNMX instruction format 812 is "VIMNMX{.fmt} result, pu, pv, px, py, source_a, source_b, min_or_max." Accordingly, each VIMNMX instruction 810 includes, without limitation, an instruction name of "VIMNMX"; an optional .fmt modifier; result, pu, pv, px, py, source_a, source_b, and a min_or_max specifier. In some embodiments, result is the destination operand, source_a and source_b are source operands, and the min_or_max specifier specifies whether the VIMNMX instruction computes the minimum or maximum of source_a and source_b.

In some embodiments, pu, pv, px, and py are predicate values for lanes 0-3, respectively. In the same or other embodiments, allowed values for the .fmt modifier include, without limitation, ".U32," ".S32," ".U16×2," ".S16×2, ".U16×2," ".S16×2," ".U8×4," and ".S8×4" corresponding to one 32-bit unsigned integer, one 32-bit signed integer, two packed 16-bit unsigned integers, two packed 16-bit signed integers, four packed eight-bit unsigned integer, and four packed eight-bit signed integers, respectively.

In some embodiments, VIMNMX.U32 and VIMNMX.S32 instructions are no SIMD variants of the VIMNMX instruction 810 that set the result equal to the minimum/maximum of source_a and source_b, and indicate whether source_b is the minimum/maximum via the predicate value pu. In the same or other embodiments, VIMNMX.U32 and VIMNMX.S32 instructions do not use pv, px, and py. In some embodiments, pv, px, and py can be omitted from VIMNMX.U32 and VIMNMX.S32 instructions.

In some embodiments, VIMNMX.U16×2 and VIMNMX.S16×2 instructions are 2-way SIMD variants of the VIMNMX instruction 810 that set the first 16 bits of result equal to the minimum/maximum of the first 16 bits of source_a and the first 16 bits of source_b; indicate whether the first 16 bits of source b is the minimum/maximum via the predicate pu; set the last 16 bits of result equal to the minimum/maximum of the last 16 bits of source_a and the last 16 bits of source_b; and indicate whether the last 16 bits of source_b is the minimum/maximum via the predicate pv. In the same or other embodiments, VIMNMX.U16×2 and VIMNMX.S16×2 instructions do not use px and py. In some embodiments, px and py can be omitted from VIMNMX.U16×2 and VIMNMX.S16×2.

In the same or other embodiments, VIMNMX.U8×4 and VIMNMX.S8×4 instructions are 4-way SIMD variants of the VIMNMX instruction 810 that determines the packed 8-bit integers corresponding to lanes 0-3 in result and the predicate values pu, pv, px, py, respectively, based on the result based on the packed 8-bit integers corresponding to lanes 0-3, respectively, in source_a and the packed 8-bit integers corresponding to lanes 0-3, respectively, in source_b.

Each SM 310 can issue and execute VIMNMX instruction 810 in any technically feasible fashion. In some embodiments, operations that can be performed by the SM 310 to execute VIMNMX instruction 810 are illustrated by the following exemplary pseudocode (11):

```
// VIMNMX{.fmt} result, pu, pv, px, py, source_a, source_b, min_or_max
//.fmt: .U32, .S32, .U16x2, .S16x2, .U8x4, .S8x4
// result: instruction result
// pu: predicate value for lane 0, pv: predicate value for lane 1
// px: predicate value for lane 2, py: predicate value for lane 3
// source_a: value a, source_b: value b
READ_SOURCE_DATA(*tmp, reg)
   tmp = register[reg]
WRITE_DESTINATION_DATA(*tmp, reg, size)
   register[reg] = *tmp
PRED_WRITE(*tmp, preg)
   if (preg == PT)
      return;
   predicate_register &= ~(1 << preg);
   predicate_register |= (tmp & 0x1) << preg;
MIN_MAX(value1, value2, width, min, signed)
   uint32_t MASK = (1 << width) - 1;
   if (signed) {
      uint32_t SIGN_EXT = ~MASK;
      uint32_t SIGN_BIT = 1 << (width - 1);
      int32_t a_int = (int)(a & MASK);
      int32_t b_int = (int)(b & MASK);
      if (a_int & SIGN_BIT) a_int |= SIGN_EXT;
      if (b_int & SIGN_BIT) b_int |= SIGN_EXT;
      int result;
      if (min)
         result = a_int < b_int ? a_int: b_int;
      else
         result = a_int >= b_int ? a_int: b_int;
      return result & MASK;
   } else {
      a &= MASK;
      b &= MASK;
      int result;
      if (min)
         result = a < b ? a : b;
      else
         result = a >= b ? a : b;
      return result;
   }
switch(inst.fmt) {
   case .S32:   ELEMENTS = 1; SIGNED = true; WIDTH = 32; break;
   case .S16x2: ELEMENTS = 2; SIGNED = true; WIDTH = 16; break;
   case .S8x4:  ELEMENTS = 4; SIGNED = true; WIDTH = 8;  break;
   case .U32:   ELEMENTS = 1; SIGNED = false; WIDTH = 32; break;
   case .U16x2: ELEMENTS = 2; SIGNED = false; WIDTH = 16; break;
   case .U8x4:  ELEMENTS = 4; SIGNED = false; WIDTH = 8;  break;
uint32_t MASK = (1 << WIDTH) - 1;
uint32_t result = 0;
bool pu = false, pv = false, px = false, py = false;
```

```
    READ_SOURCE_DATA(source_a, inst.source_a);
    READ_SOURCE_DATA(source_b, inst.source_b);
    for (uint i = 0; i < ELEMENTS; ++i) {
        int32_t bits a = (source_a >> (i * WIDTH)) & MASK;
        int32_t bits b = (source_b >> (i * WIDTH)) & MASK;
        tmp = MIN_MAX(a, b, WIDTH, min, SIGNED);
        if (inst.relu)
            tmp = MIN_MAX(tmp, 0, WIDTH, False, True);
        if (i == 0) pu = (tmp == a);
        if (i == 1) pv = (tmp == a);
        if (i == 2) px = (tmp == a);
        if (i == 3) py = (tmp == a);
        result |= (tmp & MASK) << (WIDTH * i);
    }
    WRITE_DESTINATION_DATA(result, inst.result);
    PRED_WRITE(pu, inst.Pu);
    PRED_WRITE(pv, inst.Pu);
    PRED_WRITE(px, inst.Px);
    PRED_WRITE(py, inst.Py);
```

In some embodiments, the SW kernel 192 implements a maximum score/column sequence 830(0) to determine a maximum sub-alignment score and the corresponding maximum scoring column (in the scoring matrix) when computing sub-alignment scores row-by-row for each of any number of local sequence alignment problems.

As shown, the maximum score/column sequence 830(0) is a two-instruction sequence. The first instruction is VIMNMX instruction 810 that overwrites a maximum score (denoted as maxH) with a current score (denoted as H) if the current score is greater than the maximum score and writes a comparison result (denoted as P0) indicating whether the maximum score was updated to a predicate register. The second instruction is a SEL instruction that that overwrites a maximum scoring column (denoted as maxHcol) with a current column (denoted as col) if the predicate indicates that the maximum score was updated.

As shown, executing the maximum score/column sequence 830(0) requires 2 instructions. Relative to the conventional maximum score/column sequence 802, the maximum score/column sequence 830(0) requires one fewer instruction. Although not shown, relative to two conventional maximum score/column sequences, using a 2-way SIMD variant of the VIMNMX instruction 810 can require 3 fewer instructions. And relative to four conventional maximum score/column sequences, using a 4-way SIMD variant of the VIMNMX instruction 810 can require 5 fewer instructions.

In some other embodiments, the SW kernel 192 implements a maximum score/column sequence 830(1) to determine a maximum sub-alignment score and the corresponding maximum scoring column (in the scoring matrix) when computing sub-alignment scores row-by-row for each of any number of local sequence alignment problems.

As shown, the maximum score/column sequence 830(1) is a two-instruction sequence. The first instruction is VIMNMX instruction 810 that overwrites a maximum score (denoted as maxH) with a current score (denoted as H) if the current score is greater than the maximum score and writes a comparison result (denoted as P0) indicating whether the maximum score was updated to a predicate register. The second instruction is a predicated BRA instruction that branches to code (denoted as updateMaxHcol) that updates a maximum scoring column (denoted as maxHcol) with a current column (denoted as col) if the predicate indicates that the maximum score was updated.

As shown, executing the maximum score/column sequence 830(1) requires 2 issue slots in the integer pipeline, and 1 issue slot in a branch pipeline. Relative to the conventional maximum score/column sequence 802, the maximum score/column sequence 830(1) requires two fewer issue slots in the integer pipeline and can therefore increase an overall computational throughput. Although not shown, relative to two conventional maximum score/column sequences, using a 2-way SIMD variant of the VIMNMX instruction 810 can further increase the overall computation throughout. And relative to four conventional maximum score/column sequences, using a 4-way SIMD variant of the VIMNMX instruction 810 can further increase the overall computation throughout.

In general, the VIMNMX instruction 810 performs a minimum/maximum operation on 1-4 maximum "base" value(s) and provides 1-4 predicate(s) indicating the comparison result(s). As the maximum score/column sequences 830(0) and 830(1) illustrate, using the predicate(s) to save other value(s) based on the comparison result(s) can increase computational throughput when saving multiple values based on many types of conventional comparison instruction.

FIG. 9 is an example illustration of SW two problem pseudocode 910 that is executed by the SW kernel 192 of FIG. 1, according to various embodiments. For explanatory purposes, the SW two problem pseudocode 910 illustrates a matrix-filling phase in which each thread in the CTA 312 computes a sub-alignment score for each position in corresponding scoring matrix, a maximum sub-alignment score, a maximum scoring column, and a maximum scoring row for each of two local alignment problems. Because each thread computes sub-alignment scores for two local alignment problems, the thread computation SIMD mode is 2-way SIMD. Notably, the SW single problem pseudocode 1010 uses the interleaved cell layout 450(0), the SW instruction 610, and the VIMNMX instruction 810.

As per initialization pseudocode 920, the SW kernel 192 initializes a result set that resides in a register file and two arrays of (N+1) SWcell16s 464 that reside in the register file. The result set includes, without limitation, six 16-bit integers that correspond to a maximum sub-alignment score, a maximum scoring column, and a maximum scoring row for each of two local alignment problems.

The SW kernel 192 traverses a scoring matrix row-by-row, starting with the row after the initial initialization row. As described previously herein in conjunction with FIG. 4, the SW kernel 192 implements a current row/prior row swapping technique to reuse the two arrays of SWcells16s 464. Row identifier swap pseudocode 930 identifies the corresponding portion of the SW two problem pseudocode 910.

As per substitution value assignment pseudocode 940, for all columns except for the initialization columns in a current row, the SW kernel 192 copies two substitution values from the substitution matrix 444 to the proper SWcells16s 464. Advantageously, implementing a substitution value loop prior independently of a sub-alignment loop enables one warp to execute the substitution value loop using one set of instructions (e.g., load, etc.) while another warp is executing a main loop using another set of instructions (e.g., the SW.16 instruction, etc.).

As per a main loop of the SW two problem pseudocode 910, for all columns except for the initialization columns in a current row, the SW kernel 192 executes sub-alignment computation pseudocode 950 and result computation pseudocode 960. The sub-alignment computation pseudocode 950 is a call to an intrinsic function_SW_16 that is a wrapper for the 2-way SIMD variant (SW.2) of the SW instruction 610. Executing the SW.2 instruction causes the SM 310 to compute the sub-alignment data for the current row and the current column for the two assigned local alignment problems. Accordingly, the SW kernel 192 executes a single instruction to compute and store (in one of the SWcell16s 464 residing in the register file) two E values, two F values, and two sub-alignment scores.

As shown, the result computation pseudocode 960 includes, without limitation, a call to an intrinsic function_ vimnmx_16 that is a wrapper for a 2-way SIMD variant (VIMNMX.S16X2) of the VIMNMX instruction 810 followed by two sets of predicate-conditioned update pseudocode. Accordingly, the SW kernel 192 executes a single instruction to compute and store the two maximum sub-alignment scores thus-far and and two predicate values, pu and pv. The SW kernel 192 then conditionally updates the maximum scoring column and the maximum scoring row for none, one, or both of the assigned local alignment problems based on pu and pv.

FIG. 10 is an example illustration of SW single problem pseudocode 1010 that is executed by the SW kernel 192 of FIG. 1, according to other various embodiments. For explanatory purposes, the SW single problem pseudocode 1010 illustrates a matrix-filling phase in which each thread in the CTA 312 computes a sub-alignment score for each position in corresponding scoring matrix, a maximum sub-alignment score, a maximum scoring column, and a maximum scoring row for a single local alignment problems. Because each thread computes sub-alignment scores for a single local alignment problem, the thread computation SIMD mode is no SIMD.

The SW single problem pseudocode 1010 uses the interleaved cell layout 450(1), SW sequence pseudocode 1002, and the VIMNMX instruction 810. As shown, the SW sequence pseudocode 1002 is an intrinsic function_sw6_1 that is a per-thread six-instruction sequence for a SW scoring computation for a thread computation mode of no SIMD thread, the matrix-filling dataset 490(1), and 32-bit signed integers. The per-thread six-instruction sequence is a specific variant of the SW sequence 740 that corresponds to the thread computation mode of no SIMD, the matrix-filling dataset 490(1), and 32-bit signed integers. As shown, the SW sequence pseudocode 1002 uses intrinsic functions_viadd,_ viaddmnmx, and_vimnmx3 that are wrappers for the VIADD.32 instruction, the VIADDMNMX.S32 instruction, and the VIMNMX3.S32 instruction, respectively to implement the no SIMD SW sequence 742 described previous herein in conjunction with FIG. 5 using 32-bit signed integers operands included in the matrix-filling dataset 490 (1).

Referring now to the SW single problem pseudocode 1010, as per initialization pseudocode 1020, the SW kernel 192 initializes a result set that resides in a register file, two arrays of (N+1) HEcell32s 562 that reside in the register file, an F array of (N+1) 32-bit integers, and an S array of N 32-bit integers. The result set includes, without limitation, three 32-bit integers that correspond to a maximum sub-alignment score, a maximum scoring column, and a maximum scoring row.

The SW kernel 192 traverses a scoring matrix row-by-row, starting with the row after the initial initialization row. As described previously herein in conjunction with FIG. 5, the SW kernel 192 implements a current row/prior row swapping technique to reuse the two arrays of HEcell32s 562. Row identifier swap pseudocode 1030 identifies the corresponding portion of the SW single problem pseudocode 1010.

As per substitution value assignment pseudocode 1040, for all columns except for the initialization columns in a current row, the SW kernel 192 copies a substitution value from the substitution matrix 444 to the S array. Advantageously, implementing a substitution value loop prior independently of a sub-alignment loop enables one warp to execute the substitution value loop using one set of instructions (e.g., load, etc.) while another warp is executing a main loop using another set of instructions (e.g., the VIADD.32 instruction, etc.).

As per a main loop of the SW single problem pseudocode 1010, for all columns except for the initialization columns in a current row, the SW kernel 192 executes sub-alignment computation pseudocode 1050 and result computation pseudocode 1060. The sub-alignment computation pseudocode 1050 is a call to an intrinsic function_sw6_1 described above in conjunction with the SW single problem pseudocode 1010. Executing the intrinsic function_sw6_1 causes the SM 310 to execute a six-instruction sequence to compute and store, for the current row and the current column for the assigned local alignment problem, the E value and the sub-alignment score in one of the HEcell32s 562 and the F value in the F array.

As shown, the result computation pseudocode 1060 pseudocode includes, without limitation, a call to an intrinsic function_vimnmx_32 that is a wrapper for the no SIMD variant (VIMNMX.U32) of the VIMNMX instruction 810 followed by predicate-conditioned update pseudocode. Accordingly, the SW kernel 192 executes a single instruction to compute and store the maximum sub-alignment scores thus-far and and a predicate value pu. The SW kernel 192 then conditionally updates the maximum scoring column and the maximum scoring row of the assigned local alignment problems based on pu.

FIG. 11 illustrates how the instructions of FIGS. 6 and 9 are implemented in the execution units, according to various embodiments. As shown, an instruction implementation 1180 includes, without limitation, a VIADD implementation 1182, a VIADDMNMX implementation 1184, and a VIMNMX3 implementation 1186, and a VIMNMX implementation 1188. For explanatory purposes only, optional negations and .relu modifiers are disregarded with respect to FIG. 11.

Referring back to FIG. 3B, in some embodiments, a floating point execution unit 1110 and an integer execution unit 1130 are included in each of the core datapath units 350. In the same or other embodiments, the floating point execution unit 1110 and the integer execution unit 1130 are execution units. In some embodiments, instructions are decoded via instruction decoders included in the work distribution crossbar 316 and issued to execution units via the micro-schedule dispatch units 340 and/or the MIO control unit 370.

The VIADD implementation 1182 describes the implementation, in some embodiments, of the VIADD instruction described previous herein in conjunction with FIG. 11 with respect to an adder 1120 included in a example of the floating point execution unit 1110 that is implemented in a FP pipeline of the SM 310 in some embodiments. As shown, signals corresponding to the source operands source_a and source_b of the VIADD instruction are denoted herein as "A" and "B" and are input into the adder 1120. In response, the adder 1120 computes outputs a signal denoted as (A+B) that corresponds to the result of the VIADD instruction.

In some embodiments, the VIADDMNMX implementation 1184, the VIMNMX3 implementation 1186, and the VIMNMX implementation 1188 describe implementations of the corresponding instructions with respect to an exemplary portion of the integer execution unit 1130 that is implemented in an integer pipeline of the SM 310 in some embodiments. In some embodiments, the integer execution unit 1130 includes, without limitation, an adder 1140, a mux 1150, an adder 1160, and a mux 1170. An instruction control 1132 is routed to and controls the operation of each of the adder 1140, the mux 1150, the adder 1160, and the mux 1170.

Signals corresponding to the source operands source_a and source_b of each of the VIADDMNMX instruction, the VIMNMX3 instruction, and the VIMNMX instruction 810 are denoted herein as "A" and "B" and are input into the adder 1140. A signal corresponding to the source operand source_c of each of the VIADDMNMX instruction and the VIMNMX3 instruction is denoted herein as "C" is input into the adder 1160 and the mux 1170.

In some embodiments, as per the VIADDMNMX implementation 1184, the adder 1140 computes (A+B). The mux 1150 selects (A+B). The adder 1160 computes (A+B+C) and a control signal 1134(1). Based on the control signal 1134(1), the mux 1170 outputs the maximum or minimum of (A+B) and the signal C.

In some embodiments, as per the VIMNMX3 implementation 1186, the adder 1140 computes (A+B) and a control signal 1134(0). Based on the control signal 1134(0), the mux 1150 selects the minimum or maximum of A and B. The adder 1160 computes C+(minimum or maximum of A and B) and a control signal 1134(1). Based on the control signal 1134(1), the mux 1170 outputs the maximum or minimum of A, B, and C.

In some embodiments, as per the VIMNMX implementation 1188, the adder 1140 outputs (A+B) and the predicate values pu, pv, px, and py.

Figure 12A:
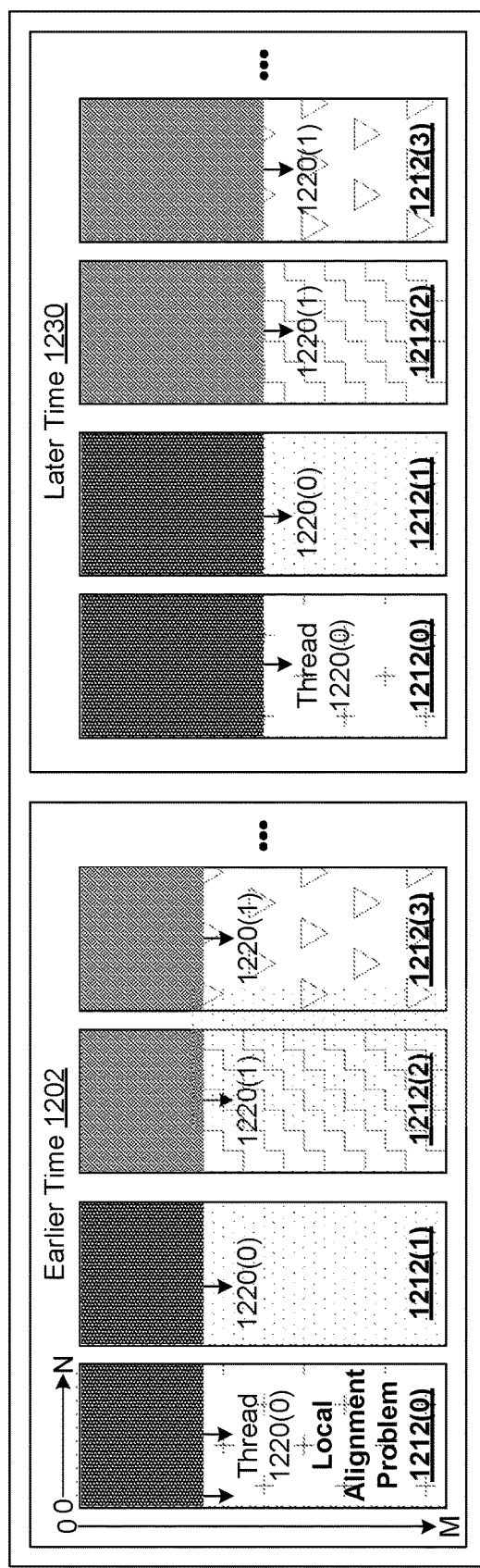
FIG. 12A is an example illustration of a 2-way single instruction multiple data (SIMD) matrix-filling phase that is executed by the cooperative thread array (CTA) of FIG. 3A, according to various embodiments.

FIG. 12A is an example illustration of a 2-way SIMD matrix-filling phase 1210(0) that is executed by the CTA 312 of FIG. 3A, according to various embodiments. More specifically, FIG. 12A illustrates an example of how the CTA 312 can apply a "multiple problems per thread" technique to execute a 2-way SIMD matrix-filling phase. In the multiple problems per thread techniques, each thread in the CTA 312 is assigned two different local alignment problems. For each local alignment problem, the assigned thread computes sub-alignment scores for each position in an associated scoring matrix in a row-by-row fashion, a maximum sub-alignment score, and a maximum scoring position that specifies the row and column of the maximum sub-alignment score in the scoring matrix.

In operation, a given thread initializes E0, E1, H0, and H1 values in each initial cell in an initial row 0 and F0, F1, H0, and H1 values in each initial cell in an initial column 0, where E0, F0, and H0 correspond to one of the assigned local alignment problems and E1, F1, and H1 correspond to the other assigned local alignment problem. The thread then sequentially computes E0, E1, H0, and H1 values for positions (1, 1)-(1, N+1) corresponding to a left-to-right traversal of row 1, updating one or both of each of the maximum sub-alignment scores and maximum scoring positions as appropriate. After traversing row 1, the thread sequentially computes E0, E1, H0, and H1 values for positions (2, 1)-(2, N+1) corresponding to a left-to-right traversal of row 2. The thread continues to process positions in the scoring matrix in this fashion until the thread finishes processing the (M, N) position in the scoring matrix. The thread then stores the maximum sub-alignment score and maximum scoring position for each of the assigned local alignment problems in global memory.

For explanatory purposes, incremental progress of a thread 1220(0) and a thread 1220(1) is depicted via two snapshots corresponding to an earlier time 1202 and a later time 1230. As shown, the thread 1220(0) processes a local alignment problem 1212(0) and a local alignment problem 1212(1). As shown, the thread 1220(1) processes a local alignment problem 1212(2) and a local alignment problem 1212(3).

At the earlier time 1202, the thread 1220(0) has processed a third of the rows in a scoring matrix (not shown) that is associated with the thread 1220(0) and the local alignment problems 1212(0) and 1212(1). The processed rows correspond to a third of the target symbols associated with the local alignment problem 1212(0) and a third of the target symbols associated with the local alignment problem 1212(1). At the earlier time 1202, the thread 1220(1) has processed a third of the rows in a scoring matrix (not shown) that is associated with the thread 1220(1) and the local alignment problems 1212(2) and 1212(3). The processed rows correspond to a third of the target symbols associated with the local alignment problem 1212(2) and a third of the target symbols associated with the local alignment problem 1212(3).

At the later time 1230, the thread 1220(0) has processed half of the rows in the scoring matrix that is associated with the thread 1220(0) and the local alignment problems 1212(0) and 1212(1). The processed rows correspond to half of the target symbols associated with the local alignment problem 1212(0) and half of the target symbols associated with the local alignment problem 1212(1). At the later time 1230, the thread 1220(1) has processed half of the rows in the scoring matrix that is associated with the thread 1220(1) and the local alignment problems 1212(2) and 1212(3). The processed rows correspond to half of the target symbols associated with the local alignment problem 1212(2) and half of the target symbols associated with the local alignment problem 1212(3).

Note that the techniques described herein are illustrative rather than restrictive and can be altered without departing from the broader spirit and scope of the invention. Many modifications and variations on the functionality provided by the software application 190, the SW kernel 192, the CTA 312, the parallel processing subsystem 112, the PPUs, the SMs, and the CPU will be apparent to those of ordinary skill in the art without departing from the scope and spirit of the described embodiments. Furthermore, many techniques can be used to traverse scoring matrices and any number of these techniques can be used in conjunction with any number of the techniques described previously herein.

Figure 12B:
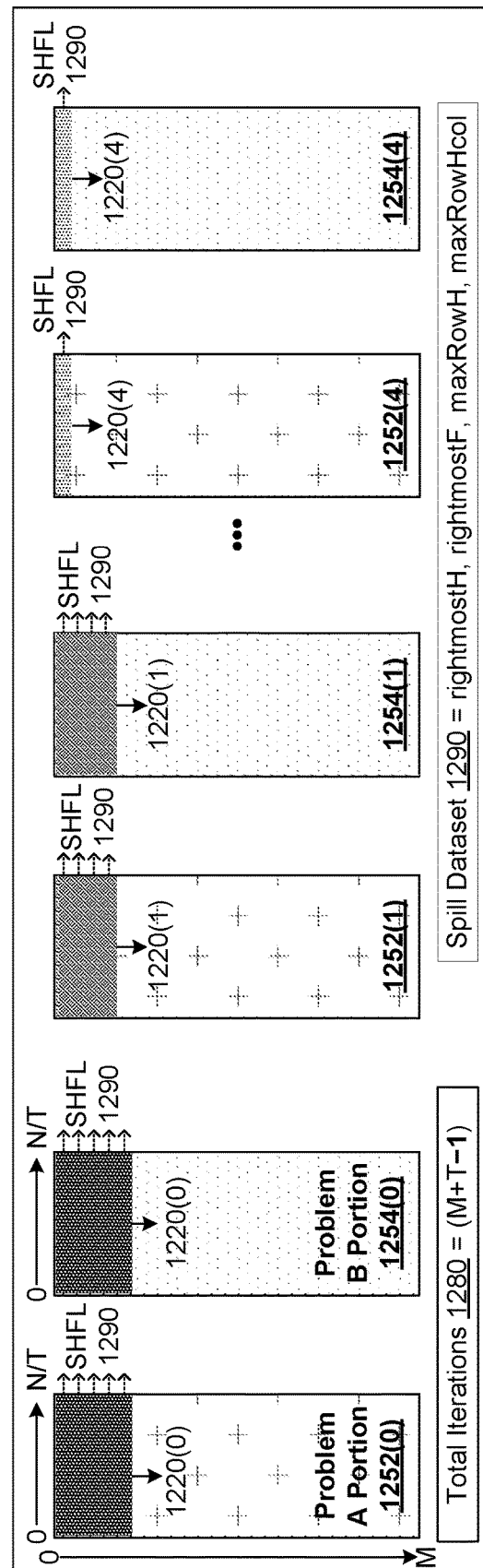
FIG. 12B is an example illustration of a 2-way SIMD matrix-filling phase that is executed by the CTA of FIG. 3A, according to other various embodiments.

FIG. 12B is an example illustration of a 2-way SIMD matrix-filling phase 1210(1) that is executed by the CTA 312 of FIG. 3A, according to other various embodiments. More specifically, FIG. 12A illustrates an example of how a warp in the CTA 312 can apply a "staggered thread" technique to execute a 2-way SIMD matrix-filling phase. In some embodiments, in the staggered thread technique, each warp in the CTA 312 is assigned two different local alignment problems. Each thread is assigned a set of columns based on the thread ID within the warp. The thread 1220(0) is assigned the columns 1-N/T, where T is the total number of threads in the warp (e.g., 32), the thread 1220(1) is assigned the columns (N/T+1)-(2*N/T), and so forth.

For explanatory purposes, the local alignment problems that are assigned to the warp depicted in FIG. 12B are referred to as "problem A" and "problem B." In some embodiments, the warp performs the matrix-filling phase for problems A and B over a total iterations 1280 that is equal to (M+T−1). Each thread participates in M iterations. For each thread, an initial iteration is equal to the thread ID, a final iteration is equal to (thread ID+M−1), and the thread processes the assigned columns in row 1 during the initial iteration, the assigned columns in row 2 during the next iteration, and so forth. In some embodiments, the SW kernel can implement the thread staggering describe herein via the following pseudocode (12):

```
for (iteration = 0 ; iteration <= last_iteration; ++iteration) {
    row = iteration − thread_ID + 1; // thread_ID from 0 to T−1
    if (row > 0 && row <= M) {
        // process assigned columns in row
    }
    // threads executing if statement above
    // and threads skipping if statement converge
```
(12)

In some embodiments, each thread initializes a different matrix-filling dataset that resides in an associated register file. Thread 1220(0) also initializes an initial H and an initial F associated with an initial column to zero. After processing each row, each of the threads 1220(0)-1220(T−2) provide a spill dataset 1290 to the thread having the next thread ID. The threads can provide the spill dataset 1290 in any technically feasible fashion. In some embodiments, the threads execute register-to-register data exchanges via warp shuffle instructions (e.g., SHFL_SYNC) to exchange the spill datasets 1290. In some embodiments, each warp shuffle instruction causes each of a subset of threads participating in the warp shuffle instruction to transfer data from a register associated with the thread to another register associated with another thread.

As shown, in some embodiments, each spill dataset 1290 includes, without limitation, a rightmostH, a rightmostF, a maxH, and a maxHCol. With respect to the thread that provides the spill dataset 1290, the rightmostH includes the H value(s) corresponding to the row and the last assigned column for the assigned local alignment problems, the rightmostF includes the F value(s) corresponding to the row and the last assigned column for the assigned local alignment problems, the maxH corresponds to the maximum sub-alignment score(s) in the row thus-far for the assigned local alignment problems, and the maxHcol specifies the column(s) corresponding to the maximum sub-alignment score(s) in the row thus-far.

In some embodiments, before processing each row, each of the threads 1220(1)-1220(T−1) performs initialization operations based on the spill dataset 1290 received by the thread 1220 for the row. In the same or other embodiments, the thread 1220(T−1) initializes and updates, as appropriate, maximum sub-alignment scores and maximum scoring positions for the assigned local alignment problems based on the spill datasets 1290 received from the thread 1220(T−2). After processing the last row, the thread 1220(T−1) stores the maximum sub-alignment score and the maximum scoring position for each of the assigned local alignment problems in global memory.

For explanatory purposes, FIG. 12B illustrates the progress of threads 1220(0)-1220(4) after the fifth iteration. Notably, the threads 1220(5)-1220(T−1) have not yet processed any rows. As shown, thread 1220(0) is assigned a problem A portion 1252(0) corresponding to the columns 1-(N/T) of the local alignment problem A and a problem B portion 1254(0) corresponding to the columns 1-(N/T) of the local alignment problem B. The thread 1220(1) is assigned a problem A portion 1252(1) and a problem B portion 1254(1), and so forth.

At the point-in-time depicted in FIG. 12B, the thread 1220(0) has processed rows 1-5 of problem A portion 1252(0) and rows 1-5 of problem B portion 1254(0) and exchanged spill datasets 1290 with the thread 1220(1) via warp shuffle operations. The thread 1220(1) has processed rows 1-4 of problem A portion 1252(1) and rows 1-4 of problem B portion 1254(1) and exchanged spill datasets 1290 with the thread 1220(2) via warp shuffle operations. Although not shown, thread 1220(2) has processed rows 1-3 of problem A portion 1252(2) and rows 1-3 of problem B portion 1254(2) and exchanged spill datasets 1290 with the thread 1220(3) via warp shuffle operations. The thread 1220(3) has processed rows 1-2 of problem A portion 1252(3) and rows 1-2 of problem B portion 1254(3) and exchanged spill datasets 1290 with the thread 1220(4) via warp shuffle operations. As shown, the thread 1220(4) has processed row 1 of problem A portion 1252(4) and row 1 of problem B portion 1254(4) and exchanged one of the spill datasets 1290 with the thread 1220(5) via a warp shuffle operation.

Note that the techniques described herein are illustrative rather than restrictive and can be altered without departing from the broader spirit and scope of the invention. Many modifications and variations on the functionality provided by the software application 190, the SW kernel 192, the CTA 312, the parallel processing subsystem 112, the PPUs, the SMs, and the CPU will be apparent to those of ordinary skill in the art without departing from the scope and spirit of the described embodiments. In one example, the staggered thread technique described herein for 2-way SIMD can be modified an applied to a 4-way SIMD matrix-filling phase and a no SIMD matrix-filling phase. In another example, in some embodiments, the staggered thread technique can is applied to half-warps instead of warps, where each half-warp is assigned a different set of 1, 2, or 4 local alignment problems.

Figure 13:
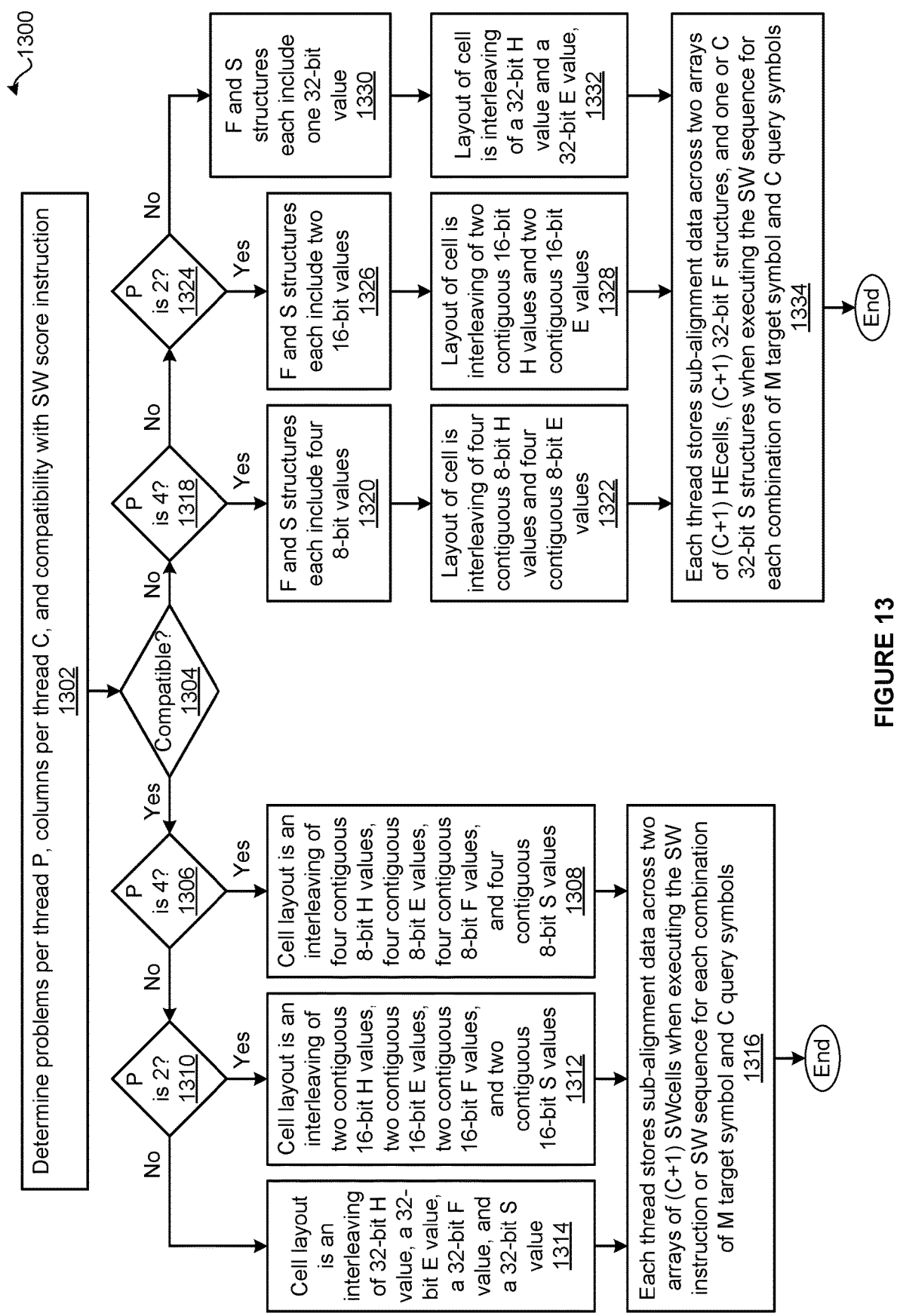
FIG. 13 is a flow diagram of method steps for storing sub-alignment data when executing a matrix-filling phase of a Smith-Waterman algorithm, according to various embodiments.

FIG. 13 is a flow diagram of method steps for storing sub-alignment data when executing a matrix-filling phase of a Smith-Waterman algorithm, according to various embodiments. Although the method steps are described with reference to the systems of FIGS. 1-12, persons skilled in the art will understand that any system configured to implement the method steps, in any order, falls within the scope of the present invention.

As shown, a method 1300 begins at step 1302, where a program (e.g., the software application 190 or the SW kernel 192) determines problems per thread 412 denoted as P, columns per thread 414 denoted as C, and whether an interleaved cell layout is to be compatible with the SW instruction 610. If, at step 1304, the program determines that the interleaved cell layout is to be compatible with the SW instruction 610, then the method 1300 proceeds to step 1306.

At step 1306, if the program determines that the problems per thread 412 is four, then the method 1300 proceeds to step 1308. At step 1308, the program determines that each cell layout is an interleaving of four contiguous 8-bit H values, four contiguous 8-bit E values, four contiguous 8-bit F values, and four contiguous 8-bit S values, and therefore each SWcell 460 is SWcell8 486. The method 1300 then proceeds directly to step 1316. At step 1316, the program causes each thread in one or more CTAs 312 to store sub-alignment data across two arrays of (C+1) SWcells 460 when executing the SW instruction 610 or the SW sequence 740 for each combination of C query symbols and M target symbols. The method 1300 then terminates.

If, however, at step 1306, if the program determines that the problems per thread 412 is not four, then the method 1300 proceeds directly to step 1310. At step 1310, if the program determines that the problems per thread 412 is two, then the method 1300 proceeds to step 1312. At step 1312, the program determines that each cell layout is an interleaving of two contiguous 16-bit H values, two contiguous 16-bit E values, two contiguous 16-bit F values, and two contiguous 8-bit S values, and therefore each SWcell 460 is SWcell16 484. The method 1300 then proceeds directly to step 1316. At step 1316, the program causes each thread in one or more CTAs 312 to store sub-alignment data across two arrays of (C+1) SWcells 460 when executing the SW instruction 610 or the SW sequence 740 for each combination of C query symbols and M target symbols. The method 1300 then terminates.

If, however, at step 1310, the program determines that the problems per thread 412 is not two, then the method 1300 proceeds directly to step 1314. At step 1314, the program determines that each cell layout is an interleaving of a 32-bit H value, a 32-bit E values, a 32-bit F value, and an 8-bit S value, and therefore each SWcell 460 SWcell32 482. The method 1300 then proceeds directly to step 1316. At step 1316, the program causes each thread in one or more CTAs 312 to store sub-alignment data across two arrays of (C+1) SWcells 460 when executing the SW instruction 610 or the SW sequence 740 for each combination of C query symbols and M target symbols. The method 1300 then terminates.

Referring back to step 1304, if at step 1304, the program determines that the interleaved cell layout is not to be compatible with the SW instruction 610, then the method 1300 proceeds directly to step 1318. At step 1318, if the program determines that the problems per thread 412 is four, then the method 1300 proceeds to step 1320. At step 1320, the program determines that each F structure 570 is to include four 8-bit F values and each S structure 580 is to include four 8-bit S values. At step 1322, the program determines that each cell layout is an interleaving of four contiguous 8-bit H values and four contiguous 8-bit E values, and therefore each HEcell 560 is SWcell8 566. The method 1300 then proceeds directly to step 1334. At step 1334, the program causes each thread in one or more CTAs 312 to store sub-alignment data across two arrays of (C+1) HEcells 560 when executing the SW sequence 740 for each combination of C query symbols and M target symbols. The method 1300 then terminates.

If, however, at step 1318, if the program determines that the problems per thread 412 is not four, then the method 1300 proceeds directly to step 1324. At step 1324, if the program determines that the problems per thread 412 is two, then the method 1300 proceeds to step 1326. At step 1326, he program determines that each F structure 570 is to include two 16-bit F values and each S structure 580 is to include two 16-bit S values. At step 1328, the program determines that each cell layout is an interleaving of two contiguous 16-bit H values and two contiguous 16-bit E values, and therefore each HEcell 560 is SWcell16 564. The method 1300 then proceeds directly to step 1334. At step 1334, the program causes each thread in one or more CTAs 312 to store sub-alignment data across two arrays of (C+1) HEcells 560 when executing the SW sequence 740 for each combination of C query symbols and M target symbols. The method 1300 then terminates.

If, however, at step 1324, if the program determines that the problems per thread 412 is not two, then the method 1300 proceeds directly to step 1330. At step 1330, he program determines that each F structure 570 is to include one 32-bit F value and each S structure 580 is to include one 32-bit S value. At step 1332, the program determines that each cell layout is an interleaving of a 32-bit H value and a 32-bit E value, and therefore each HEcell 560 is SWcell32 562. The method 1300 then proceeds directly to step 1334. At step 1334, the program causes each thread in one or more CTAs 312 to store sub-alignment data across two arrays of (C+1) HEcells 560 when executing the SW sequence 740 for each combination of C query symbols and M target symbols. The method 1300 then terminates.

Figure 14:
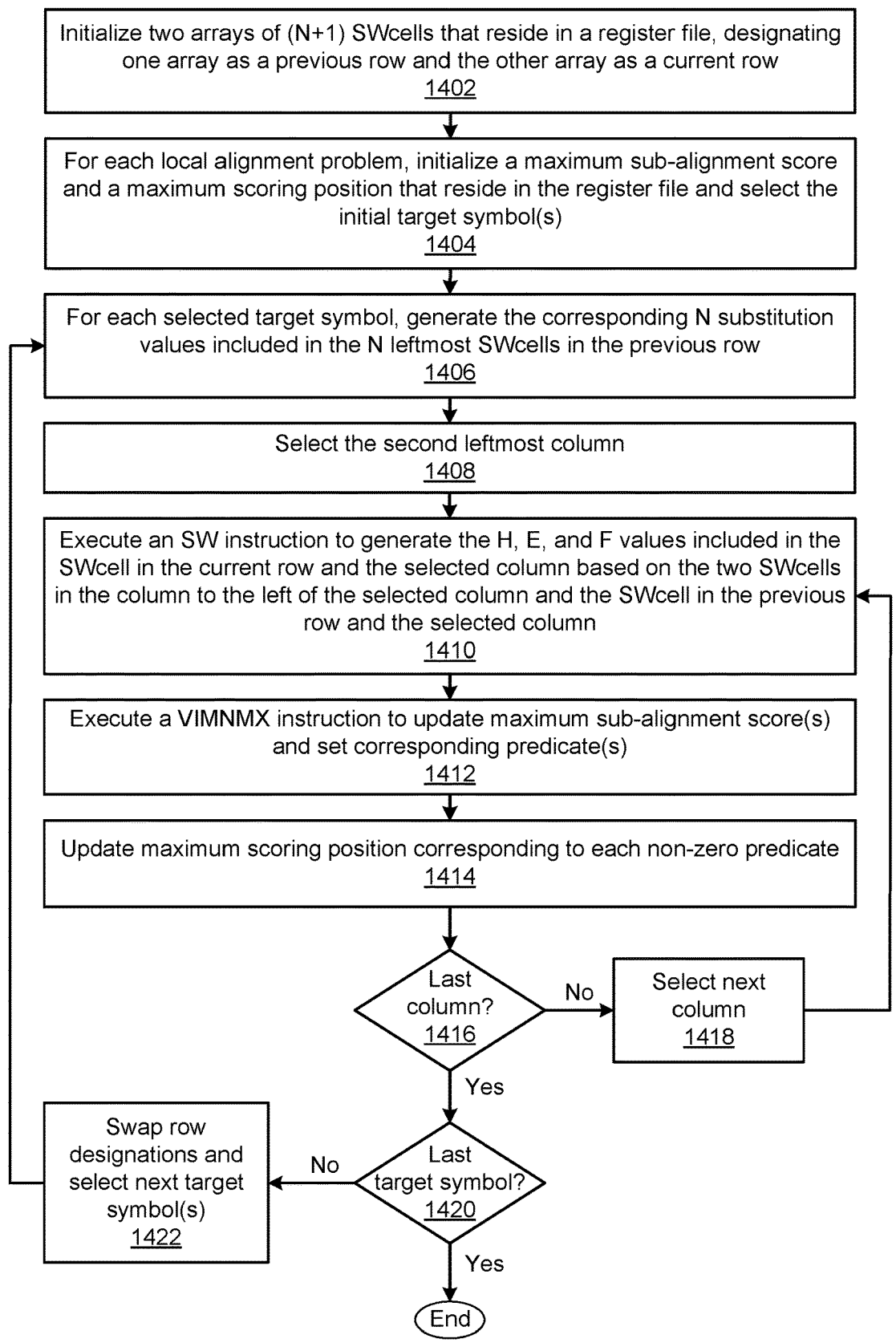
FIG. 14 is a flow diagram of method steps for performing sub-alignment computations via a single instruction when executing a matrix-filling phase of a Smith-Waterman algorithm, according to various embodiments.

FIG. 14 is a flow diagram of method steps for performing sub-alignment computations via a single instruction when executing a matrix-filling phase of a Smith-Waterman algorithm, according to various embodiments. Although the method steps are described with reference to the systems of FIGS. 1-4, 6, 8-9, and 11-12, persons skilled in the art will understand that any system configured to implement the method steps, in any order, falls within the scope of the present invention.

As shown, a method 1400 begins at step 1402, where a thread executing the SW kernel 192 initializes two arrays of (N+1) SWcells 460 that reside in a register file, designating one array as a previous row and the other array as a current row. At step 1404, for each local alignment problem, the thread initializes a maximum sub-alignment score and a maximum scoring position that reside in the register file and selects the initial target symbol(s). At step 1406, for each selected target symbol, the thread generates the corresponding N substitution values included in the N leftmost SWcells 460 in the previous row. At step 1408, the thread selects the second leftmost column.

At step 1410, the thread executes an SW instruction to generate the H, E, and F values included in the SWcell 460 in the current row and the selected column based on the two SWcells 460 in the column to the left of the selected column and the SWcellls 460 in the previous row and the selected column. At step 1412, the thread executes a VIMNMX instruction to update the maximum sub-alignment score(s) and set corresponding predicate(s). At step 1414, the thread updates the maximum scoring position corresponding to each non-zero predicate.

At step 1416, the thread determines whether the selected column is the last column, If, at step 1416, the thread determines that the selected column is not the last column, then the method 1400 proceeds to step 1418. At step 1418, the thread selects the next column. The method 1400 then returns to step 1410, where the thread executes an SW instruction to generate the H, E, and F values included in the SWcell 460 in the current row and the selected column.

If, however, at step 1416, the thread determines that the selected column is the last column, then the method 1400 proceeds directly to step 1420. At step 1420, the thread determines whether all of the selected target symbols are the last target symbols for the corresponding target sequences. If, at step 1420, the SW kernel 192 determines that at least one selected target symbol is not the last target symbol, then the method 1400 proceeds to step 1422. At step 1422 the SW kernel 192 swaps the row designations and selects the next target symbol(s). The method 1400 then returns to step 1406, where for each selected target symbol, the thread generates the corresponding N substitution values included in the N leftmost SWcells 460 in the previous row.

If, however, at step 1420, the SW kernel 192 determines that all of the selected target symbols are the last target symbols of the corresponding target sequences, then the method 1400 terminates.

Figure 15:
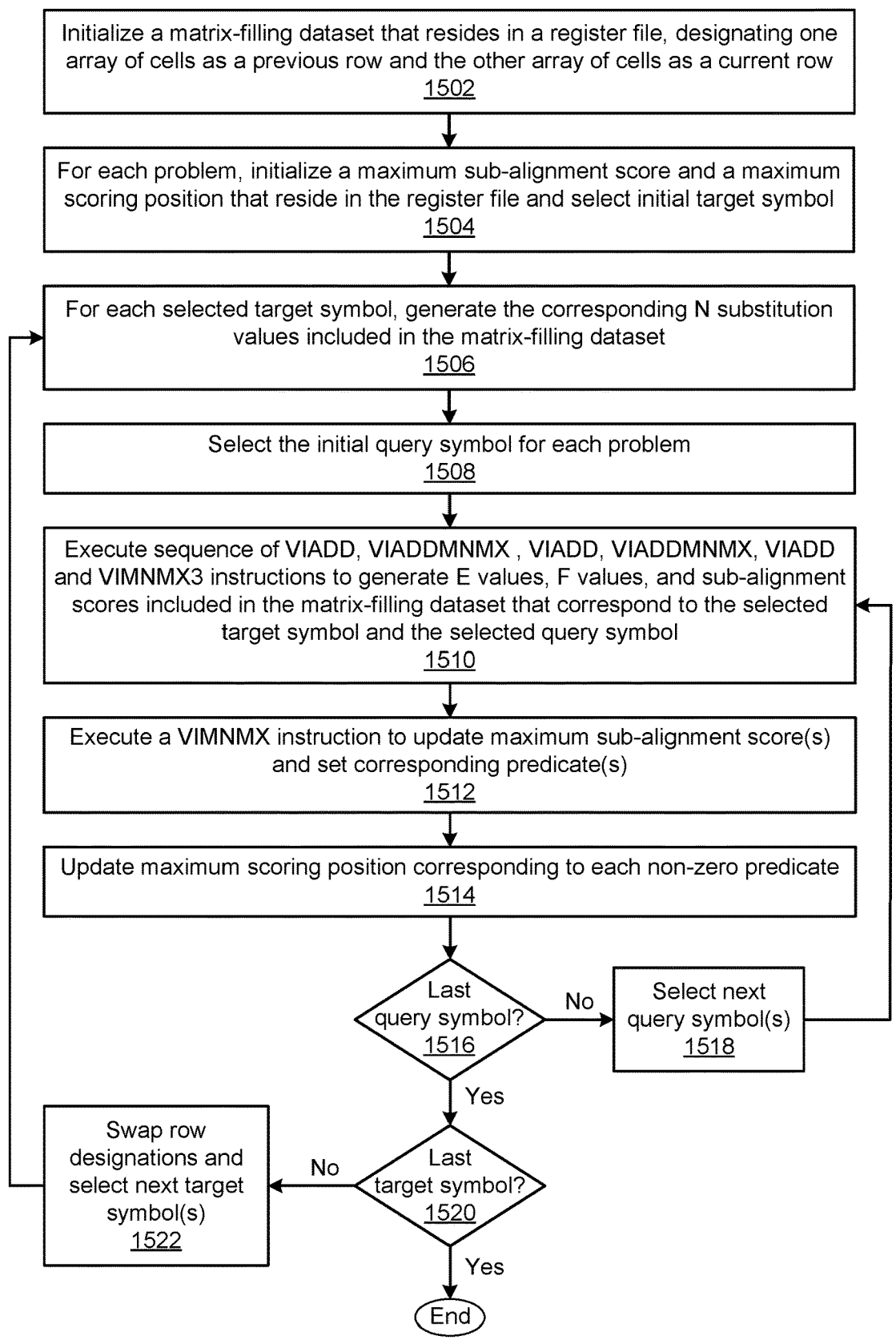
FIG. 15 is a flow diagram of method steps for performing sub-alignment computations via an instruction sequence when executing a matrix-filling phase of a Smith-Waterman algorithm, according to various embodiments.

FIG. 15 is a flow diagram of method steps for performing sub-alignment computations via an instruction sequence when executing a matrix-filling phase of a Smith-Waterman algorithm, according to various embodiments. Although the method steps are described with reference to the systems of FIGS. 1-5, 7-8, and 10-12, persons skilled in the art will understand that any system configured to implement the method steps, in any order, falls within the scope of the present invention.

As shown, a method 1500 begins at step 1502, where a thread executing the SW kernel 192 initializes a matrix-filling dataset (e.g., the matrix-filling dataset 490(0) or the matrix-filling dataset 490(1)) that resides in a register file, designating one array of cells as a previous row and the other array of cells as a current row. At step 1504, for each local alignment problem, the thread initializes a maximum sub-alignment score and a maximum scoring position that reside in the register file and selects an initial target symbol.

At step 1506, each selected target symbol, generate the corresponding N substitution values included in the matrix-filling dataset. At step 1508, the thread selects the initial query symbol for each local sub-alignment problem. At step 1510, the thread executes a sequence of VIADD, VIADDMNMX, VIADD, VIADDMNMX, VIADD and VIMNMX3 instructions to generate E values, F values, and sub-alignment scores included in the matrix-filling dataset that corresponds to the selected target symbol and the selected query symbol.

At step 1512, the thread executes a VIMNMX instruction to update the maximum sub-alignment score(s) and set corresponding predicate(s). At step 1514, the thread updates the maximum scoring position corresponding to each non-zero predicate.

At step 1516, the thread determines whether the selected query symbol is the query symbol, If, at step 1516, the thread determines that the selected query symbol is not the last query symbol, then the method 1500 proceeds to step 1518. At step 1518, the thread selects the next query symbol(s). The method 1500 then returns to step 1510, where the thread executes a sequence of VIADD, VIADDMNMX, VIADD, VIADDMNMX, VIADD and VIMNMX3 instructions to generate E values, F values, and sub-alignment score(s) included in the matrix-filling dataset corresponding to the selected target symbol and the selected query symbols.

If, however, at step 1516, the thread determines that the selected column is the last column, then the method 1500 proceeds directly to step 1520. At step 1520, the thread determines whether all of the selected target symbols are the last target symbols of the corresponding target sequences. If, at step 1520, the thread determines that at least one selected target symbol is not the last target symbol, then the method 1500 proceeds to step 1522. At step 1522 the thread swaps the row designations and selects the next target symbol(s). The method 1500 then returns to step 1506, where for each selected target symbol, the thread generates the corresponding N substitution values included in the N leftmost SWcells 460 or HEcells 560 in the previous row.

If, however, at step 1520, the thread determines that all of the selected target symbols are the last target symbols of the corresponding target sequences, then the method 1500 terminates.

Figure 16:
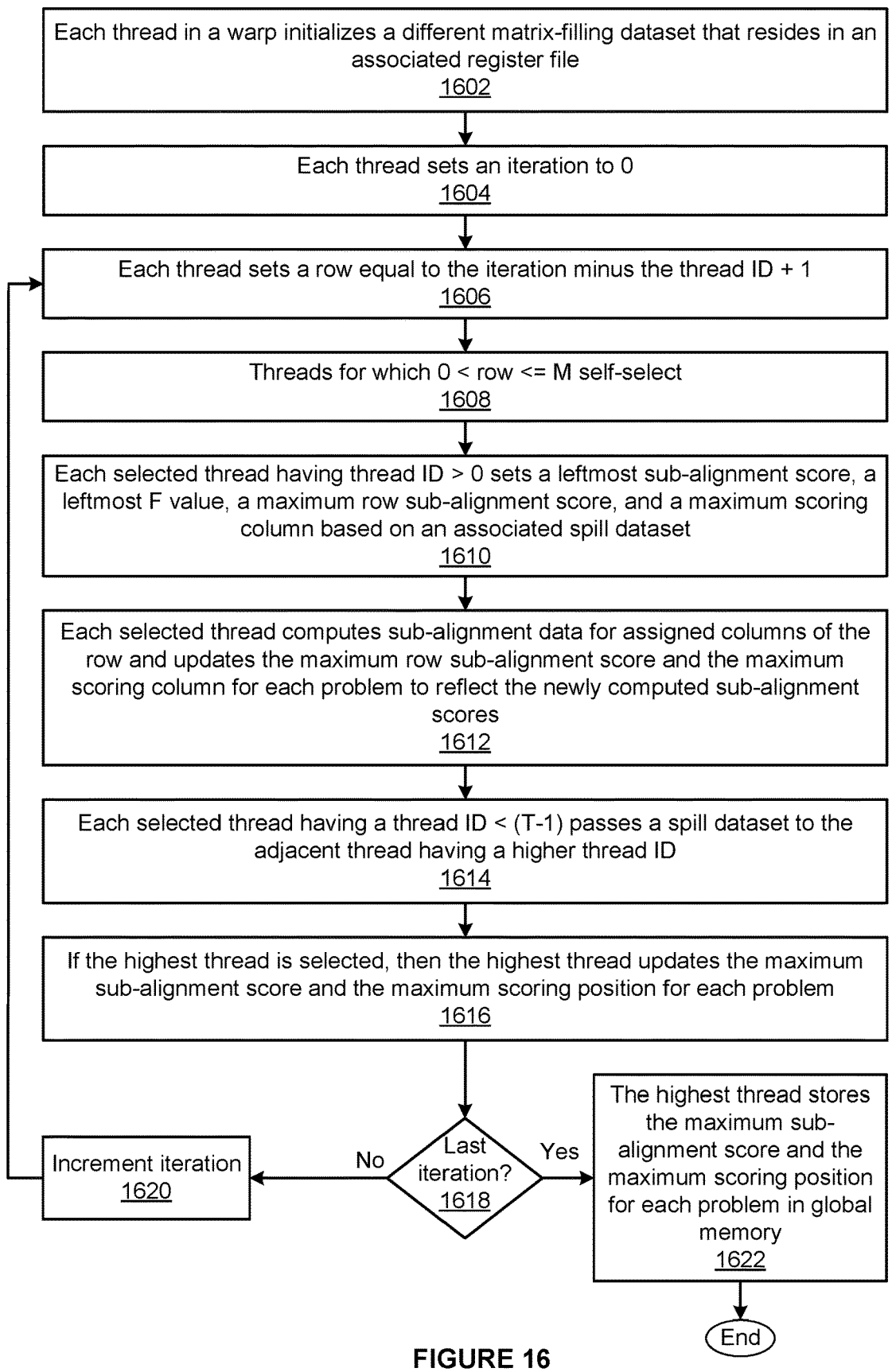
FIG. 16 is a flow diagram of method steps for executing a matrix-filling phase of a Smith-Waterman algorithm via a group of threads, according to various embodiments.

FIG. 16 is a flow diagram of method steps for executing a matrix-filling phase of a Smith-Waterman algorithm via a group of threads, according to various embodiments. Although the method steps are described with reference to the systems of FIGS. 1-12, persons skilled in the art will understand that any system configured to implement the method steps, in any order, falls within the scope of the present invention.

As shown, a method 1600 begins at step 1602, where each thread in a warp that is executing the SW kernel 192 executes initializes a different matrix-filling dataset (e.g., the matrix-filling dataset 490(0) or the matrix-filling dataset 490(1)) that resides in an associated register file. At step 1604, each thread sets an iteration to 0. At step 1606, each thread sets a row equal to the iteration minus the thread ID+1. At step 1608, threads having rows that are greater than 0 and less than or equal to M self-select.

At step 1610, each selected thread that has a thread ID greater than 0 sets a leftmost sub-alignment score, a leftmost F value, a maximum row sub-alignment score, and a maximum scoring column based on an associated spill dataset. At step 1612, each selected thread computes sub-alignment data for assigned columns of the row and updates the maximum row sub-alignment score and the maximum scoring column for each local alignment problem to reflect the newly computed sub-alignment scores. At step 1614, each selected thread having a thread ID that is less than (T−1) passes a spill dataset to the adjacent thread having a higher thread ID.

At step 1616, if the highest thread is selected, then the highest thread updates the maximum sub-alignment score and the maximum scoring position for each local alignment problem. At step 1618, the threads determine whether the current iteration is the last iteration. If, at step 1618, the threads determine that the current iteration is not the last iteration, then the threads proceed to step 1620. At step 1620, the threads increment the iteration. The method 1600 then returns to step 1606, where each thread sets a row equal to the iteration minus the thread ID+1.

If, however, at step 1618, the threads determine that the current iteration is the last iteration, then the threads proceed directly to step 1622. At step 1622, the thread having the highest thread ID stores the maximum sub-alignment score and the maximum scoring position for each local alignment problem in global memory. The method 1600 then terminates.

In some embodiments, one or more SW libraries in the programming platform software stack 160 and/or one or more SW kernels include, without limitation, pre-written code, kernels, subroutines, intrinsic functions, macros, classes, values, type specifications, etc., that facilitate the use of one or more of the interleaved cell layout 450(0), the interleaved cell layout 450(1), the SW instruction 610, the SW sequence 740, the interleaved cell layout 450(1), the VIADD instruction, the VIADDMNMX instruction, the VIMNMX3 instruction, the VIMNMX instruction 810, the SIMD multiple problems per thread technique, the SIMD staggered thread technique, or any combination thereof. In particular, one or more SW libraries can include, without limitation, intrinsic functions that compute sub-alignment data based on the SW instruction 610 and the interleaved cell layout 450(0), the SW sequence 740 and the interleaved cell layout 450(0), the SW sequence 740 and the interleaved cell layout 450(1), or any combination thereof.

In sum, the disclosed techniques can be used to efficiently accelerate the matrix-filling phase of a SW algorithm using a parallel processor. In some embodiments, a software application configures a warp to execute a SW kernel on a parallel processor in order to concurrently perform the matrix-filling phase for one to four local sequence alignment problems. In some embodiments, the SW kernel implements one or more data interleaving techniques, uses a single SW instruction or an SW instruction sequence to compute sub-alignment scores, uses a min/max instruction that indicates the selected operand to determine the maximum sub-alignment score and associated position, or any combination thereof. In the same or other embodiments, each thread of the warp is responsible for the matrix-filling phase for one, two, or four different alignment problems or a subset of the columns for one, two, or four shared alignment problems.

In some embodiments, each thread of the warp stores sub-alignment data for a prior row and a current row in an interleaved fashion via two arrays of cells that reside in a register file. More specifically, if the current row is j, then the kth cell in the array of cells corresponding to the current row stores 32-bits of data denoted H(j, k), 32-bits of data denoted E(j, k), 32-bits of data denoted F(j,k), and 32-bits of data denoted S(j+1, k+1). The kth cell in the other array of cells stores 32-bits of data representing H(j−1, k), 32-bits of data representing E(j−1, k), 32-bits of data denoted F(j−1,k), and 32-bits of data denoted S(j, k+1). Each of H(j, k), E(j, k), F(j,k), S(j+1, k+1), H(j−1, k), E(j−1, k), F(j−1,k), and S(j, k+1) can include a single 32-bit value corresponding to a single alignment problem, two packed 16-bit values corresponding to two alignment problems, or four packed 8-bit values corresponding to four alignment problems. The SW instruction and the SW instruction sequence can be used in conjunction with SW cells.

In some other embodiments, to reduce the amount of register memory needed to store sub-alignment data, each thread stores relevant H values and relevant E values for a prior row and a current row in two arrays of HE cells that reside in the register file, relevant F values for a current row via an array of 32-bit values that resides in the register file, and relevant S values for a current row in an array of 32-bit values that resides in the register file. The SW instruction sequence but not the single SW instruction can be used in conjunction with HE cells.

The SW instruction is a per-thread instruction that performs SW sub-alignment computations for a single location. In some embodiments, the SW instruction format is SW{.variant} result, diag, top, left, consts. The .variant modifier is 1 (no SIMD), 2 (2-way SIMD), or 4 (4-way SIMD); the result, diag, top, and left are instances of the SWcell; and the constants are GapDeleteExtend, GapinsertExtend, GapDeleteExtend, and GapinsertOpen.

The SW instruction sequence is a per-thread six instruction sequence that performs SW sub-alignment computations for a single location and supports no SIMD, 2-way SIMD, and 4-way SIMD. The instruction sequence includes, without limitation, a first VIADD instruction, a first VIADDMNMX instruction, a second VIADD instruction, a second VIADDMNMX instruction, a third VIADD instruction, and a VIMNMX3 instruction. Each of the VIADD instruction format, the VIADDMNMX instruction format, and the VIMNMX3 instruction format supports no SIMD, 2-way SIMD, and 4-way SIMD variants.

In some embodiments, each thread in the warp is responsible for one, two, or four different local alignment problems. Each thread in the thread group concurrently performs no SIMD, 1-way SIMD, or 4-way SIMD SW sub-alignment computations sequentially for positions corresponding to an associated set of columns and a row before performing scoring computations for positions corresponding to the set of columns and the next row. In some other embodiments, one, two, or four alignment problems are distributed between the threads of the warp. Each thread performs no SIMD, 1-way SIMD, or 4-way SIMD SW sub-alignment computations for positions corresponding to a different set of columns, and each thread except thread 0 is one row behind the immediately lower thread with respect to sub-alignment computations.

At least one technical advantage of the disclosed techniques relative to the prior art is that, with the disclosed techniques, the number of instructions executed to compute each sub-alignment score can be reduced when executing the matrix-filling phase of the SW algorithm using parallel processors. In that regard, with the disclosed techniques, a single SW instruction or a six-instruction SW sequence can be used to concurrently compute one, two, or four sub-alignment scores associated with one, two, or four different local alignment problems, respectively. Because sub-alignment scores and intermediate results associated with each position in the scoring matrix can be stored in an interleaved fashion within a single cell with the disclosed techniques, inefficiencies associated with data movement can be reduced relative to conventional techniques that retrieve the same data from separate matrices. Furthermore, with the disclosed techniques, an instruction that indicates the selected operand when determining the minimum or maximum of two operands can be used to reduce the number of instructions executed when determining and storing the maximum sub-alignment score and associated position. These technical advantages provide one or more technological improvements over prior art approaches.

Any and all combinations of any of the claim elements recited in any of the claims and/or any elements described in this application, in any fashion, fall within the contemplated scope of the embodiments and protection.

The descriptions of the various embodiments have been presented for purposes of illustration but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method, or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module," a "system," or a "computer." In addition, any hardware and/or software technique, process, function, component, engine, module, or system described in the present disclosure may be implemented as a circuit or set of circuits. Furthermore, aspects of the present disclosure may take the form of a computer program product embodied in one or more computer readable medium(s) having computer readable program codec embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory, a read-only memory, an erasable programmable read-only memory, Flash memory, an optical fiber, a portable compact disc read-only memory, an optical storage device, a magnetic storage device, or any suitable combination of the foregoing. In the context of this document, a computer readable storage medium may be any tangible medium that can contain or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A computer-implemented method for storing sub-alignment data when executing a matrix-filling phase of a Smith-Waterman algorithm, the method comprising:
   determining a top E value and a top sub-alignment score based on a top cell at a top position in a scoring matrix, wherein the scoring matrix is associated with at least a first target sequence and at least a first query sequence;
   computing a current E value that is associated with a current position in the scoring matrix based on the top E value and the top sub-alignment score;
   storing the current E value in a current cell at the current position in the scoring matrix;
   computing a current sub-alignment score that is associated with the current position in the scoring matrix based on the current E value, a diagonal sub-alignment score that is stored in a diagonal cell at a diagonal position in the scoring matrix, and a current substitution value that is associated with the first target sequence, the first query sequence, and the current position in the scoring matrix; and
   storing the current sub-alignment score in the current cell.

2. The computer-implemented method of claim 1, wherein computing the current sub-alignment score comprises:
   computing a current F value that is associated with the current position in the scoring matrix based on a left F value and a left sub-alignment score, wherein the left F value and the left sub-alignment score are stored in a left cell in a left position in the scoring matrix;
   storing the current F value in the current cell; and
   setting the current sub-alignment score equal to the maximum of the current F value, the current E value, a sum of the diagonal sub-alignment score and the current substitution value, and zero.

3. The computer-implemented method of claim 1, wherein computing the current sub-alignment score comprises:
   computing a current F value that is associated with the current position in the scoring matrix based on a left F value stored in an array of F values and a left sub-alignment score stored in a left cell in a left position in the scoring matrix;
   storing the current F value in the array of F values; and
   setting the current sub-alignment score equal to the maximum of the current F value, the current E value, a sum of the diagonal sub-alignment score and the current substitution value, and zero.

4. The computer-implemented method of claim 1, further comprising, prior to determining the top E value and the top sub-alignment score:
   computing a plurality of substitution values that includes the current substitution value; and
   storing the plurality of substitution values in an array of integers.

5. The computer-implemented method of claim 1, further comprising prior to determining the top E value and the top sub-alignment score:
   computing a plurality of substitution values that includes the current substitution value; and
   storing the current substitution value in the diagonal cell.

6. The computer-implemented method of claim 1, wherein determining the top E value and the top sub-alignment score comprises:
  unpacking a plurality of E values that includes the top E value from first packed data stored in the top cell, wherein the plurality of E values is associated with a plurality of local alignment problems; and
  unpacking a plurality of sub-alignment scores that includes the top sub-alignment score from second packed data stored in the top cell, wherein each sub-alignment score included in the plurality of sub-alignment scores is associated with the plurality of local alignment problems.

7. The computer-implemented method of claim 1, further comprising prior to determining the top E value and the top sub-alignment score, causing a first thread to allocate and initialize a matrix-filling dataset that includes a first array of cells associated with a first plurality of consecutive register locations and even rows in the scoring matrix and a second array of cells associated with a second plurality of consecutive register locations and odd rows in the scoring matrix, wherein the top cell is included in the first array of cells and the current cell is included in the second array of cells.

8. The computer-implemented method of claim 7, wherein the first array of cells includes an initial cell and a different cell for each symbol in the first query sequence.

9. The computer-implemented method of claim 7, wherein a first cell included in the first array of cells stores one, two, or four sub-alignment scores stored across 32 bits of sub-alignment score data, one, two, or four E values stored across 32 bits of E data, one, two, or four F values stored across 32 bits of F data, and one, two, or four substitution values stored across 32 bits of substitution data.

10. The computer-implemented method of claim 1, wherein storing the top E value and the top sub-alignment score in the top cell comprising packing the top E value and at least another top E value into first packed data included in the top cell and packing the top sub-alignment score and at least another top sub-alignment score into second packed data included in the top cell.

11. One or more non-transitory computer readable media including instructions that, when executed by one or more processors, cause the one or more processors to store sub-alignment data when executing a matrix-filling phase of a Smith-Waterman algorithm by performing the steps of:
  determining a top E value and a top sub-alignment score based on a top cell at a top position in a scoring matrix, wherein the scoring matrix is associated with at least a first target sequence and at least a first query sequence;
  computing a current E value that is associated with a current position in the scoring matrix based on the top E value and the top sub-alignment score;
  storing the current E value in a current cell at the current position in the scoring matrix;
  computing a current sub-alignment score that is associated with the current position in the scoring matrix based on the current E value, a diagonal sub-alignment score that is stored in a diagonal cell at a diagonal position in the scoring matrix, and a current substitution value that is associated with the first target sequence, the first query sequence, and the current position in the scoring matrix; and
  storing the current sub-alignment score in the current cell.

12. The one or more non-transitory computer readable media of claim 11, wherein computing the current sub-alignment score comprises:
  computing a current F value that is associated with the current position in the scoring matrix based on a left F value and a left sub-alignment score, wherein the left F value and the left sub-alignment score are stored in a left cell in a left position in the scoring matrix;
  storing the current F value in the current cell; and
  setting the current sub-alignment score equal to the maximum of the current F value, the current E value, a sum of the diagonal sub-alignment score and the current substitution value, and zero.

13. The one or more non-transitory computer readable media of claim 11, wherein computing the current sub-alignment score comprises:
  computing a current F value that is associated with the current position in the scoring matrix based on a left F value stored in an array of F values and a left sub-alignment score stored in a left cell in a left position in the scoring matrix;
  storing the current F value in the array of F values; and
  setting the current sub-alignment score equal to the maximum of the current F value, the current E value, a sum of the diagonal sub-alignment score and the current substitution value, and zero.

14. The one or more non-transitory computer readable media of claim 11, further comprising, prior to determining the top E value and the top sub-alignment score:
  computing a plurality of substitution values that includes the current substitution value; and
  storing the plurality of substitution values in an array of integers.

15. The one or more non-transitory computer readable media of claim 11, further comprising, prior to determining the top E value and the top sub-alignment score:
  computing a plurality of substitution values that includes the current substitution value; and
  storing the current substitution value in the diagonal cell.

16. The one or more non-transitory computer readable media of claim 11, wherein the top cell stores 32 bits of sub-alignment score data that comprises the top sub-alignment score, a sequence of two 16-bit sub-alignment scores that includes the top sub-alignment score, or a sequence of four 8-bit sub-alignment scores that includes the top sub-alignment score.

17. The one or more non-transitory computer readable media of claim 11, further comprising, prior to determining the top E value and the top sub-alignment score, causing a first thread to allocate and initialize a matrix-filling dataset that includes a first array of cells associated with a first plurality of consecutive register locations and even rows in the scoring matrix and a second array of cells associated with a second plurality of consecutive register locations and odd rows in the scoring matrix, wherein the top cell is included in the first array of cells and the current cell is included in the second array of cells.

18. The one or more non-transitory computer readable media of claim 17, wherein the first array of cells includes an initial cell and a different cell for each symbol in a first subset of the first query sequence that is assigned to the first thread.

19. The one or more non-transitory computer readable media of claim 17, wherein a first cell included in the first array of cells stores one, two, or four sub-alignment scores across 32 bits of sub-alignment score data and one, two, or four E values across 32 bits of E data, and wherein the matrix-filling dataset further includes at least the current substitution value and a third array of F values associated with a third plurality of consecutive register locations.

20. A system comprising:
one or more memories storing instructions; and
one or more processors coupled to the one or more memories that, when executing the instructions, perform the steps of:
  determining a top E value and a top sub-alignment score based on a top cell at a top position in a scoring matrix, wherein the scoring matrix is associated with at least a first target sequence and at least a first query sequence;
  computing a current E value that is associated with a current position in the scoring matrix based on the top E value and the top sub-alignment score;
  storing the current E value in a current cell at the current position in the scoring matrix;
  computing a current sub-alignment score that is associated with the current position in the scoring matrix based on the current E value, a diagonal sub-alignment score that is stored in a diagonal cell at a diagonal position in the scoring matrix, and a current substitution value that is associated with the first target sequence, the first query sequence, and the current position in the scoring matrix; and
  storing the current sub-alignment score in the current cell.

* * * * *